(12) United States Patent
Brown

(10) Patent No.: US 8,927,705 B2
(45) Date of Patent: Jan. 6, 2015

(54) SINGLE STRANDED EXTENDED DICER SUBSTRATE AGENTS AND METHODS FOR THE SPECIFIC INHIBITION OF GENE EXPRESSION

(71) Applicant: Dicerna Pharmaceuticals, Inc., Watertown, MA (US)

(72) Inventor: Bob D. Brown, Millington, NJ (US)

(73) Assignee: Dicerna Pharmaceuticals, Inc., Watertown, MA (US)

( * ) Notice: Subject to any disclaimer, the term of this patent is extended or adjusted under 35 U.S.C. 154(b) by 215 days.

(21) Appl. No.: 13/708,185

(22) Filed: Dec. 7, 2012

(65) Prior Publication Data

US 2013/0096290 A1 Apr. 18, 2013

Related U.S. Application Data

(60) Division of application No. 12/824,011, filed on Jun. 25, 2010, now Pat. No. 8,349,809, which is a continuation-in-part of application No. 12/704,256, filed on Feb. 11, 2010, now abandoned, and a continuation-in-part of application No. 12/642,371, filed on Dec. 18, 2009, now Pat. No. 8,513,207.

(60) Provisional application No. 61/151,841, filed on Feb. 11, 2009, provisional application No. 61/138,946, filed on Dec. 18, 2008, provisional application No. 61/166,227, filed on Apr. 2, 2009, provisional application No. 61/173,505, filed on Apr. 28, 2009, provisional application No. 61/173,514, filed on Apr. 28, 2009, provisional application No. 61/173,521, filed on Apr. 28, 2009, provisional application No. 61/173,525, filed on Apr. 28, 2009, provisional application No. 61/173,532, filed on Apr. 28, 2009, provisional application No. 61/173,538, filed on Apr. 28, 2009, provisional application No. 61/173,544, filed on Apr. 28, 2009, provisional application No. 61/173,549, filed on Apr. 28, 2009, provisional application No. 61/173,554, filed on Apr. 28, 2009, provisional application No. 61/173,556, filed on Apr. 28, 2009, provisional application No. 61/173,558, filed on Apr. 28, 2009, provisional application No. 61/173,563, filed on Apr. 28, 2009.

(51) Int. Cl.
*C07H 21/00* (2006.01)
*C12N 15/113* (2010.01)
*A61K 31/713* (2006.01)
*C12N 15/11* (2006.01)

(52) U.S. Cl.
CPC .......... *C12N 15/1135* (2013.01); *A61K 31/713* (2013.01); *C12N 15/111* (2013.01); *C12N 2310/14* (2013.01); *C12N 2310/51* (2013.01); *C12N 2310/533* (2013.01); *C12N 2320/53* (2013.01)
USPC ....................................................... 536/24.5

(58) Field of Classification Search
CPC combination set(s) only.
See application file for complete search history.

(56) References Cited

U.S. PATENT DOCUMENTS

| | | | |
|---|---|---|---|
| 2004/0142895 A1 | 7/2004 | Lorckridge et al. | 514/44 |
| 2005/0171039 A1 | 8/2005 | McSwiggen et al. | 514/44 |
| 2005/0244858 A1 | 11/2005 | Rossi et al. | 435/6 |
| 2005/0277610 A1 | 12/2005 | Rossi et al. | 514/44 |
| 2007/0265220 A1 | 11/2007 | Rossi et al. | 514/44 |
| 2009/0082217 A1 | 3/2009 | Smolke et al. | 506/9 |
| 2009/0306184 A1 | 12/2009 | McSwiggen et al. | 514/44 A |
| 2010/0173974 A1 | 7/2010 | Brown | 514/44 A |
| 2010/0249214 A1 | 9/2010 | Brown | 514/44 A |

FOREIGN PATENT DOCUMENTS

| WO | WO 2007/056153 | 5/2007 | A61K 47/48 |
|---|---|---|---|
| WO | WO 2010/093788 | 8/2010 | A61K 31/713 |

OTHER PUBLICATIONS

Authorized Officer: Lee W. Young, International Search Report for related application PCT/US2010/23891, dated Aug. 9, 2010, 12 pages.

*Primary Examiner* — Jennifer McDonald
(74) *Attorney, Agent, or Firm* — Sunstein Kann Murphy & Timbers LLP

(57) ABSTRACT

The invention provides compositions and methods for reducing expression of a target gene in a cell, involving contacting a cell with an isolated double stranded nucleic acid (dsNA) in an amount effective to reduce expression of a target gene in a cell. The dsNAs of the invention possess a single stranded extension (in most embodiments, the single stranded extension comprises at least one modified nucleotide and/or phosphate back bone modification). Such single stranded extended Dicer-substrate siRNAs (DsiRNAs) were demonstrated to be effective RNA inhibitory agents compared to corresponding double stranded DsiRNAs.

46 Claims, 29 Drawing Sheets

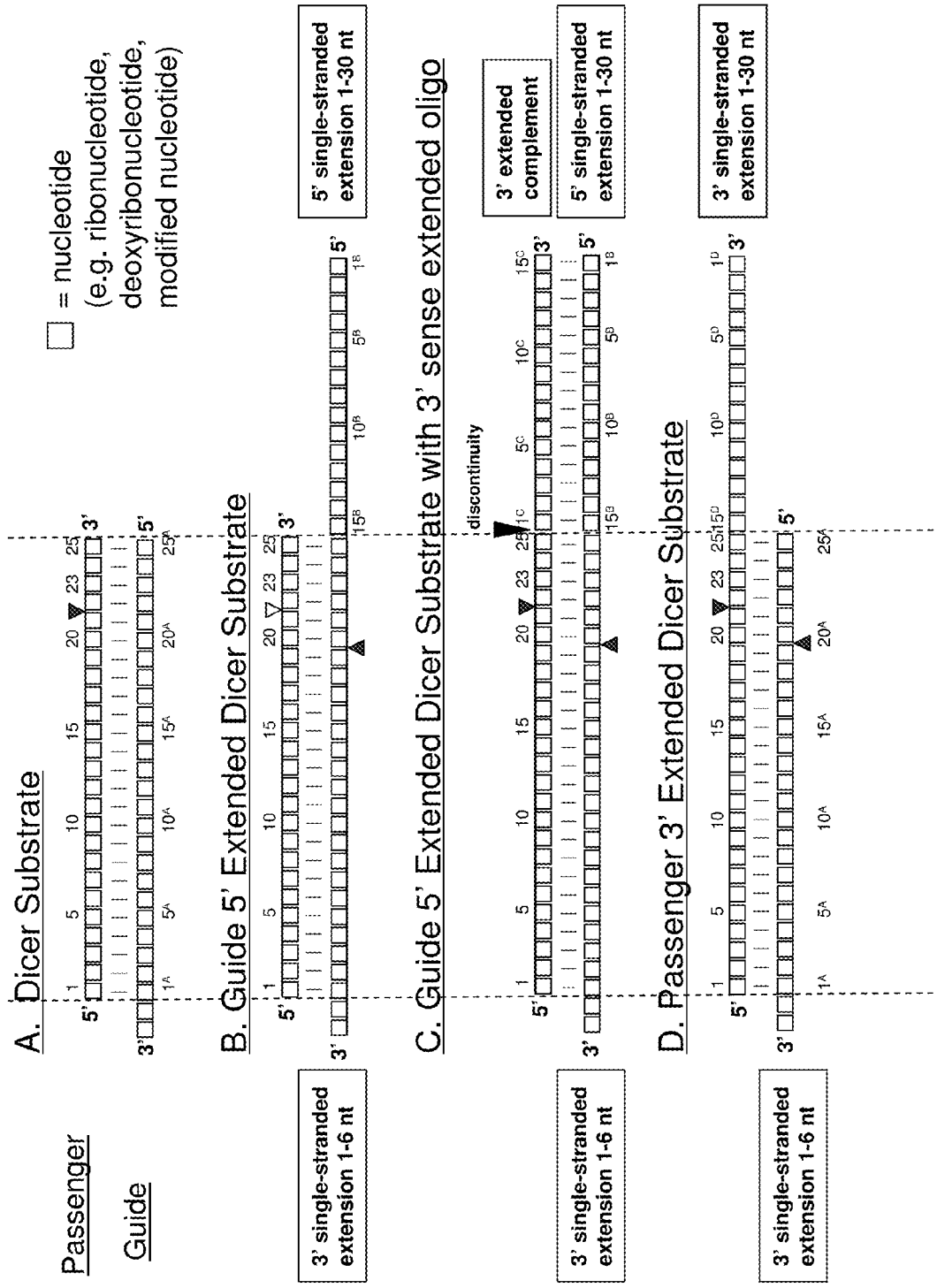

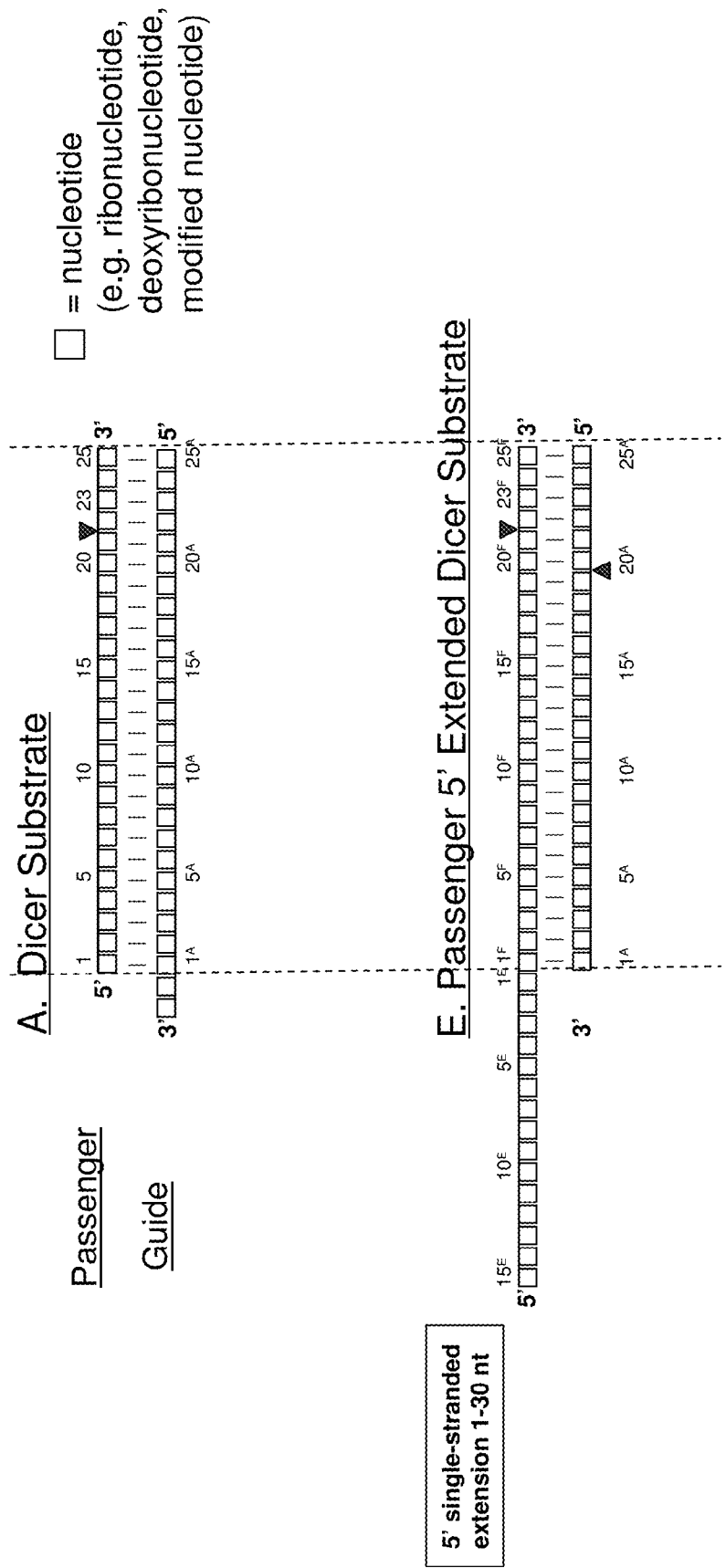
Figure 1A. (continued) DsiRNA with ssDNA/RNA strand extensions

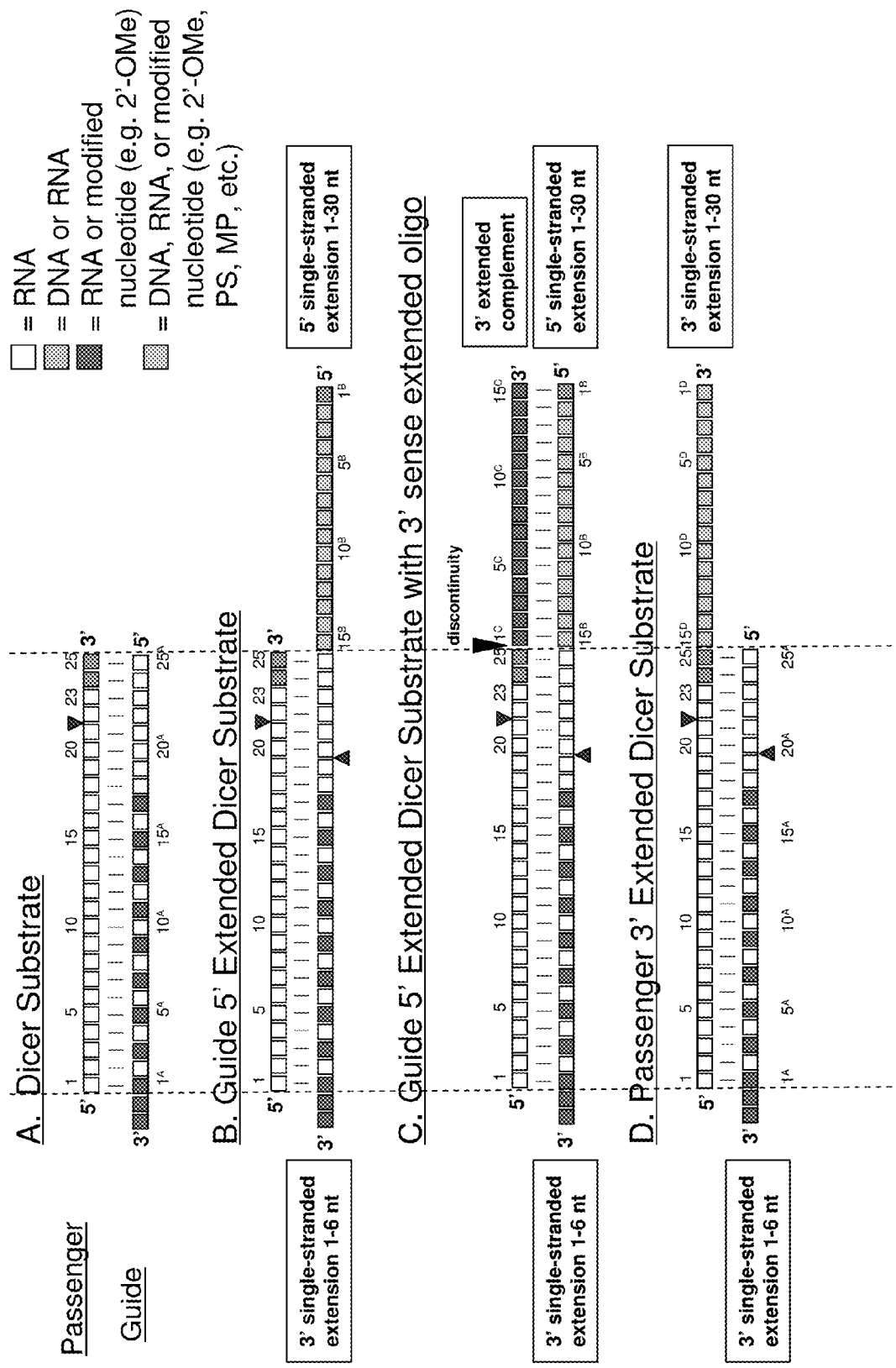

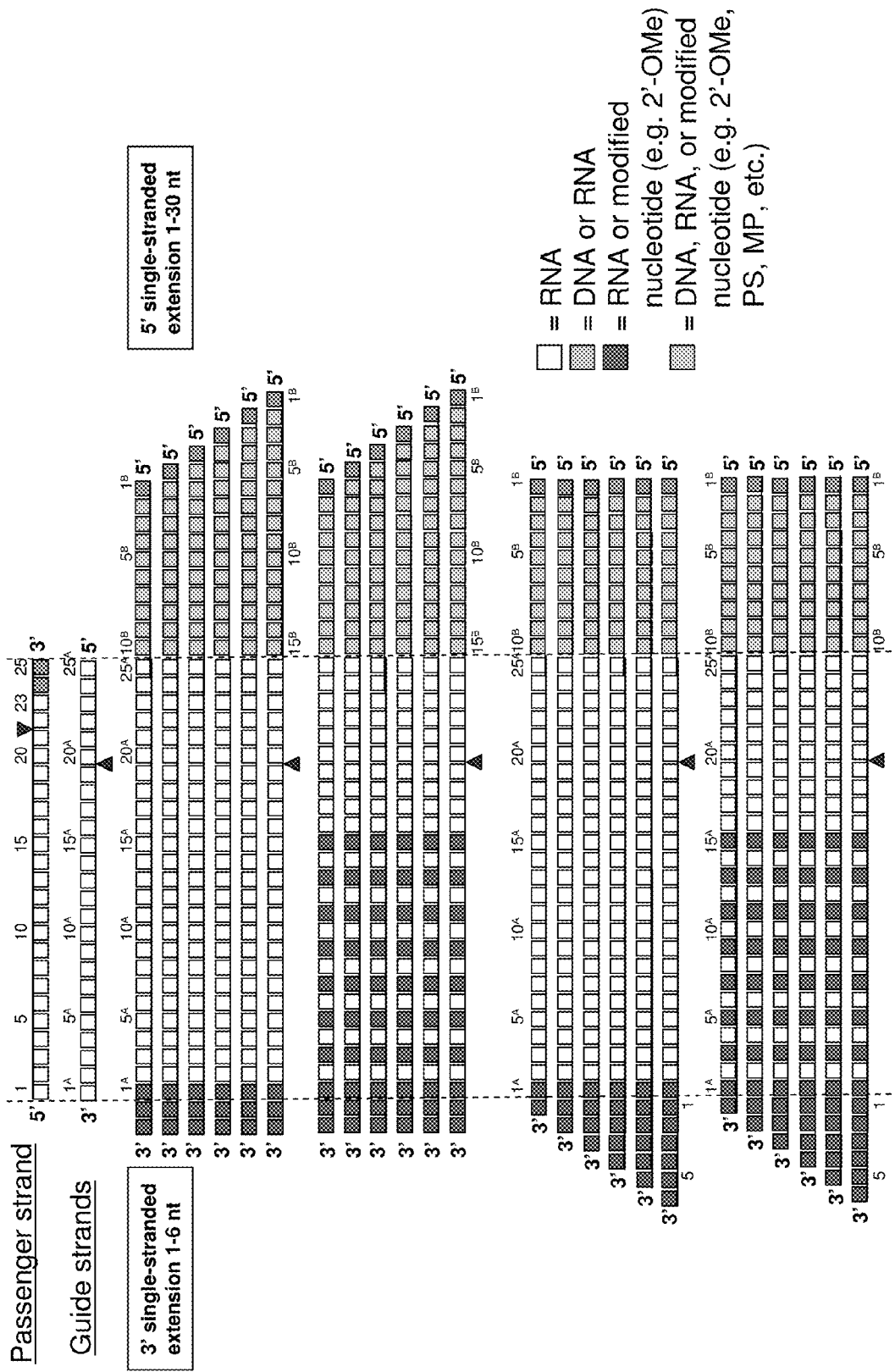
Figure 2. DsiRNA with ssDNA/RNA guide strand extensions

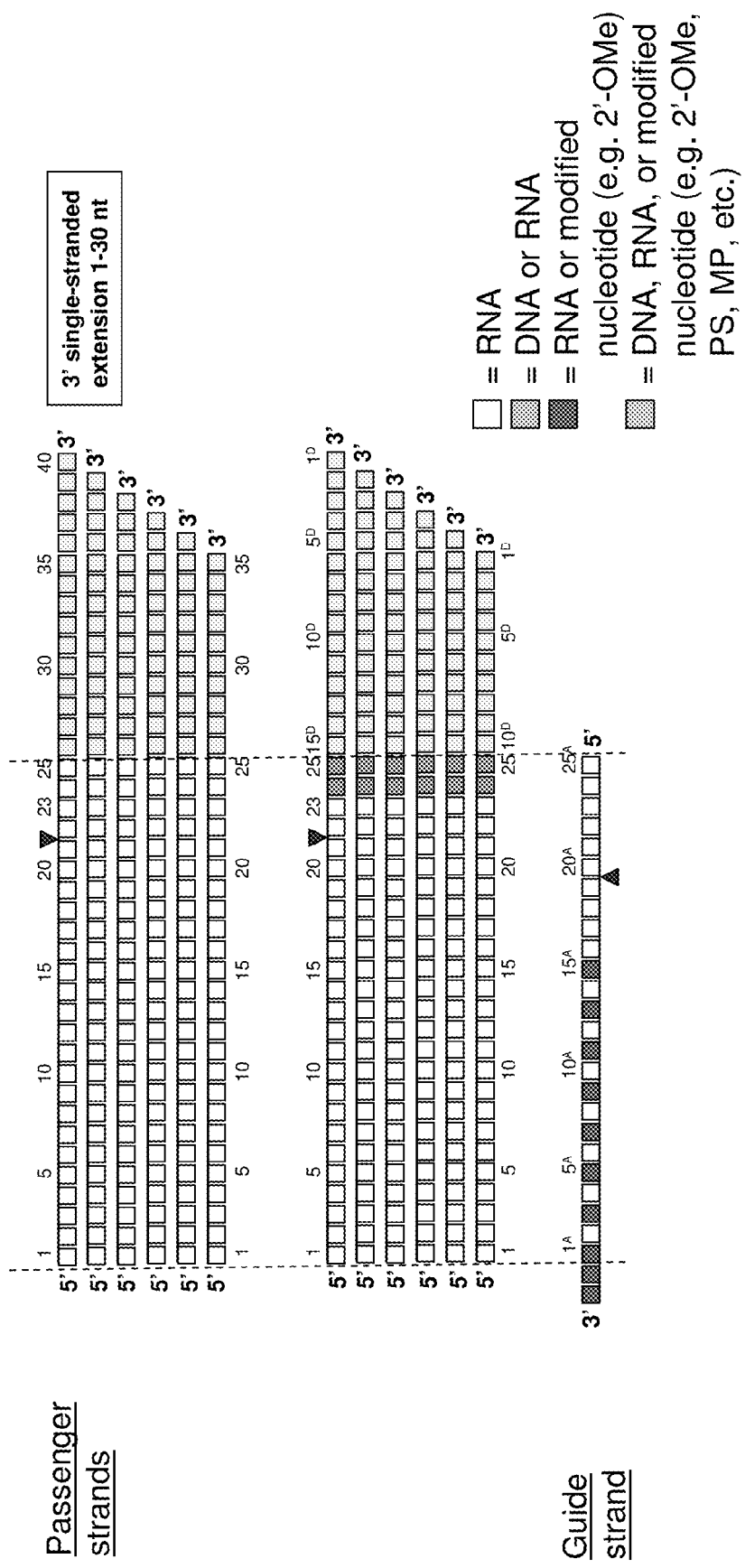
Figure 3. DsiRNA with ssDNA/RNA passenger strand extensions

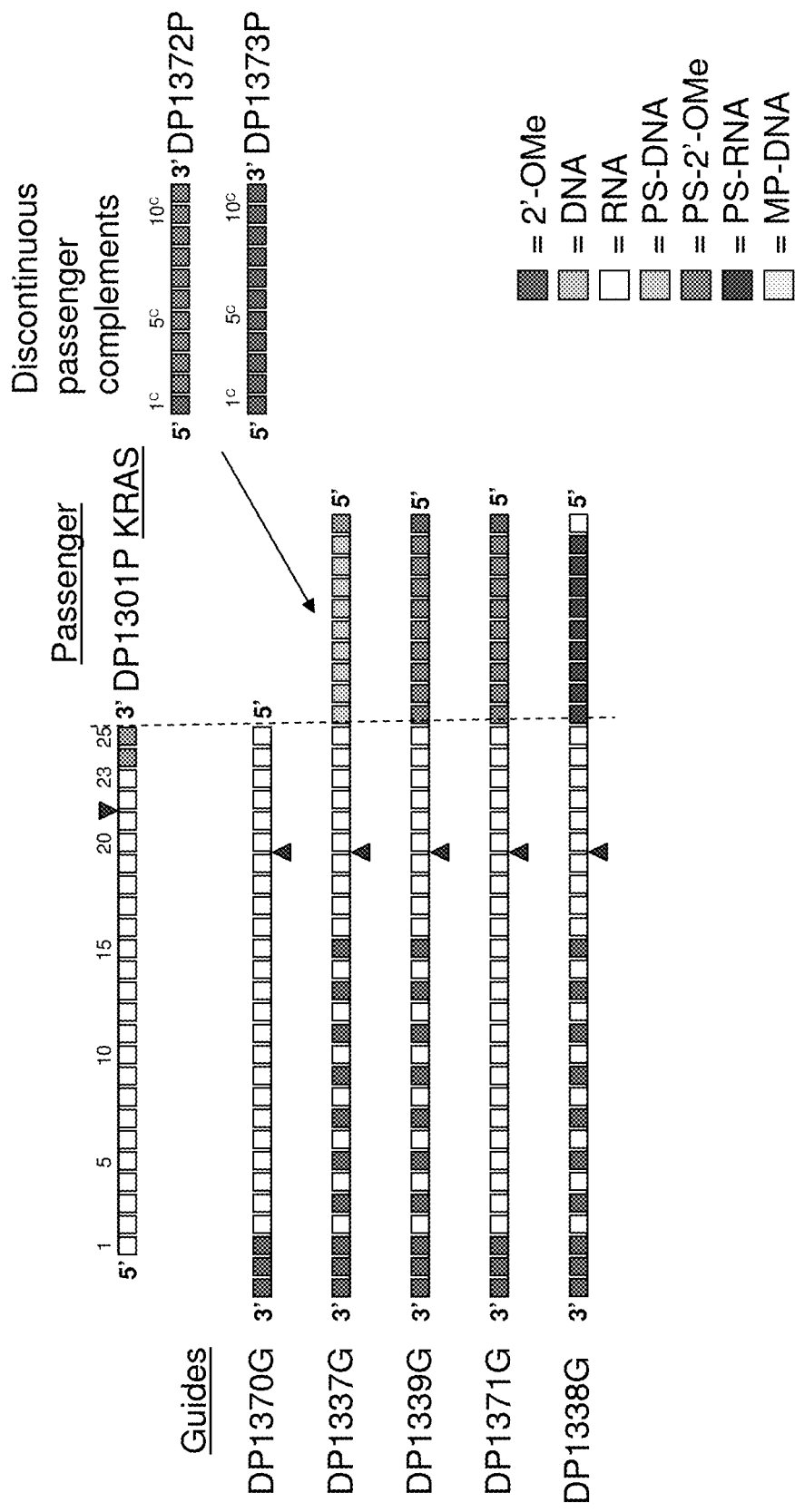
Figure 4. DsiRNA with ssDNA/RNA guide extensions

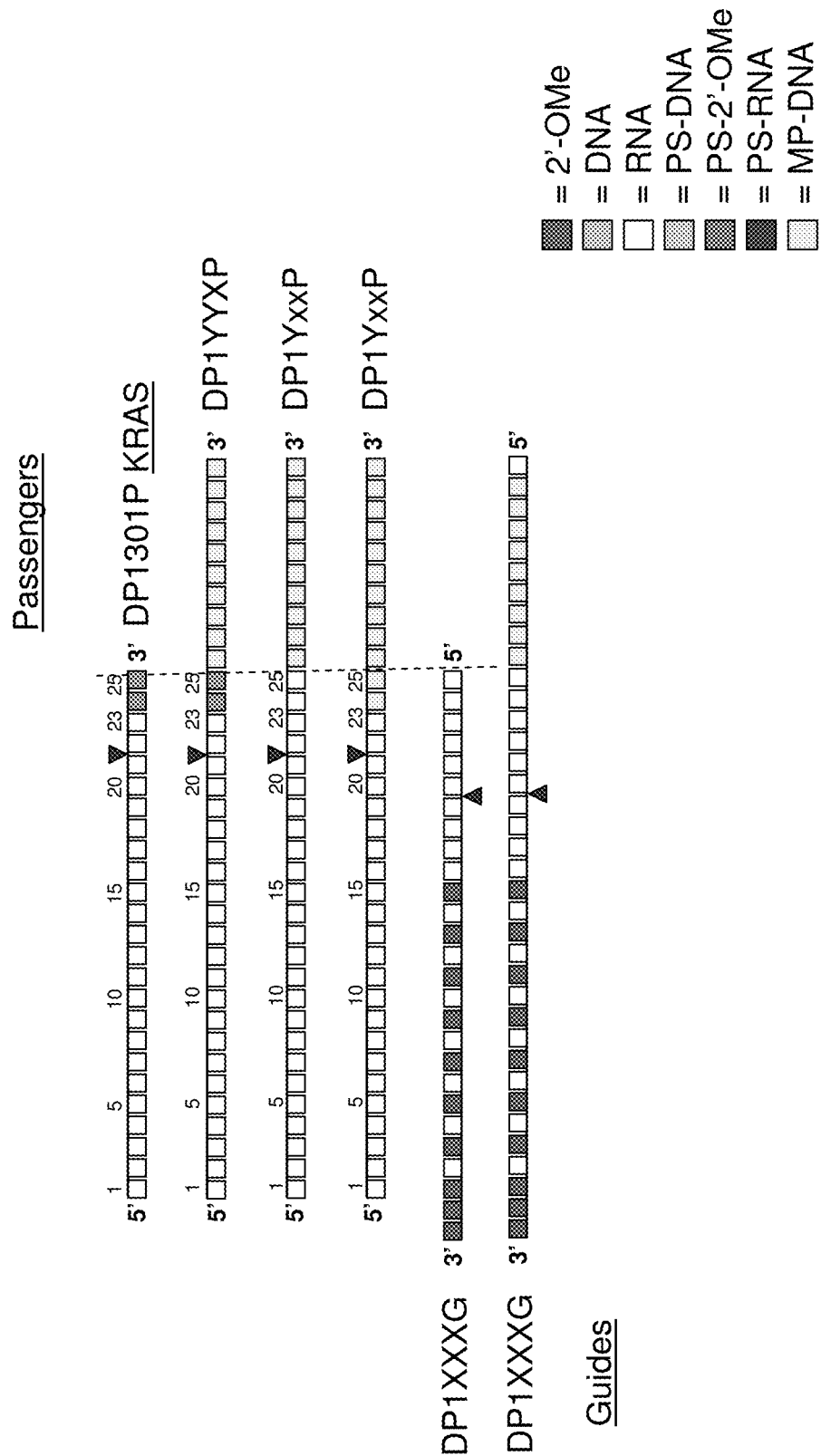
Figure 5. DsiRNA with ssDNA/RNA passenger strand extensions

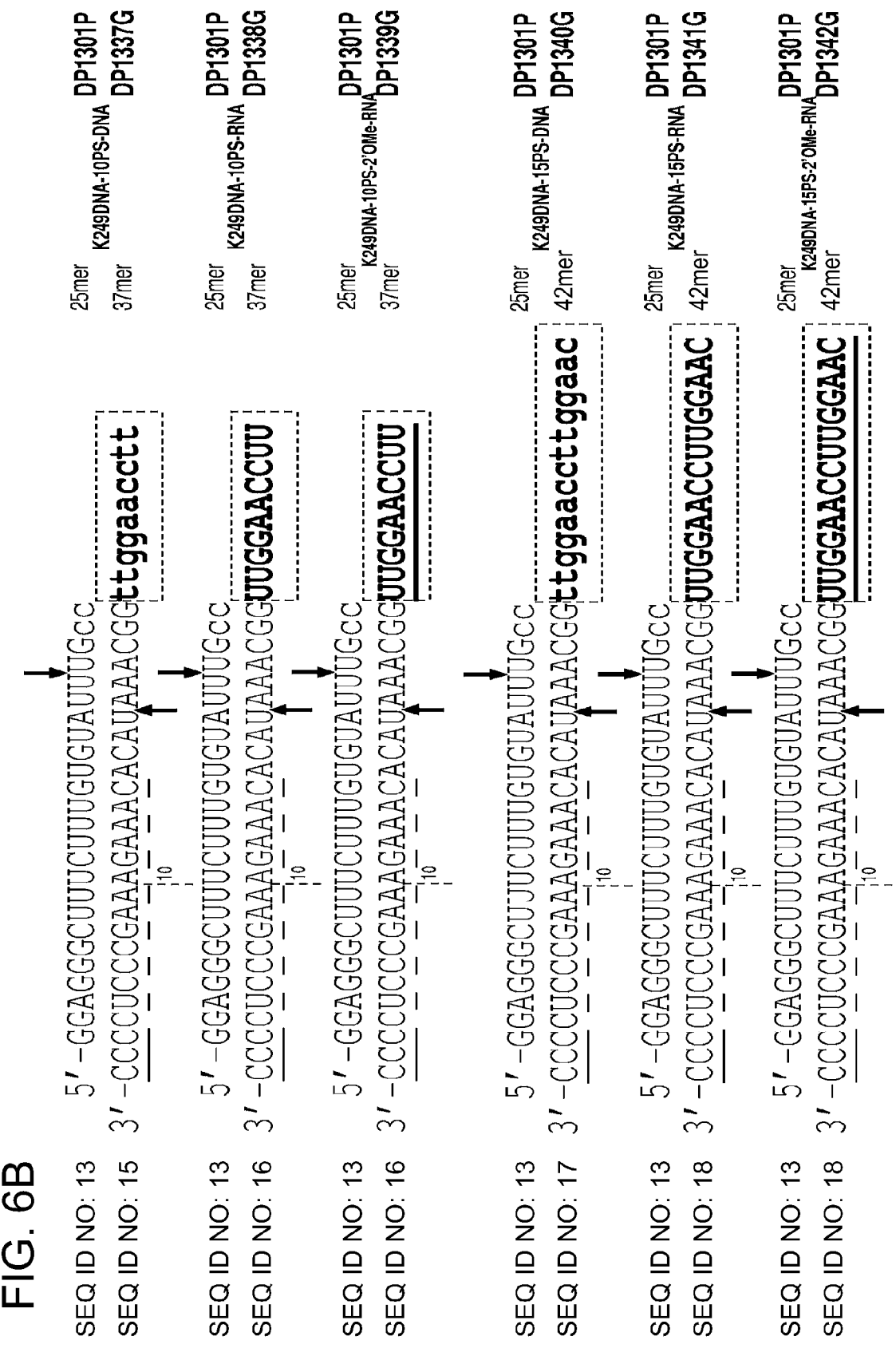

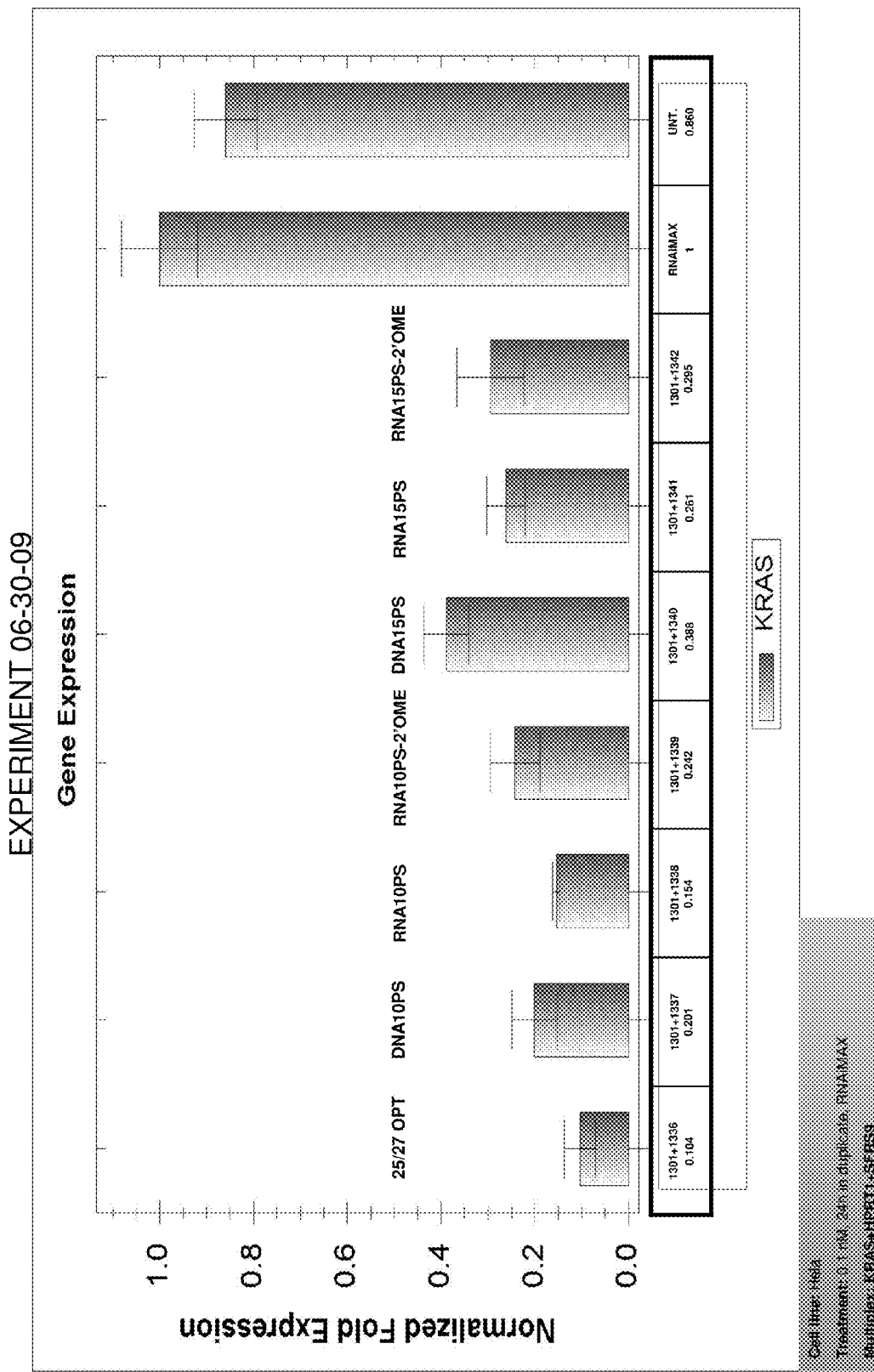
Figure 7. Different length ssDNA/RNA extensions KRAS-249

Different length ssDNA/RNA extensions HPRT1

SEQ ID NO: 19  5'-GCCAGACUUUGUUGGAUUUGAAAtt        25mer  HPRT1  DP1001P
SEQ ID NO: 20  3'-UUCGGUCUCGAAACAACCUAAAACUUUAA    27mer         DP1002G

FIG. 8B

| | | | | |
|---|---|---|---|---|
| SEQ ID NO: 19 | 5'-GCCAGACUUUGUUGGAUUUGAAAUU | 25mer | HPRT1DNA10PS | DP1001P |
| SEQ ID NO: 21 | 3'-UUCGGUCUGAAACAACCUAAACUUUAAttggaacctt | 37mer | | DP1350G |
| SEQ ID NO: 19 | 5'-GCCAGACUUUGUUGGAUUUGAAAUU | 25mer | HPRT1RNA10PS | DP1001P |
| SEQ ID NO: 22 | 3'-UUCGGUCUGAAACAACCUAAACUUUAAAUUGGAACCUU | 37mer | | DP1351G |
| SEQ ID NO: 19 | 5'-GCCAGACUUUGUUGGAUUUGAAAUU | 25mer | HPRT1RNA10PS-2'OME | DP1001P |
| SEQ ID NO: 22 | 3'-UUCGGUCUGAAACAACCUAAACUUUAAAUUGGAACCUU | 37mer | | DP1352G |
| SEQ ID NO: 19 | 5'-GCCAGACUUUGUUGGAUUUGAAAUU | 25mer | HPRT1DNA15PS | DP1001P |
| SEQ ID NO: 23 | 3'-UUCGGUCUGAAACAACCUAAACUUUAAttggaaccttggaac | 42mer | | DP1353G |
| SEQ ID NO: 19 | 5'-GCCAGACUUUGUUGGAUUUGAAAUU | 25mer | HPRT1RNA15PS | DP1001P |
| SEQ ID NO: 24 | 3'-UUCGGUCUGAAACAACCUAAACUUUAAAUUGGAACCUUGGAAC | 42mer | | DP1354G |
| SEQ ID NO: 19 | 5'-GCCAGACUUUGUUGGAUUUGAAAUU | 25mer | HPRT1RNA15PS-2'OME | DP1001P |
| SEQ ID NO: 24 | 3'-UUCGGUCUGAAACAACCUAAACUUUAAAUUGGAACCUUGGAAC | 42mer | | DP1355G |

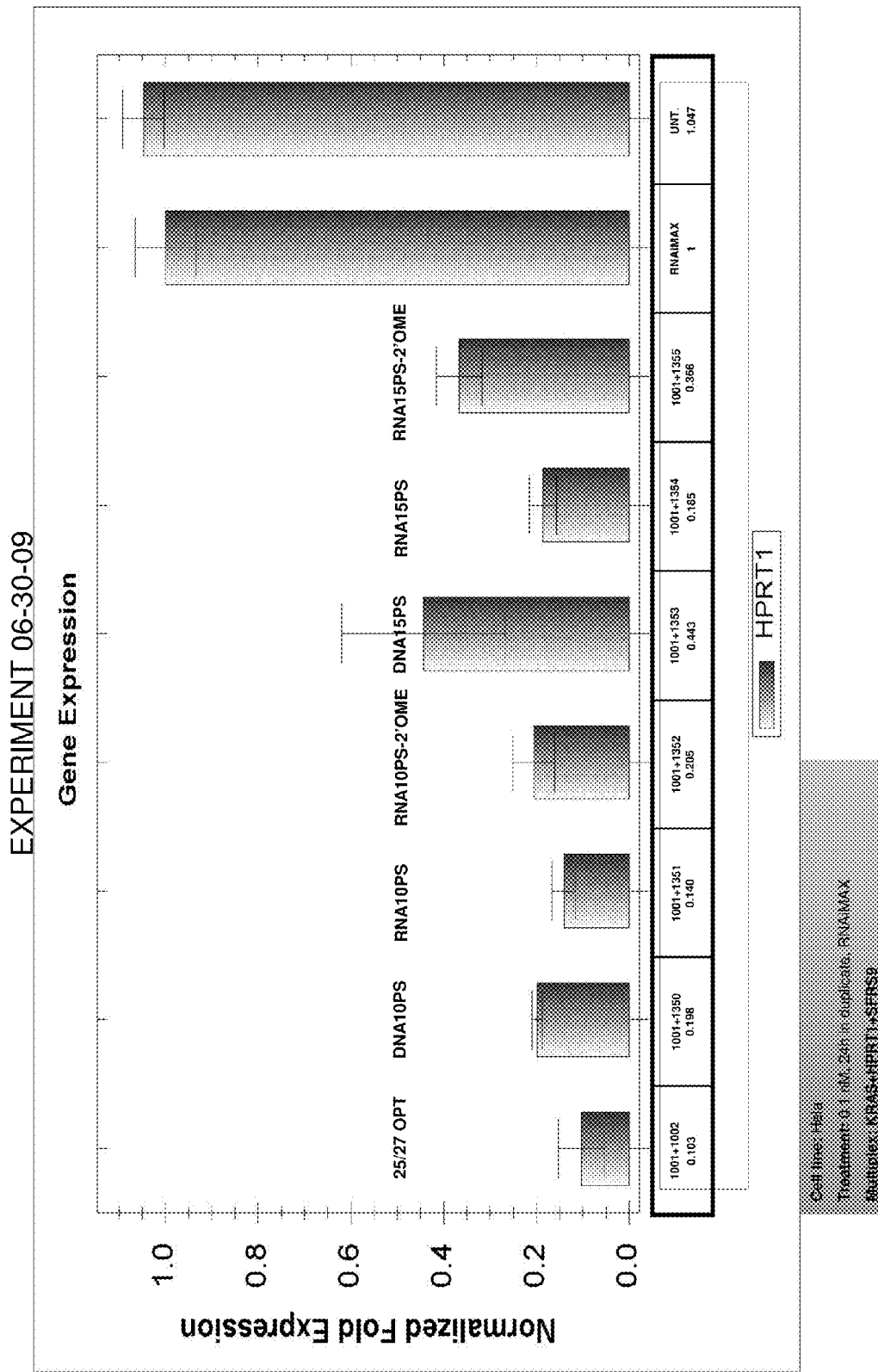

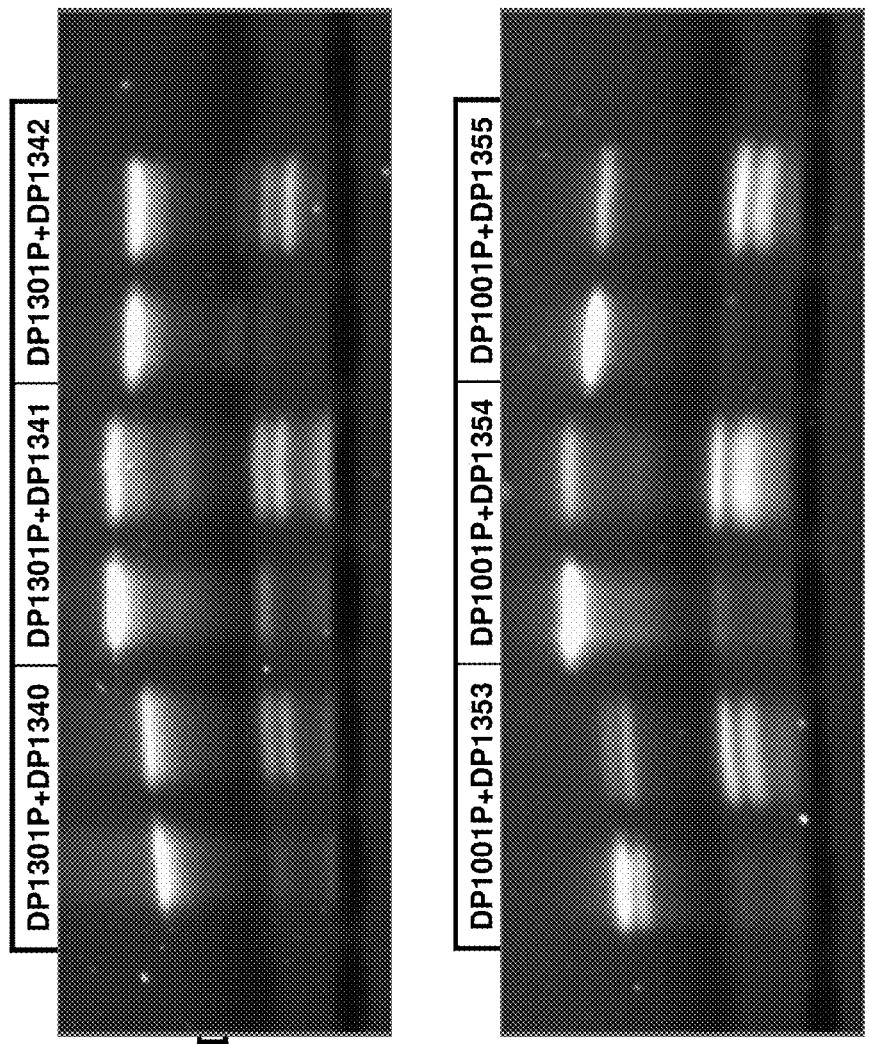
Figure 10. Different length ssDNA/RNA extensions DICING ASSAY

FIG. 11

Short oligos that complement the ssExtensions

RNA15  DP1365P

SEQ ID NO: 25  5'-AACCUUGGAACCUUG-3'
SEQ ID NO: 27  3'-UUGGAACCUUGGAAC-5'

PS-RNA15  DP1366P

SEQ ID NO: 25  5'-AACCUUGGAACCUUG-3'
SEQ ID NO: 27  3'-UUGGAACCUUGGAAC-5'

PS-DNA15  DP1367P

SEQ ID NO: 26  5'-*aaccttggaaccttg*-3'
SEQ ID NO: 27  3'-UUGGAACCUUGGAAC-5'

PS-2'OMe-RNA15  DP1368P

SEQ ID NO: 25  5'-AACCUUGGAACCUUG-3'
SEQ ID NO: 27  3'-UUGGAACCUUGGAAC-5'

2'OMe-RNA15  DP1369P

SEQ ID NO: 25  5'-AACCUUGGAACCUUG-3'
SEQ ID NO: 27  3'-UUGGAACCUUGGAAC-5'

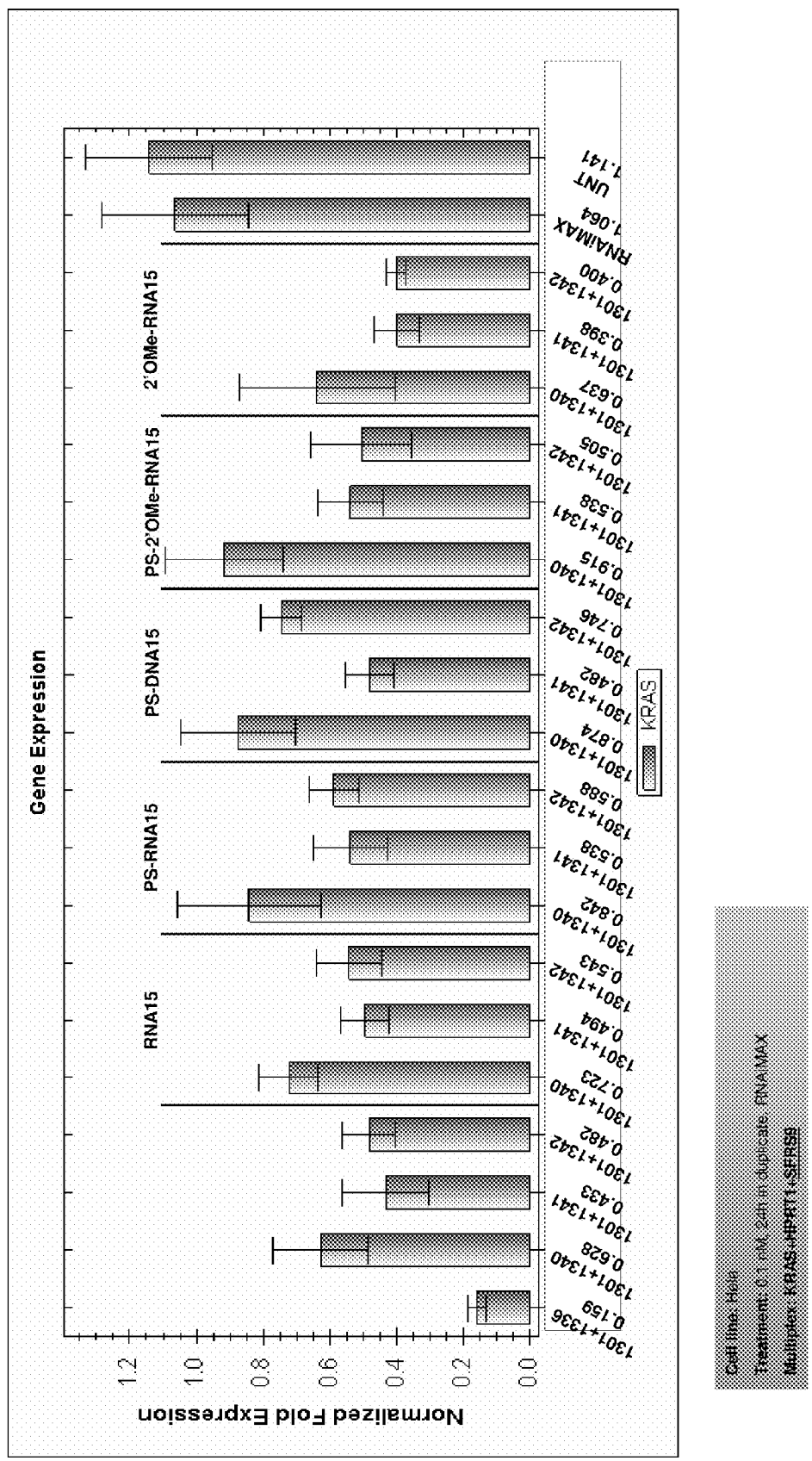
Figure 12. 15bp length ssDNA/RNA extensions + 15bp oligos that complement the extensions KRAS-249M
EXPERIMENT 07-27-09

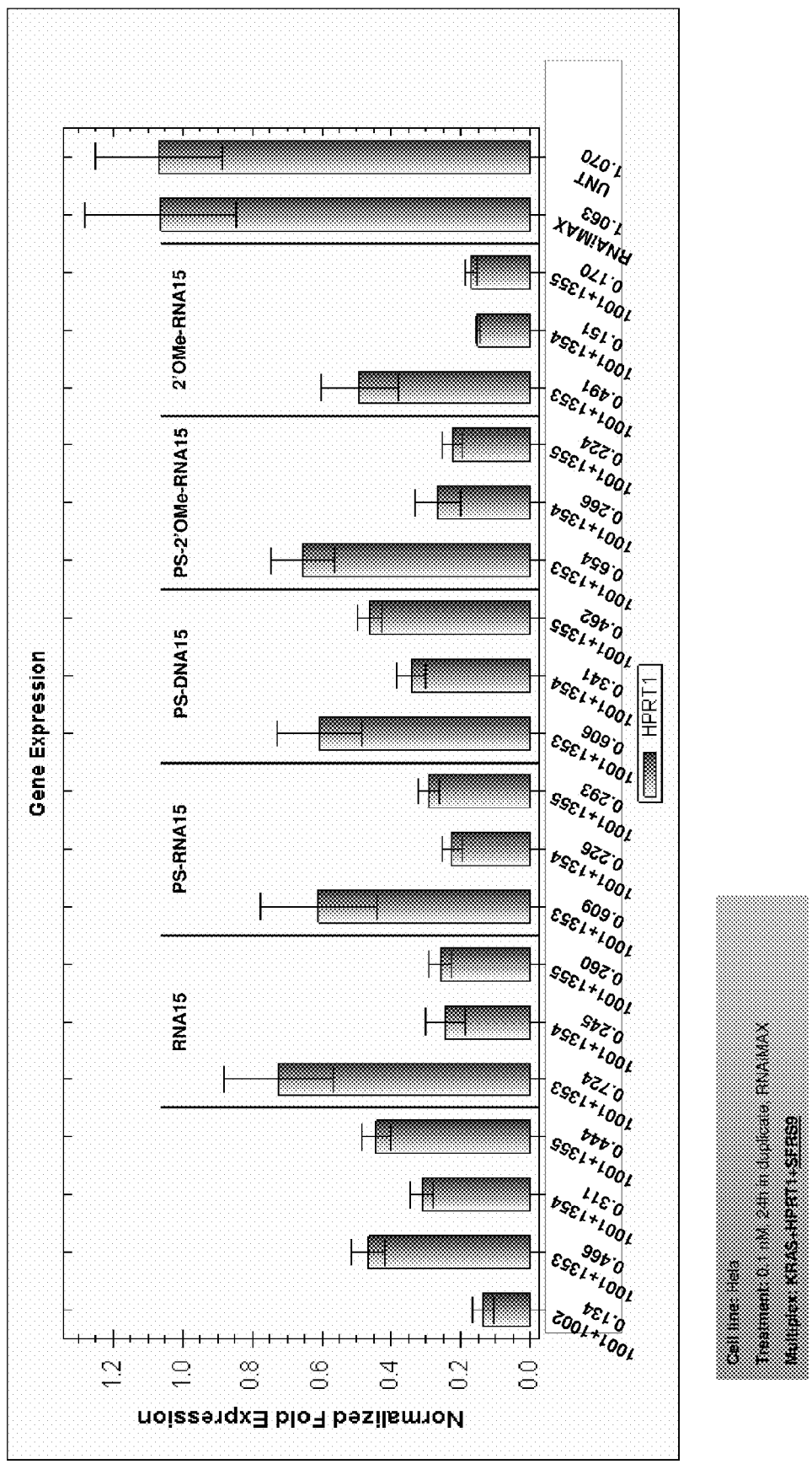
Figure 13. 15bp length ssDNA/RNA extensions + 15bp oligos that complement the extensions HPRT1

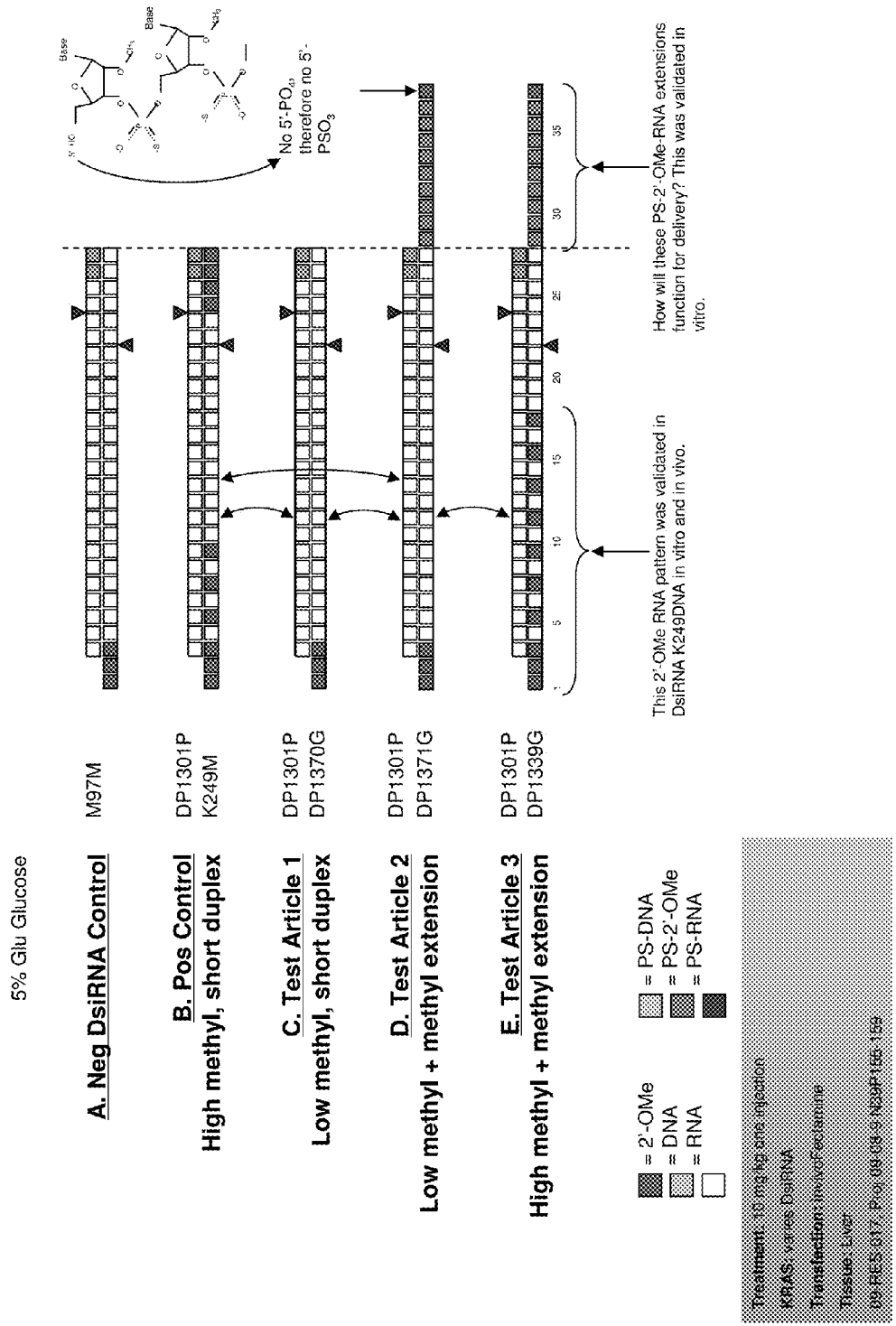
Figure 14. PS-2'OMe DsiRNA in vivo experiment
(09-RES-019, ver 12.1, Liver)

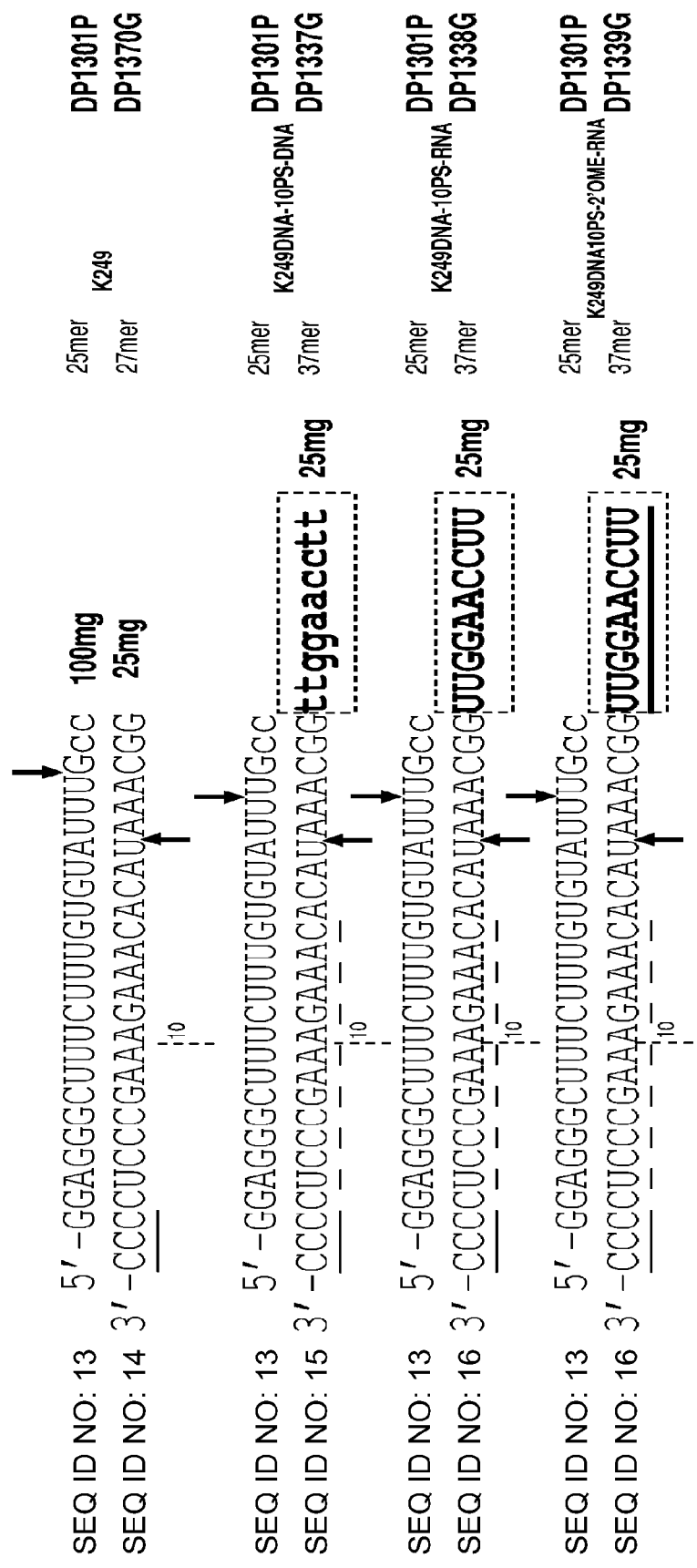

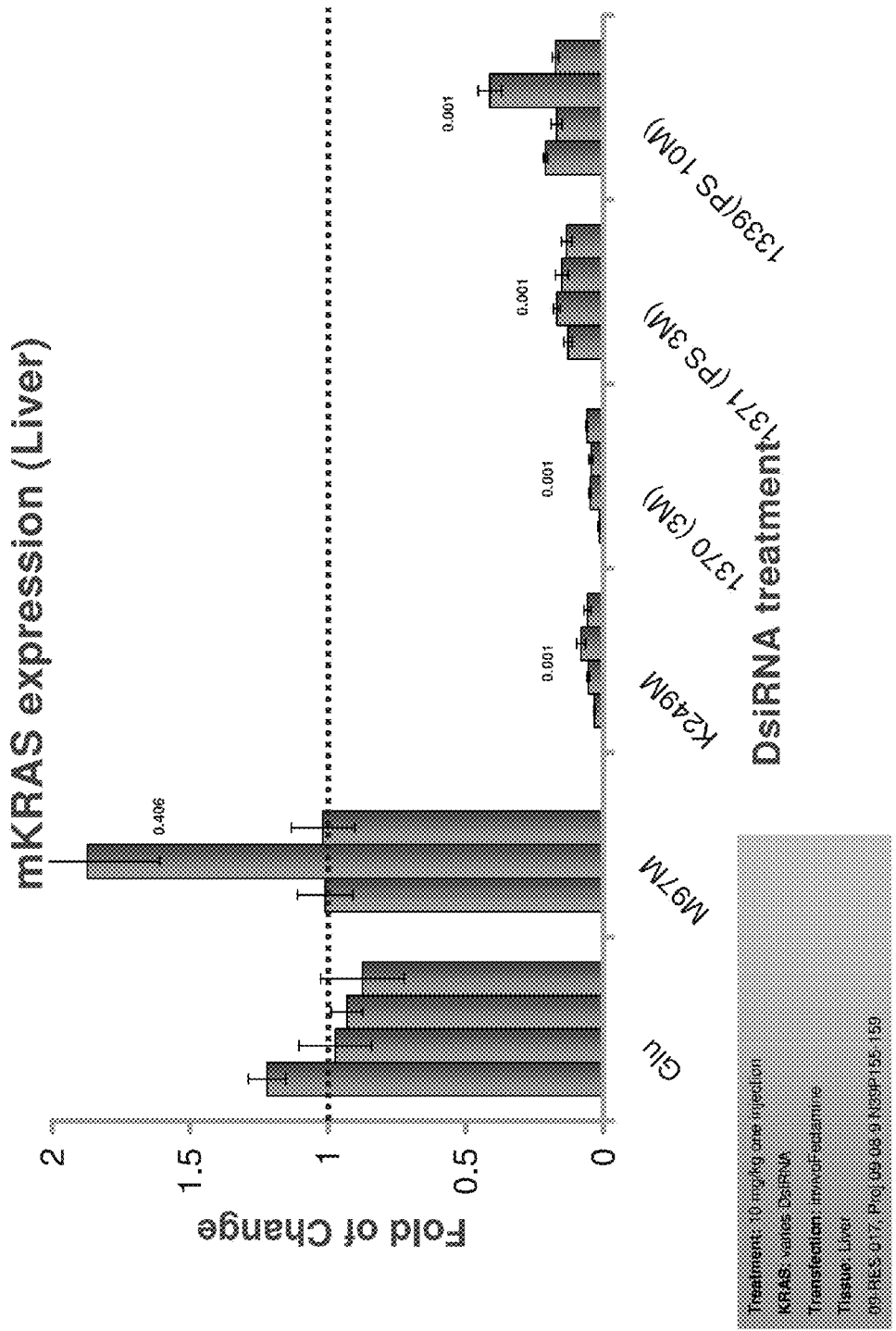

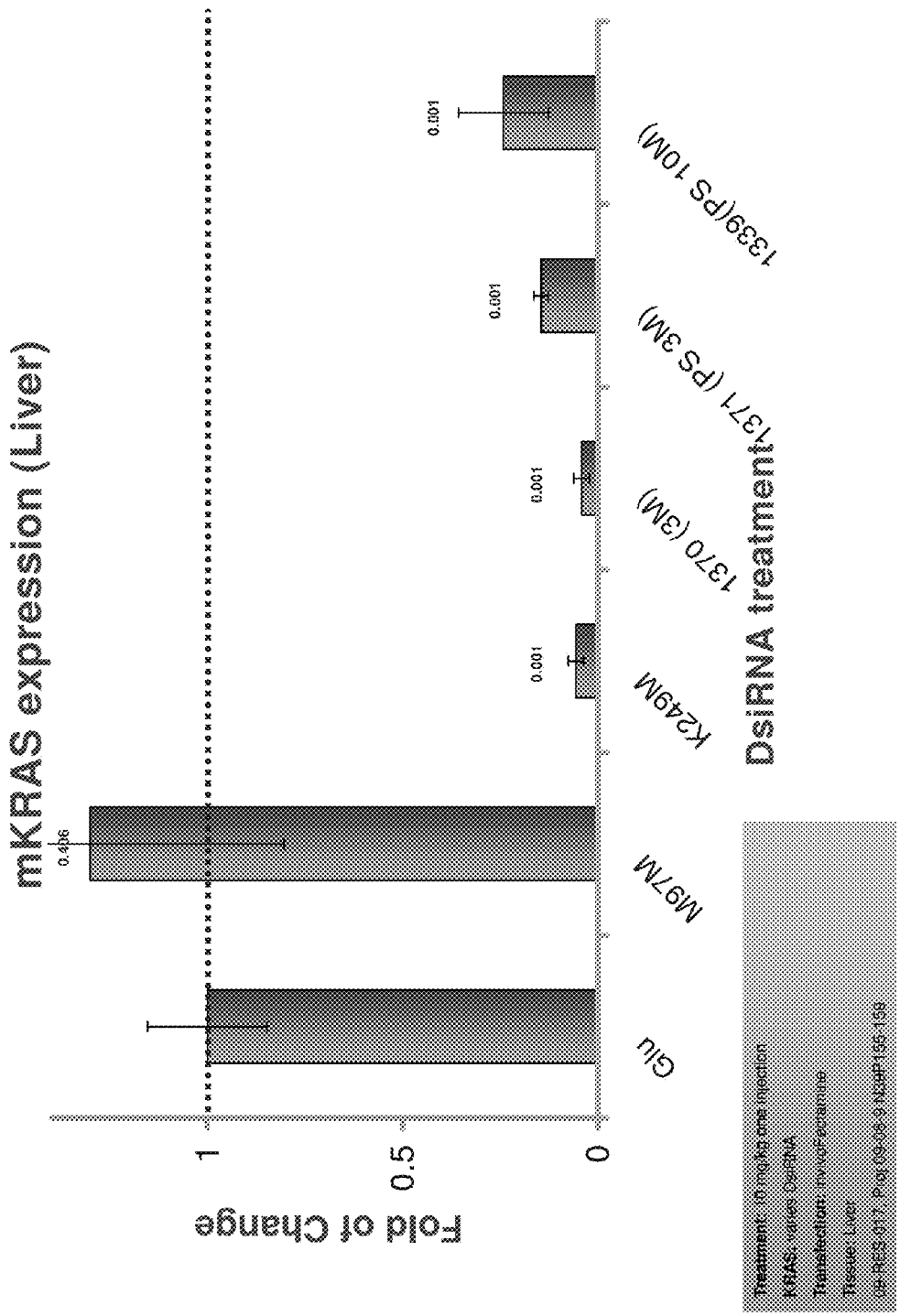
Figure 17. PS-2'OMe DsiRNA in vivo experiment (09-RES-019, ver 12.1, Liver)

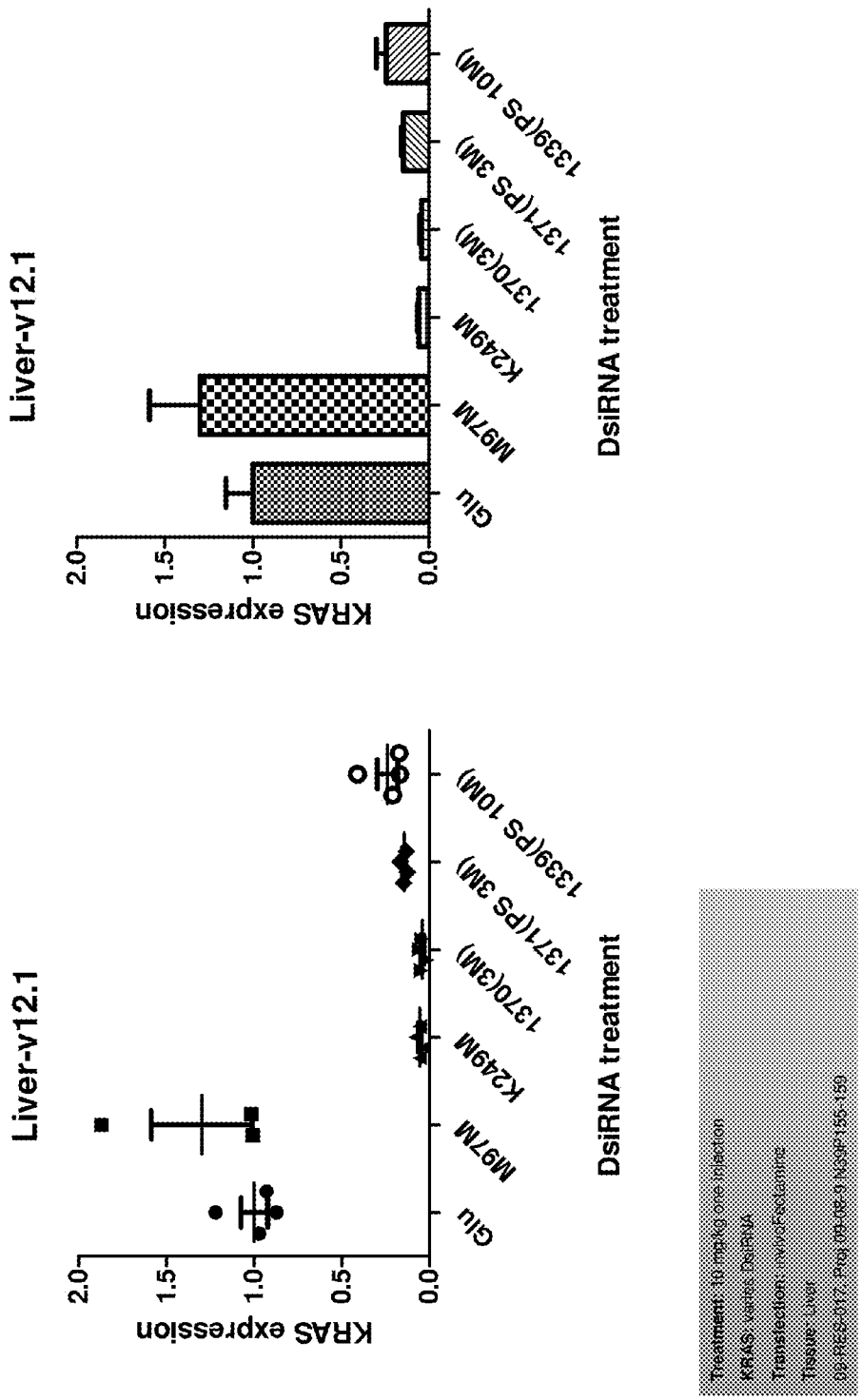

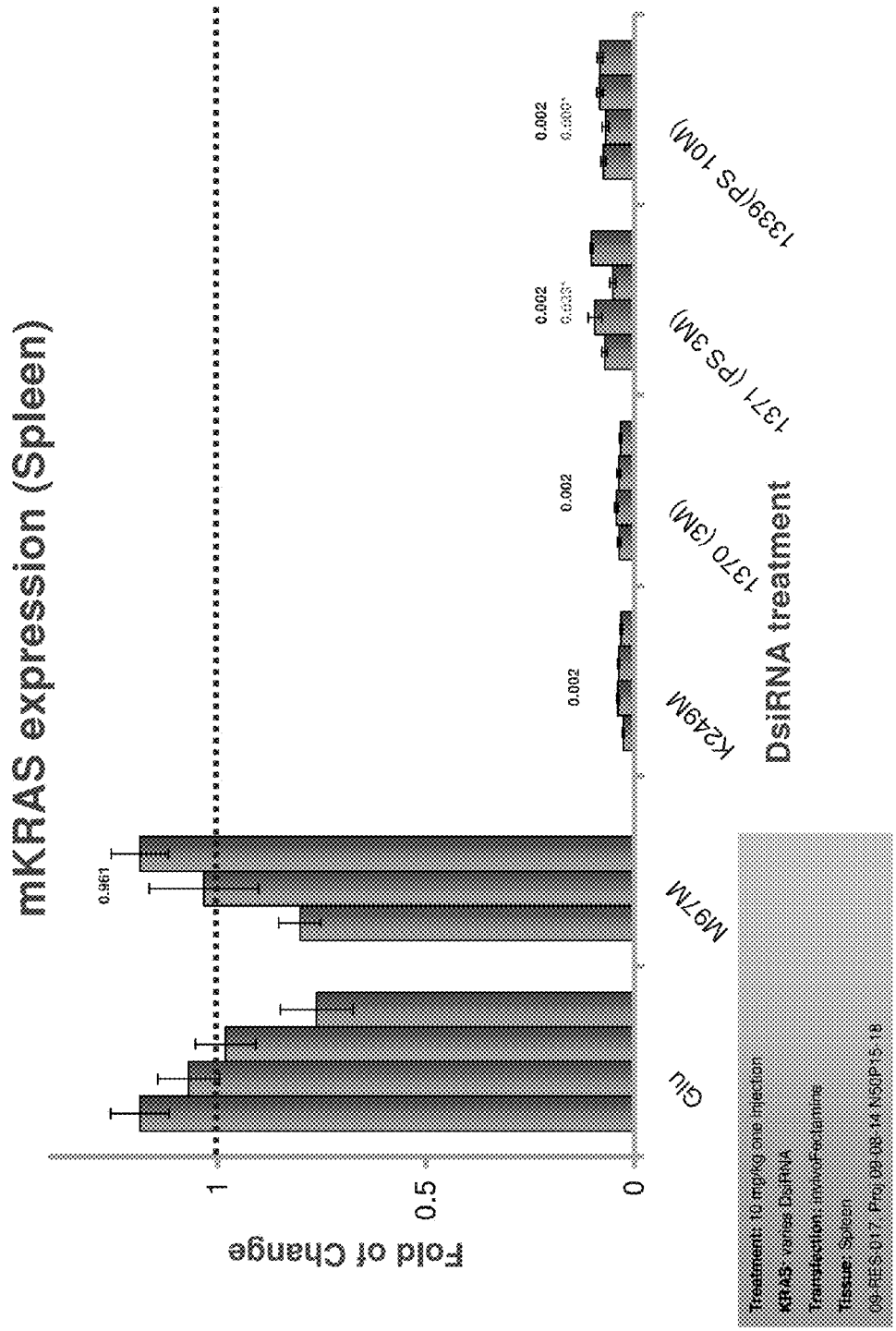

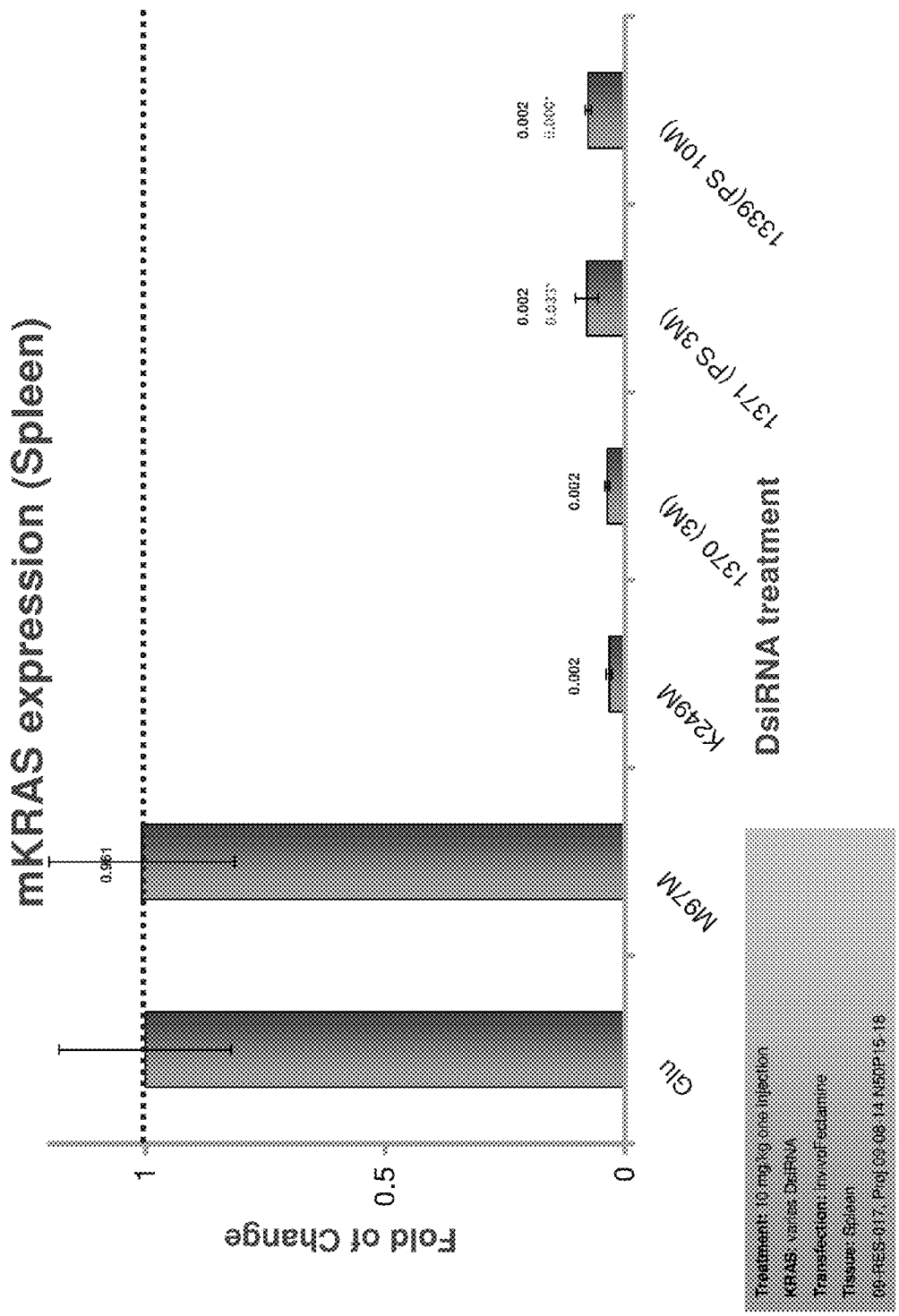

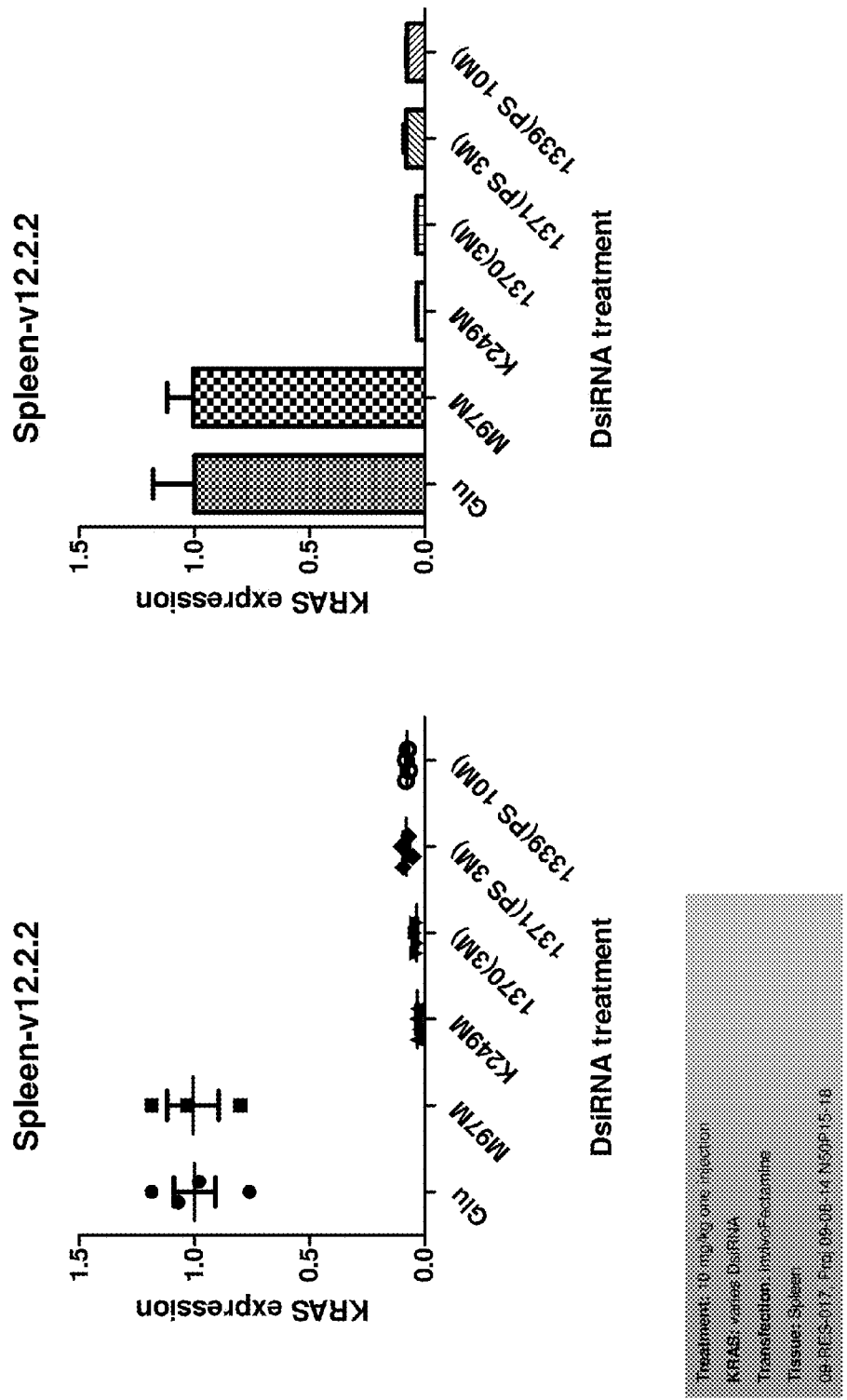

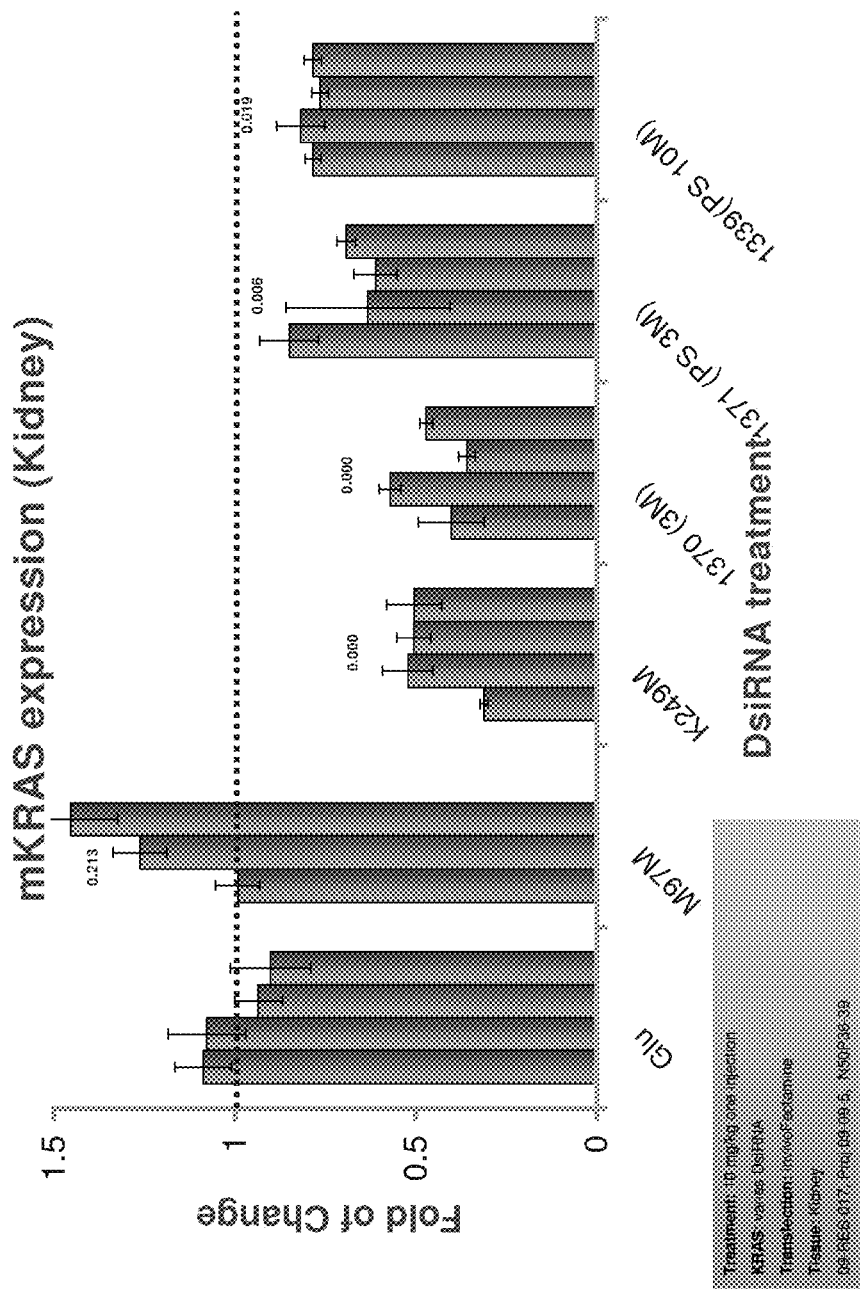
Figure 22. PS-2'OMe DsiRNA in vivo experiment (09-RES-019, ver 12.3, Kidney)

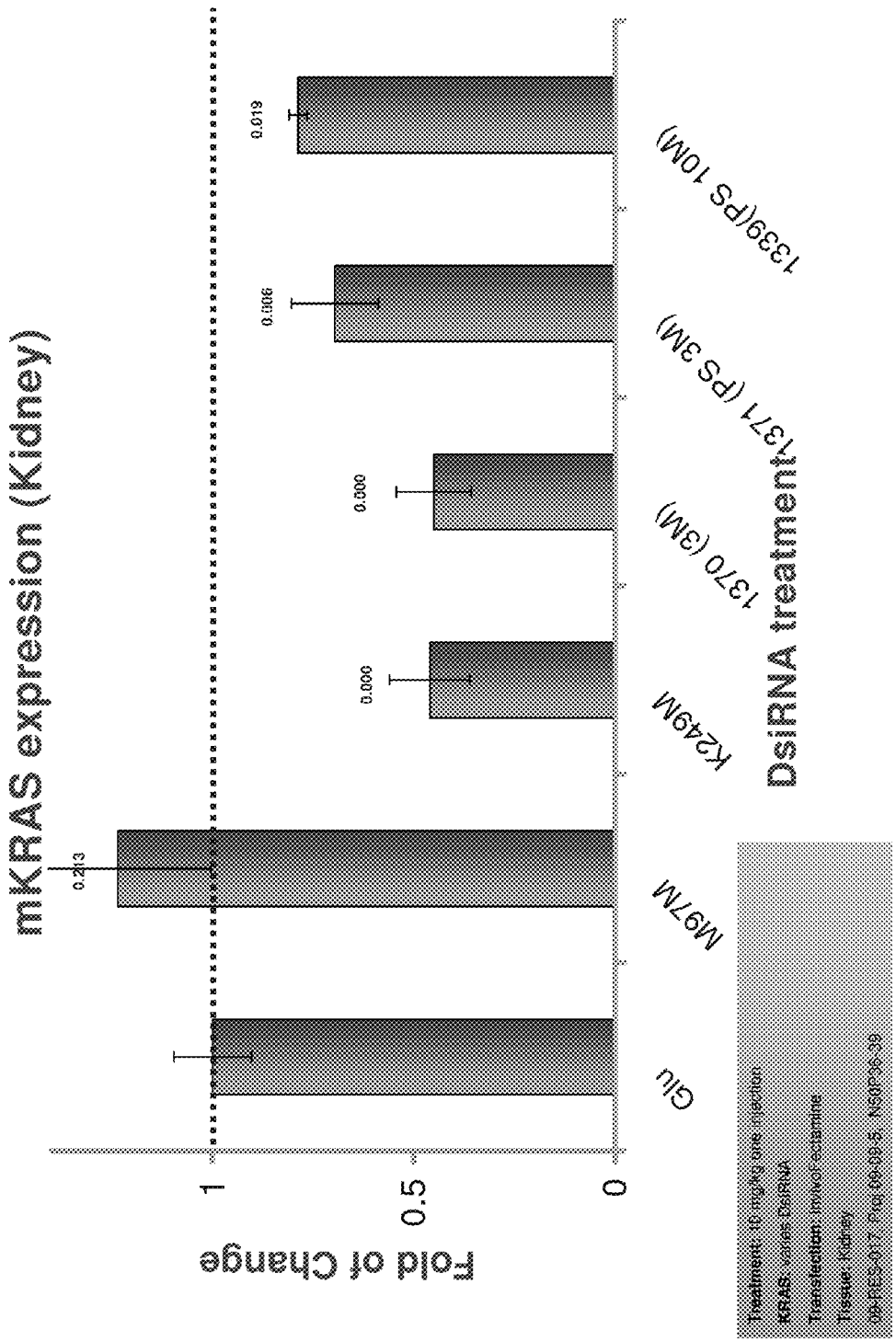

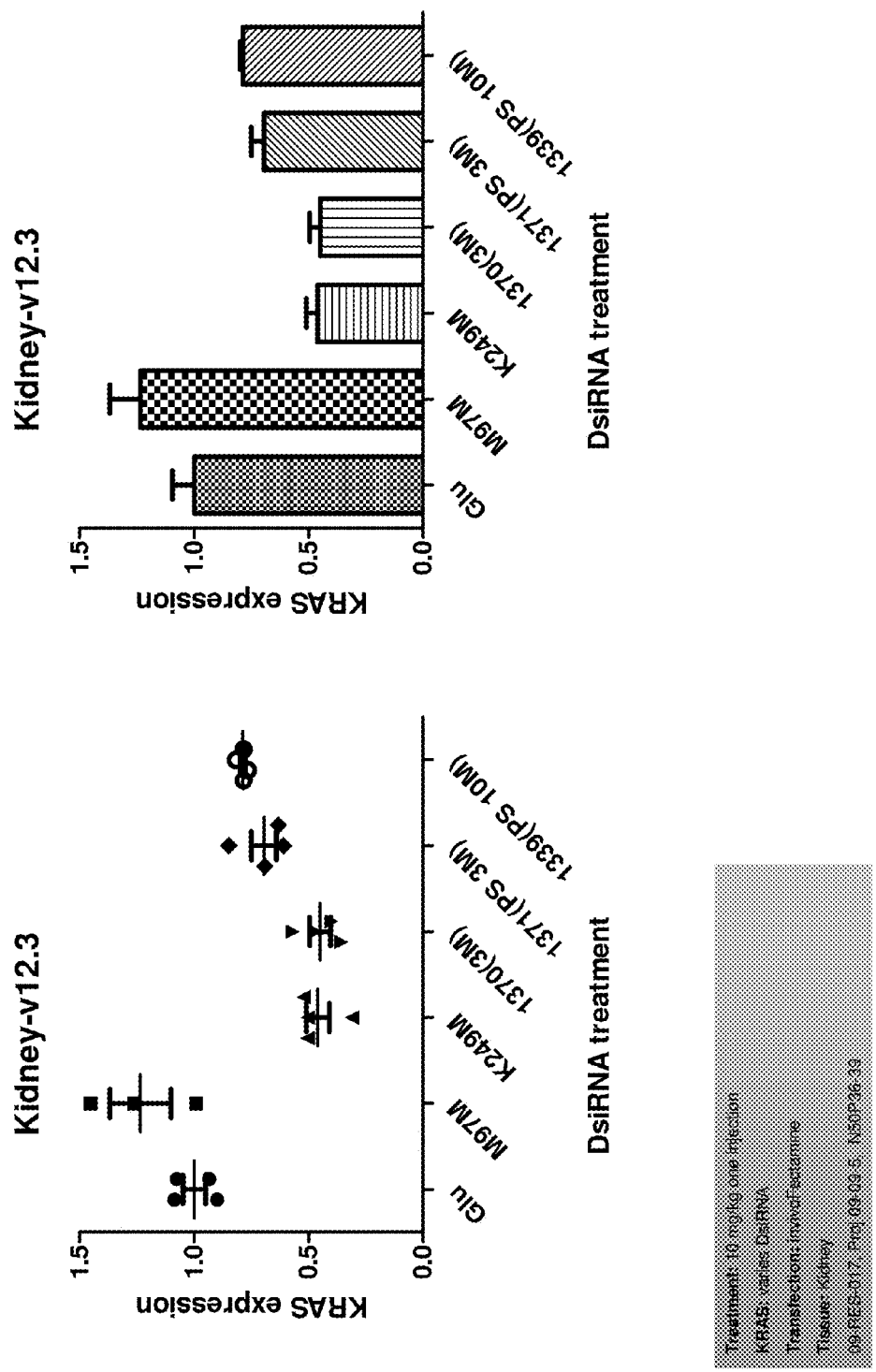
Figure 24. PS-2'OMe DsiRNA in vivo experiment (09-RES-019, ver 12.3, Kidney)

```
                         SEQUENCE LISTING

<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gactttgctt tccttggtca g                                            21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcttatatc caacacttcg tggg                                         24

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
atggtcaagg tcgcaagctt gctggt                                       26

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtgcagaag gatggagt                                                18

<210> SEQ ID NO 5
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ctggtgcttc tctcaggata                                           20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 6
tggaatatgc cctgcgtaaa ctgga                                     25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
caaactttgc tttccctggt                                           20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
caacaaagtc tggcctgtat c                                         21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 9
tggttaaggt tgcaagcttg ctggtg                                    26

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ctttgtggat gagtacgacc                                           20

<210> SEQ ID NO 11
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cactgtactc ctcttgacct                                                  20

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
acgatagagg actcctacag gaaacaagt                                        29

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ggagggcuuu cuuuguguau uugcc                                            25

<210> SEQ ID NO 14
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ggcaaauaca caaagaaagc ccucccc                                          27

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ttccaaggtt ggcaaauaca caaagaaagc ccucccc                               37

<210> SEQ ID NO 16
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuccaagguu ggcaaauaca caaagaaagc ccucccc                               37
```

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
caaggttcca aggttggcaa auacacaaag aaagcccucc cc            42

<210> SEQ ID NO 18
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
caagguucca agguuggcaa auacacaaag aaagcccucc cc            42

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
gccagacuuu guuggauuug aaatt                               25

<210> SEQ ID NO 20
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aauuucaaau ccaacaaagu cuggcuu                             27

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ttccaaggtt aauuucaaau ccaacaaagu cuggcuu                  37

<210> SEQ ID NO 22
<211> LENGTH: 37
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 22
uuccaagguu aauuucaaau ccaacaaagu cuggcuu                              37

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
caaggttcca aggttaauuu caaauccaac aaagucuggc uu                        42

<210> SEQ ID NO 24
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
caagguucca agguuaauuu caaauccaac aaagucuggc uu                        42

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aaccuuggaa ccuug                                                      15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaccttggaa ccttg                                                      15

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caagguucca agguu                                                      15

<210> SEQ ID NO 28
<211> LENGTH: 10
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 28
aaccuuggaa                                                               10

<210> SEQ ID NO 29
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuccaagguu                                                               10
```

SINGLE STRANDED EXTENDED DICER SUBSTRATE AGENTS AND METHODS FOR THE SPECIFIC INHIBITION OF GENE EXPRESSION

CROSS-REFERENCE TO RELATED APPLICATIONS

The present application is a divisional of U.S. patent application Ser. No. 12/824,011, filed on Jun. 25, 2010, which is a continuation-in-part of U.S. patent application Ser. No. 12/704,256, filed on Feb. 11, 2010, which claims priority under 35 U.S.C. §119(e) to U.S. patent application No. 61/151,841, filed Feb. 11, 2009, and U.S. Ser. No. 12/824,011 is also a continuation-in-part of U.S. patent application Ser. No. 12/642,371, filed Dec. 18, 2009, which is related to and claims priority under 35 U.S.C. §119(e) to the following applications: U.S. provisional patent application No. 61/138,946, filed Dec. 18, 2008; U.S. provisional patent application No. 61/166,227, filed Apr. 2, 2009; U.S. provisional patent application No. 61/173,505, filed Apr. 28, 2009; U.S. provisional patent application No. 61/173,514, filed Apr. 28, 2009; U.S. provisional patent application No. 61/173,521, filed Apr. 28, 2009; U.S. provisional patent application No. 61/173,525, filed Apr. 28, 2009; U.S. provisional patent application No. 61/173,532, filed Apr. 28, 2009; U.S. provisional patent application No. 61/173,538, filed Apr. 28, 2009; U.S. provisional patent application No. 61/173,544, filed Apr. 28, 2009; U.S. provisional patent application No. 61/173,549, filed Apr. 28, 2009; U.S. provisional patent application No. 61/173,554, filed Apr. 28, 2009; U.S. provisional patent application No. 61/173,556, filed Apr. 28, 2009; U.S. provisional patent application No. 61/173,558, filed Apr. 28, 2009; and U.S. provisional patent application No. 61/173,563, filed Apr. 28, 2009. The entire teachings of the above applications are incorporated herein by reference.

BACKGROUND OF THE INVENTION

Double-stranded RNA (dsRNA) agents possessing strand lengths of 25 to 35 nucleotides have been described as effective inhibitors of target gene expression in mammalian cells (Rossi et al., U.S. Patent Publication Nos. 2005/0244858 and 2005/0277610). dsRNA agents of such length are believed to be processed by the Dicer enzyme of the RNA interference (RNAi) pathway, leading such agents to be termed "Dicer substrate siRNA" ("DsiRNA") agents. Certain modified structures of DsiRNA agents were previously described (Rossi et al., U.S. Patent Publication No. 2007/0265220).

BRIEF SUMMARY OF THE INVENTION

The present invention is based, at least in part, upon the surprising discovery that double stranded nucleic acid agents having strand lengths in the range of 25-30 nucleotides in length that possess a single stranded nucleotide region either at the 5' terminus of the antisense strand, at the 3' terminus of the sense strand, or at the 5' terminus of the sense strand are effective RNA interference agents. Inclusion of one or more modified nucleotides and/or phosphate backbone modifications within the single stranded region of a single stranded extended DsiRNA can impart certain advantages to such a modified DsiRNA molecule, including, e.g., enhanced efficacy (including enhanced potency and/or improved duration of effect), display of a recognition domain for DNA-binding molecules, and other attributes associated with a single stranded nucleotide region Thus, in certain aspects, the instant invention provides RNA inhibitory agents possessing enhanced efficacies at greater length (via more precise direction of the location of Dicer cleavage events) than previously described RNA inhibitory agents, thereby allowing for generation of dsRNA-containing agents possessing enhanced efficacy, delivery, pharmacokinetic, pharmacodynamic and biodistribution attributes, as well as improved ability, e.g., to be successfully formulated, to be targeted to a specific receptor, to be attached to an active drug molecule and/or payload, to be attached to another active nucleic acid molecule, to be attached to a detection molecule, to possess (e.g., multiple) stabilizing modifications, etc.

In one aspect, the invention provides an isolated double stranded nucleic acid having a first oligonucleotide strand having a 5' terminus and a 3' terminus and a second oligonucleotide strand having a 5' terminus and a 3' terminus, where each 5' terminus has a 5' terminal nucleotide and each 3' terminus has a 3' terminal nucleotide, where the first strand is 25-30 nucleotide residues in length, where starting from the 5' terminal nucleotide (position 1) positions 1 to 23 of the first strand include at least 8 ribonucleotides; the second strand is 36-66 nucleotide residues in length and, starting from the 3' terminal nucleotide, includes at least 8 ribonucleotides in the positions paired with positions 1-23 of the first strand to form a duplex; where at least the 3' terminal nucleotide, and up to 6 consecutive nucleotides 3' terminal of the second strand, is unpaired with the first strand, forming a 3' single stranded overhang of 1-6 nucleotides; where at least 10 consecutive nucleotides and at most 30 consecutive nucleotides, not including the unpaired 3' terminal nucleotides of the second strand are unpaired with the first strand, thereby forming in the second strand a 10-30 nucleotide single stranded 5' overhang; where the 5' terminal and the 3' terminal nucleotides of the first strand is each paired with a corresponding nucleotide of the second strand, the corresponding second strand nucleotide being consecutive to the second strand 3' single stranded overhang and the second strand 5' overhang, respectively, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell.

In another aspect the invention provides an isolated double stranded nucleic acid having a first oligonucleotide strand having a 5' terminus and a 3' terminus and a second oligonucleotide strand having a 5' terminus and a 3' terminus, where each 5' terminus has a 5' terminal nucleotide and each 3' terminus has a 3' terminal nucleotide, where the first strand is 35-60 nucleotide residues in length, where starting from the 5' terminal nucleotide (position 1) positions 1 to 28 of the first strand include at least 8 ribonucleotides; the second strand is 26-36 nucleotide residues in length and, starting from the 3' terminal nucleotide, includes at least 8 ribonucleotides in the positions paired with positions 1-23 of the first strand to form a duplex; where at least the 3' terminal nucleotide, and up to 6 consecutive 3' terminal nucleotides, of the second strand is unpaired with the first strand, forming a 3' single stranded overhang of 1-6 nucleotides; where at least 10 consecutive nucleotides and at most 30 consecutive nucleotides, including the 3' terminal nucleotide of the first strand are unpaired with the 5' terminus of the second strand, thereby forming a 10-30 nucleotide single stranded 3' overhang; where the 5' terminal nucleotide of the first strand is paired with the nucleotide of the second strand consecutive to the second strand 3' single stranded overhang, and the 5' terminal nucleotide of the second strand is paired with the nucleotide of the first strand consecutive to the first strand 3' overhang, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell.

In another aspect the invention provides an isolated double stranded nucleic acid having a first oligonucleotide strand having a 5' terminus and a 3' terminus and a second oligonucleotide strand having a 5' terminus and a 3' terminus, where each 5' terminus has a 5' terminal nucleotide and each 3' terminus has a 3' terminal nucleotide, where the first strand is 35-66 nucleotide residues in length, where starting from the 5' terminal nucleotide consecutive to the first strand 5' single stranded overhang (position $1^F$) positions $1^F$ to $28^F$ of the first strand include at least 8 ribonucleotides; the second strand is 25-36 nucleotide residues in length and, includes at least 8 ribonucleotides in the positions paired with positions $1^F$-$23^F$ of the first strand to form a duplex; where the 3' terminal nucleotide of the first strand and the 5' terminal nucleotide of the second strand form a blunt end; where at least 10 consecutive nucleotides and at most 30 consecutive nucleotides, including the 5' terminal nucleotide of the first strand are unpaired with the 3' terminus of the second strand, thereby forming a 10-30 nucleotide single stranded 5' overhang; where the 3' terminal nucleotide of the second strand is paired with the nucleotide of the first strand consecutive to the first strand 5' single stranded overhang, and the 3' terminal nucleotide of the first strand is paired with the 5' terminal nucleotide of the second strand, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell.

In an additional aspect, the invention provides an isolated double stranded nucleic acid as shown in any one of FIG. 1-6, 8, 11, 14, or 15.

In one aspect, the invention provides a method for reducing expression of a target gene in a cell, involving contacting a cell with an isolated double stranded nucleic acid as described herein in an amount effective to reduce expression of a target gene in a cell in comparison to a reference dsRNA.

In another aspect, the invention provides a method for reducing expression of a target gene in an animal, involving treating an animal with an isolated double stranded nucleic acid as described herein in an amount effective to reduce expression of a target gene in a cell of the animal in comparison to a reference dsRNA.

In one aspect, the invention provides a pharmaceutical composition for reducing expression of a target gene in a cell of a subject containing an isolated double stranded nucleic acid as described herein in an amount effective to reduce expression of a target gene in a cell in comparison to a reference dsRNA and a pharmaceutically acceptable carrier.

In yet another aspect, the invention provides a method of synthesizing a double stranded nucleic acid as described herein, involving chemically or enzymatically synthesizing the double stranded nucleic acid.

In still another aspect, the invention provides a kit containing the double stranded nucleic acid described herein and instructions for its use.

In various embodiments of any of the above aspects, the isolated double stranded nucleic acid of claim 1, where at least one nucleotide of the first strand between and including the first strand positions 24 to the 3' terminal nucleotide residue of the first strand is a deoxyribonucleotide. In various embodiments of any of the above aspects, the isolated double stranded nucleic acid of claim 1, where at least 10 consecutive nucleotides and at most 15 consecutive nucleotides, not including the unpaired 3' terminal nucleotides of the second strand are unpaired with the first strand, thereby forming in the second strand a 10-15 nucleotide single stranded 5' overhang. In various embodiments of any of the above aspects, the first strand is up to 30 nucleotides in length, and the nucleotides of the first strand 3' to position 23 of the first strand includes two, three, four, five, and six deoxynucleotide residues from position 24 to the 3' terminal nucleotide residue of the first strand that base pair with a nucleotide of the second strand.

In various embodiments of any of the above aspects, the 5' single stranded overhang of the second strand is 10, 11, 12, 13, 14, 15, 16, 17, 18, 19, 20, 21, 22, 23, 24, 25, 26, 27, 28, 29, or 30 nucleotides in length. In various embodiments of any of the above aspects, the nucleotides of the second strand 5' overhang include a phosphate backbone modification. In various embodiments of any of the above aspects, the phosphate backbone modification is a phosphonate, a phosphorothioate, a phosphotriester, and a methylphosphonate, a locked nucleic acid, a morpholino, or a bicyclic furanose analog.

In various embodiments of any of the above aspects, the second strand starting from the 5' terminal nucleotide residue of the second strand (position $1^B$), includes a phosphorothioate backbone modification between the nucleotides from position $2^B$ to the 5' residue of the second strand that corresponds to the 3' terminal residue of the first strand. In various embodiments of any of the above aspects, the second strand 5' overhang includes a ribonucleotide or deoxyribonucleotide. In various embodiments of any of the above aspects, all nucleotides of the second strand 5' overhang are deoxyribonucleotides. In various embodiments of any of the above aspects, all nucleotides of the second strand 5' overhang are ribonucleotides. In various embodiments of any of the above aspects, the nucleotides of the second strand 5' overhang include a modified nucleotide. In various embodiments of any of the above aspects, the modified nucleotide residue is 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)$_2$—O-2'-bridge, 2'-LNA, 2'-amino or 2'-O—(N-methlycarbamate). In various embodiments of any of the above aspects, the modified nucleotide of the second strand 5' overhang is a 2'-O-methyl ribonucleotide. In various embodiments of any of the above aspects, the 5' terminal nucleotide residue of the second strand is a 2'-O-methyl ribonucleotide.

In various embodiments of any of the above aspects, the isolated double stranded nucleic acid, further includes a third oligonucleotide strand having a 5' terminus and a 3' terminus, where the third strand is 10-30 nucleotide residues in length; where at least 10 consecutive nucleotides and at most 30 consecutive nucleotides of the third strand are paired with the 5' terminus of the second strand. In various embodiments of any of the above aspects, the third strand includes a ribonucleotide or deoxyribonucleotide. In various embodiments of any of the above aspects, all nucleotides of the second strand 5' overhang are ribonucleotides. In various embodiments of any of the above aspects, the nucleotides of the third strand include a modified nucleotide. In various embodiments of any of the above aspects, the modified nucleotide residue is 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)$_2$-O-2'-bridge, 2'-LNA, 2'-amino and 2'-O—(N- methylcarbamate). In various embodiments of any of the above aspects, the modified nucleotide of the third strand is a 2'-O-methyl ribonucleotide. In various embodiments of any of the above aspects, all nucleotides of the third strand are modified nucleotides or 2'-O-methyl ribonucleotides. In various embodiments of any of the above aspects, the third strand includes a phosphate backbone modification. In various embodiments of any of the above aspects, the phosphate backbone modification is a phosphonate, a phosphorothioate, a phosphotriester, and a methylphosphonate, a locked nucleic acid, a morpholino, or a bicyclic furanose analog. In various embodiments of any of the above aspects, the third strand starting from the 5' terminal nucleotide residue of the third strand (position $1^C$), includes a phosphorothioate backbone modification between the nucleotides at positions $1^C$ and $2^C$.

In various embodiments of any of the above aspects, at least 10 consecutive nucleotides and at most 15 consecutive nucleotides, including the 3' terminal nucleotide of the first strand are unpaired with the 5' terminus of the second strand, thereby forming a 10-15 nucleotide single stranded 3' overhang. In various embodiments of any of the above aspects, the first strand is up to 66 nucleotides in length, and the nucleotides of the first strand 3' to position 23 of the first strand includes deoxyribonucleotides two, three, four, five, or six deoxynucleotide residues from positions 24 to the 3' terminal nucleotide residue of the first strand. In various embodiments of any of the above aspects, the deoxyribonucleotides are consecutive deoxyribonucleotides. In various embodiments of any of the above aspects, two or more consecutive nucleotide residues of positions 24 to 30 of the first strand are deoxyribonucleotides that base pair with nucleotides of the second strand. In various embodiments of any of the above aspects, the first strand is up to 66 nucleotides in length and includes a pair of deoxyribonucleotides at positions 24 and 25, positions 25 and 26, positions 26 and 27, positions 27 and 28, positions 28 and 29, or positions 29 and 30, where the first pair of deoxyribonucleotides is base paired with a corresponding pair of nucleotides of the second strand.

In various embodiments of any of the above aspects, the first strand 3' overhang is 10, 11, 12, 13, 14, 15, 16, 17, 18, 19, 20, 21, 22, 23, 24, 25, 26, 27, 28, 29 or 30 nucleotides in length. In various embodiments of any of the above aspects, the first strand 3' overhang includes a ribonucleotide or deoxyribonucleotide. In various embodiments of any of the above aspects, all nucleotides of the first strand 3' overhang are deoxyribonucleotides. In various embodiments of any of the above aspects, the nucleotides of the first strand 3' overhang include a phosphate backbone modification. In various embodiments of any of the above aspects, the phosphate backbone modification is a phosphonate, a phosphorothioate, a phosphotriester, a methylphosphonate, a locked nucleic acid, a morpholino or a bicyclic furanose analog.

In various embodiments of any of the above aspects, the first strand starting from the 3' terminal nucleotide residue of the first strand (position $1^D$), includes a methylphosphonate backbone modification between the nucleotides from position $1^D$ to 5' residue of the first strand that is consecutive to the first strand 3' overhang. In various embodiments of any of the above aspects, the first strand starting from the 3' terminal nucleotide residue of the first strand (position $1^D$), includes a methylphosphonate backbone modification between the nucleotides from position $2^D$ to 5' residue of the first strand that is consecutive to the first strand 3' overhang. In various embodiments of any of the above aspects, the 3' terminal nucleotide of the first strand is a ribonucleotide.

In various embodiments of any of the above aspects, the nucleotides of the first strand 3' overhang include a modified nucleotide. In various embodiments of any of the above aspects, the modified nucleotide residue is 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)$_2$-O-2'-bridge, 2'-LNA, 2'-amino or 2'-O—(N-methylcarbamate). In various embodiments of any of the above aspects, the modified nucleotide of the first strand 3' overhang is a 2'-O-methyl ribonucleotide.

In various embodiments of any of the above aspects, the first strand or the second strand at least 8 ribonucleotides are contiguous. In various embodiments of any of the above aspects, the first strand includes at least 9, 10, 11, 12 and up to 25 ribonucleotides. In various embodiments of any of the above aspects, the ribonucleotides are contiguous. In various embodiments of any of the above aspects, at least one nucleotide of the second strand between and including second strand nucleotides corresponding to and thus base paired with first strand positions 24 to the 3' terminal nucleotide residue of the first strand is a ribonucleotide.

In various embodiments of any of the above aspects, the substantially duplexed region between the first and second strands has a fully duplexed region having no unpaired bases between the 5' terminal and 3' terminal nucleotides of first strand that are paired with corresponding nucleotides of the second strand. In various embodiments of any of the above aspects, the substantially duplexed region has, between the 5' terminal and 3' terminal nucleotides of first strand that are paired with corresponding nucleotides of the second strand; 1 unpaired base pair; 2 unpaired base pairs, 3 unpaired base pairs, 4 unpaired base pairs, and 5 unpaired base pairs. In various embodiments of any of the above aspects, the unpaired base pairs are consecutive or non-consecutive.

In various embodiments of any of the above aspects, the deoxyribonucleotides of the first strand that base pair with a nucleotide of the second strand are consecutive deoxyribonucleotides. In various embodiments of any of the above aspects, at least one nucleotide of the first strand between and including the first strand positions 24 to the 3' terminal nucleotide residue of the first strand is a deoxyribonucleotide that base pairs with the second strand. In various embodiments of any of the above aspects, two or more consecutive nucleotide residues of positions 24 to 30 of the first strand are deoxyribonucleotides that base pair with nucleotides of the second strand. In various embodiments of any of the above aspects, the first strand is up to 30 nucleotides in length and includes a pair of deoxyribonucleotides at positions 24 and 25, positions 25 and 26, positions 26 and 27, positions 27 and 28, positions 28 and 29, or positions 29 and 30, where the first strand pair of deoxyribonucleotides is base paired with a corresponding pair of nucleotides of the second strand.

In various embodiments of any of the above aspects, the 8 or more ribonucleotides of positions 1 to 28 of the first strand are consecutive ribonucleotides. In various embodiments of any of the above aspects, each nucleotide residue of positions 1 to 28 of the first oligonucleotide strand is a ribonucleotide that base pairs with a nucleotide of the second strand.

In various embodiments of any of the above aspects, the 3' single stranded overhang of the second strand is a length 1 to 4 nucleotides, 1 to 3 nucleotides, 1 to 2 nucleotides, or 2 nucleotides in length. In various embodiments of any of the above aspects, the nucleotides of the second strand 3' overhang includes a modified nucleotide. In various embodiments of any of the above aspects, the modified nucleotide residue is a 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino or 2'-O—(N-methylcarbamate). In various embodiments of any of the above aspects, the modified nucleotide of the second strand 3' overhang is a 2'-O-methyl ribonucleotide.

In various embodiments of any of the above aspects, all nucleotides of the second strand 3' overhang are modified nucleotides. In various embodiments of any of the above aspects, the second strand 3' overhang is two nucleotides in length and where the modified nucleotide of the second strand 3' overhang is a 2'-O-methyl modified ribonucleotide. In various embodiments of any of the above aspects, one or both of the first and second strands has a 5' phosphate.

In various embodiments of any of the above aspects, the second strand, starting from the nucleotide residue of the second strand that corresponds to the 5' terminal nucleotide residue of the first oligonucleotide strand (position $1^A$), includes unmodified nucleotide residues at all positions from position $16^A$ to the 5' residue of the second strand that corresponds to the 3' terminal residue of the first strand. In various embodiments of any of the above aspects, starting from the first nucleotide (position $1^A$) at the 3' terminus of the second strand, positions $1^A$, $2^A$, and $3^A$ from the 3' terminus of the second strand are modified nucleotides. In various embodiments of any of the above aspects, the second oligonucleotide strand, starting from the nucleotide residue of the second strand that corresponds to the 5' terminal nucleotide residue of the first oligonucleotide strand (position $1^A$), includes alternating modified and unmodified nucleotide residues from position $1^A$ to position $15^A$.

In various embodiments of any of the above aspects, a nucleotide of the second or first oligonucleotide strand is substituted with a modified nucleotide that directs the orientation of Dicer cleavage. In various embodiments of any of the above aspects, the first strand has a nucleotide sequence that is at least 80%, 90%, 95% or 100% complementary to the second strand nucleotide sequence. In various embodiments of any of the above aspects, the double stranded nucleic acid is cleaved endogenously in a mammalian cell by Dicer. In various embodiments of any of the above aspects, the double stranded nucleic acid is cleaved endogenously in a mammalian cell to produce a double-stranded nucleic acid of 19-23 nucleotides in length that reduces target gene expression. In various embodiments of any of the above aspects, the double stranded nucleic acid reduces target gene expression in a mammalian cell in vitro by an amount (expressed by %) at least 10%, at least 50% or at least 80-90%. In various embodiments of any of the above aspects, the double stranded nucleic acid, when introduced into a mammalian cell, reduces target gene expression in comparison to a reference dsRNA that does not possess a deoxyribonucleotide-deoxyribonucleotide base pair. In various embodiments of any of the above aspects, where the double stranded nucleic acid, when introduced into a mammalian cell, reduces target gene expression by at least 70% when transfected into the cell at a concentration of 1 nM or less, 200 pM or less, 100 pM or less, 50 pM or less, 20 pM or less or 10 pM or less. In various embodiments of any of the above aspects, at least 50% of the ribonucleotide residues of the double stranded nucleic acid are unmodified ribonucleotides. In various embodiments of any of the above aspects, at least 50% of the ribonucleotide residues of the second strand are unmodified ribonucleotides. In various embodiments of any of the above aspects, the target RNA is KRAS.

In various embodiments of any of the above aspects, double stranded nucleic acid possesses enhanced pharmacokinetics when compared to an appropriate control DsiRNA. In various embodiments of any of the above aspects, the double stranded nucleic acid possesses enhanced pharmacodynamics when compared to an appropriate control DsiRNA. In various embodiments of any of the above aspects, the double stranded nucleic acid possesses reduced toxicity when compared to an appropriate control DsiRNA. In various embodiments of any of the above aspects, the double stranded nucleic acid possesses enhanced intracellular uptake when compared to an appropriate control DsiRNA.

BRIEF DESCRIPTION OF THE DRAWINGS

FIGS. 1A and 1B show the structure and predicted Dicer-mediated processing of exemplary single strand extended Dicer substrates. In FIG. 1A, Panel A depicts a DsiRNA without a single stranded extension. Panel B depicts a "guide strand extended" DsiRNA agent, which has a guide strand 5' overhang 1-30 nucleotides in length (15 nucleotides as shown). Panel C depicts an exemplary "guide strand extended" DsiRNA agent, which has a guide strand 5' overhang 1-30 nucleotides in length (15 nucleotides as shown), with a short oligo complementary to the single-stranded extended region ("discontinuous complement"; discontinuous 3' passenger complement as shown). Panel D depicts an exemplary "passenger strand extended" DsiRNA agent, which has a passenger strand 3' overhang 1-30 nucleotides in length (15 nucleotides as shown). Panel E depicts a "passenger strand extended" DsiRNA agent, which has a passenger strand 5' overhang 1-30 nucleotides in length (15 nucleotides as shown). In each pair of oligonucleotide strands forming a DsiRNA, the upper strand is the passenger strand and the lower strand is the guide strand. White=nucleotide (e.g., a ribonucleotide, deoxyribonucleotide, modified ribonucleotide). FIG. 1B shows nucleotide modifications and patterns of modifications of exemplary single strand extended Dicer substrates. Panel A depicts a DsiRNA without a single stranded extension. Panel B depicts a "guide strand extended" DsiRNA agent, which has a guide strand 5' overhang 1-30 nucleotides in length (15 nucleotides as shown). Panel C depicts an exemplary "guide strand extended" DsiRNA agent, which has a guide strand 5' overhang 1-30 nucleotides in length (15 nucleotides as shown), with a short oligo complementary to the single-stranded extended region ("discontinuous complement"; discontinuous 3' passenger complement as shown). Panel D depicts an exemplary "passenger strand extended" DsiRNA agent, which has a passenger strand 3' overhang 1-30 nucleotides in length (15 nucleotides as shown). In each pair of oligonucleotide strands forming a DsiRNA, the upper strand is the passenger strand and the lower strand is the guide strand. Blue=ribonucleotide or modified ribonucleotide (e.g., 2'-O-methyl ribonucleotide); Gray=deoxyribonucleotide or ribonucleotide; White=ribonucleotide; Dark Yellow=deoxyribonucleotide, ribonucleotide, or modified nucleotide (e.g., 2'-O-methyl ribonucleotide, phosphorothioate deoxyribonucleotide; methylphosphonate deoxyribonucleotide). Small arrow=Dicer cleavage site; large arrow=discontinuity. $^A$=position starting from the nucleotide residue of guide strand that is complementary to the 5' terminal nucleotide residue of passenger strand (position $1^A$); $^B$=position starting from the 5' terminal nucleotide residue of guide strand (position $1^B$); $^C$=position starting from the 5' terminal nucleotide of the short oligo complementary to single-stranded extended region (position $1^C$); $^D$=position starting from the 3' terminal nucleotide residue of passenger strand (position $1^D$); $^E$=position starting from the 3' terminal nucleotide residue of passenger strand (position $1^E$); $^F$=position starting from the 5' terminal nucleotide consecutive to the first strand 5' single stranded overhang (position $1^F$). Small arrows indicate predicted Dicer cleavage sites; a large arrow indicates a discontinuity.

FIG. 2 shows the structure and predicted Dicer-mediated processing of exemplary "guide strand extended" DsiRNA agents, which have a guide strand 5' overhang 1-30 nucleotides in length (10-15 nucleotides as shown). Blue=2'-O-methyl ribonucleotide; Gray=deoxyribonucleotide; White=ribonucleotide; Dark Yellow=phosophorothioate deoxyribonucleotide; Green=phosphorothioate 2'-O-methyl ribonucleotide; Pink=phosphorothioate ribonucleotide; Light Yellow=methylphosphonate deoxyribonucleotide. $^A$=position starting from the nucleotide residue of said second strand that is complementary to the 5' terminal nucleotide residue of passenger strand (position $1^A$); $^B$=position starting from the 5' terminal nucleotide residue of guide strand (position $1^B$). Arrows indicate predicted Dicer cleavage sites.

FIG. 3 shows the structure and predicted Dicer-mediated processing of exemplary "passenger strand extended" DsiRNA agents, which have a passenger strand 3' overhang 1-30 nucleotides in length (10-15 nucleotides, as shown). Blue=2'-O-methyl ribonucleotide; Gray=deoxyribonucleotide; White=ribonucleotide; Dark Yellow=phosophorothioate deoxyribonucleotide; Green=phosphorothioate 2'-O-methyl ribonucleotide; Pink=phosphorothioate ribonucleotide; Light Yellow=methylphosphonate deoxyribonucleotide. $^A$=position starting from the nucleotide residue of said second strand that is complementary to the 5' terminal nucleotide residue of passenger strand (position $1^A$); $^D$=position starting from the 3' terminal nucleotide residue of passenger strand. Arrows indicate predicted Dicer cleavage sites.

FIG. 4 shows the structure and predicted Dicer-mediated processing of exemplary "guide strand extended" DsiRNA agents, which have a guide strand 5' overhang 1-30 nucleotides in length. Single stranded guide extended DsiRNA agents having a passenger strand with the modification pattern depicted by DP1301P and a guide strand with a modification pattern depicted by DP1337G; DP1339G; DP1371G; and DP 1338G were generated. Additionally, the single stranded extended DsiRNA agents having a passenger strand with the modification pattern depicted in DP1301P, a guide strand with a modification pattern depicted by DP1337G; DP1339G; DP1371G; and DP1338G, and a "discontinuous 3' passenger complement" strand with a modification pattern depicted by DP1372P and DP1373P were generated. DsiRNA agents having a guide strand with the modification depicted DP1370G were used as a reference. Blue=2'-O-methyl ribonucleotide; Gray=deoxyribonucleotide; White=ribonucleotide; Dark Yellow=phosophorothioate deoxyribonucleotide; Green=phosphorothioate 2'-O-methyl ribonucleotide; Pink=phosphorothioate ribonucleotide; Light Yellow=methylphosphonate deoxyribonucleotide. Arrows indicate predicted Dicer cleavage sites.

FIG. 5 shows the structure and predicted Dicer-mediated processing of exemplary "passenger strand extended" DsiRNA agents, which have a passenger strand 3' overhang 1-30 nucleotides in length. Single stranded passenger extended DsiRNA agents having a guide strand with the modification pattern depicted by DP1XXXG and a passenger strand with a modification pattern depicted by DP1YYXP; DP1YxxP; and DP1YxxP were generated. DsiRNA agents having a passenger strand with the modification depicted DP1301P were used as a reference. Blue=2'-O-methyl ribonucleotide; Gray=deoxyribonucleotide; White=ribonucleotide; Dark Yellow=phosophorothioate deoxyribonucleotide; Green=phosphorothioate 2'-O-methyl ribonucleotide; Pink=phosphorothioate ribonucleotide; Light Yellow=methylphosphonate deoxyribonucleotide. Arrows indicate predicted Dicer cleavage sites.

FIG. 6B shows single stranded guide extended DsiRNA agents having a passenger strand depicted by DP1301P and a guide strand depicted by DP1337G; DP1338G; DP1340G; DP1341G; and DP1342G were generated and tested. DsiRNA agents having a passendger strand depicted by DP1301P and a guide strand depicted by DP1336G were used as a reference FIG. 6A). Descriptions of the modification patterns of the discontinuous complements are labeled to the right. RNA=ribonucleotide; PS=phosphorothioate; DNA=deoxyribonucleotide; 2'OMe=2'-O-methyl; Underline=2'-O-methyl ribonucleotide; Bold=guide strand 5' overhang; lower=deoxyribonucleotide; UPPER=ribonucleotide. Arrows indicate predicted Dicer cleavage sites.

FIG. 7 is a histogram showing the normalized fold expression of KRAS-249M using DsiRNA agents having the passenger strands and guide strands depicted in FIG. 5. Hela cells were treated with 0.1 nM of the DsiRNA agents in RNAiMAX, 24 hrs.

FIG. 8B presents Ssingle stranded guide extended DsiRNA agents having a passenger strand depicted by DP1001P and a guide strand depicted by DP1350G; DP1351G; DP1352G; DP1353G; DP1354G; and DP1355G were generated and tested. DsiRNA agents having a passendger strand depicted by DP1001P and a guide strand depicted by DP1002G were used as a reference (FIG. 8A). Descriptions of the modification patterns of the discontinuous complements are labeled to the right. RNA=ribonucleotide; PS=phosphorothioate; DNA=deoxyribonucleotide; 2'OMe=2'-O-methyl; Underline=2'-O-methyl ribonucleotide; Bold=guide strand 5' overhang; lower=deoxyribonucleotide; UPPER=ribonucleotide. Arrows indicate predicted Dicer cleavage sites.

FIG. 9 is a histogram showing the normalized fold expression of HPRT1 using DsiRNA agents having the passenger strands and guide strands depicted in FIG. 7. Hela cells were treated with 0.1 nM of the DsiRNA agents in RNAiMAX, 24 hrs.

FIG. 10 is an image of a gel showing a Dicer activity on single stranded guide extended DsiRNA agents (passenger+ guide strands) targeting KRAS-249M or HPRT1. Treatment: 2 h@37C Turbo Dicer (1 U/reaction). Gel: 18% Tris 90'@10 W. Loading: (1 μl 50 μM+50 μl Buffer and load 10 μl) or (5 μl reaction+20 μl Buffer and load 10 μl).

FIG. 11 shows the sequence and structure of exemplary short oligos that complement guide strand extensions ("discontinuous complements"), which are 1-16 nucleotides in length, base paired to 5' guide strand extensions. Single stranded guide extended DsiRNA agents having a discontinuous complement depicted by DP1365P; DP1366P; DP1367P; DP1368P; and DP1369P were generated and tested. Descriptions of the modification patterns of the discontinuous complements are labeled to the right. RNA=ribonucleotide; PS=phosphorothioate; DNA=deoxyribonucleotide; 2'OMe=2'-O-methyl; Underline=2'-O-methyl ribonucleotide; Bold=guide strand 5' overhang; lower=deoxyribonucleotide; UPPER=ribonucleotide. Arrows indicate predicted Dicer cleavage sites.

FIG. 12 is a histogram showing the normalized fold expression of KRAS-249M using DsiRNA agents having the passenger strands and guide strands depicted in FIG. 7 and the discontinuous complements depicted in FIG. 10. The discontinuous complements used is labeled above each set of the three bars corresponding to DsiRNA agents having a 5' guide single stranded extension (l.-r. DNA, RNA, 2'OMe RNA). Hela cells were treated with 0.1 nM of the DsiRNA agents in RNAiMAX, 24 hrs.

FIG. 13 is a histogram showing the normalized fold expression of HPRT1 using DsiRNA agents having the passenger strands and guide strands depicted in FIG. 7 and the discontinuous complements depicted in FIG. 10. The discontinuous complement used is labeled above each set of the three bars corresponding to DsiRNA agents having a 5' guide single stranded extension (l.-r. DNA, RNA, 2'OMe RNA). Hela cells were treated with 0.1 nM of the DsiRNA agents in RNAiMAX, 24 hrs.

FIG. 14 show the structure and predicted Dicer-mediated processing of exemplary single strand extended Dicer substrates in an in vivo experiment (Experimental conditions: Treatment: 10 mg/kg one injection; Target: KRAS; Transfection: invivoFectamine; Tissue: Liver). Panel A depicts a modification pattern used in a negative control DsiRNA without a single stranded extension. Panel B depicts a modification pattern used in a positive control DsiRNA without a single stranded extension. Panel C depicts a modification pattern used in a test DsiRNA without a single stranded extension. Panel D depicts a modification pattern used in a test "guide strand extended" DsiRNA agent, which has a guide strand 5' overhang 1-30 nucleotides in length (10 nucleotides as shown). Panel E depicts a modification pattern used in a test "guide strand extended" DsiRNA agent, which has a guide strand 5' overhang 1-30 nucleotides in length (10 nucleotides as shown). In each pair of oligonucleotide strands forming a DsiRNA, the upper strand is the passenger strand and the lower strand is the guide strand. Blue=ribonucleotide or modified ribonucleotide (e.g., 2'-O-methyl ribonucleotide); Gray=deoxyribonucleotide or ribonucleotide; White=ribonucleotide; Dark Yellow=deoxyribonucleotide, ribonucleotide, or modified nucleotide (e.g., 2'-O-methyl ribonucleotide, phosophorothioate deoxyribonucleotide; methylphosphonate deoxyribonucleotide). Small arrow=Dicer cleavage site; large arrow=discontinuity. $^A$=position starting from the nucleotide residue of said second strand that is complementary to the 5' terminal nucleotide residue of passenger strand (position $1^A$); $^B$=position starting from the 5' terminal nucleotide residue of guide strand. Small arrows indicate predicted Dicer cleavage sites; a large arrow indicates a discontinuity.

FIG. 16 is a histogram showing the normalized fold expression of mKRAS in liver of individual animals treated with DsiRNA agents having the passenger strands and guide strands depicted in FIGS. 14 and/or 15. Animals were treated with a 10 mg/kg injection of the DsiRNA agents in invivoFectamine and liver samples were analyzed.

FIG. 17 is a histogram showing the normalized fold expression of mKRAS in liver of animals treated with DsiRNA agents having the passenger strands and guide strands depicted in FIGS. 14 and/or 15. Animals were treated with a 10 mg/kg injection of the DsiRNA agents in in vivoFectamine and liver samples were analyzed.

FIG. 18 are graphs showing the normalized fold expression of mKRAS in liver of animals treated with DsiRNA agents having the passenger strands and guide strands depicted in FIGS. 14 and/or 15. Animals were treated with a 10 mg/kg injection of the DsiRNA agents in in vivoFectamine and liver samples were analyzed.

FIG. 19 is a histogram showing the normalized fold expression of mKRAS in spleen of individual animals treated with DsiRNA agents having the passenger strands and guide strands depicted in FIGS. 14 and/or 15. Animals were treated with a 10 mg/kg injection of the DsiRNA agents in in vivoFectamine and spleen samples were analyzed.

FIG. 20 is a histogram showing the normalized fold expression of mKRAS in spleen of animals treated with DsiRNA agents having the passenger strands and guide strands depicted in FIGS. 14 and/or 15. Animals were treated with a 10 mg/kg injection of the DsiRNA agents in invivoFectamine and spleen samples were analyzed.

FIG. 21 are graphs showing the normalized fold expression of mKRAS in spleen of animals treated with DsiRNA agents having the passenger strands and guide strands depicted in FIGS. 14 and/or 15. Animals were treated with a 10 mg/kg injection of the DsiRNA agents in in vivoFectamine and spleen samples were analyzed.

FIG. 22 is a histogram showing the normalized fold expression of mKRAS in kidney of individual animals treated with DsiRNA agents having the passenger strands and guide strands depicted in FIGS. 14 and/or 15. Animals were treated with a 10 mg/kg injection of the DsiRNA agents in in vivoFectamine and kidney samples were analyzed.

FIG. 23 is a histogram showing the normalized fold expression of mKRAS in kidney of animals treated with DsiRNA agents having the passenger strands and guide strands depicted in FIGS. 14 and/or 15. Animals were treated with a 10 mg/kg injection of the DsiRNA agents in invivoFectamine and kidney samples were analyzed.

FIG. 24 are graphs showing the normalized fold expression of mKRAS in kidney of animals treated with DsiRNA agents having the passenger strands and guide strands depicted in FIGS. 14 and/or 15. Animals were treated with a 10 mg/kg injection of the DsiRNA agents in invivoFectamine and kidney samples were analyzed.

DETAILED DESCRIPTION

Figure 6A:
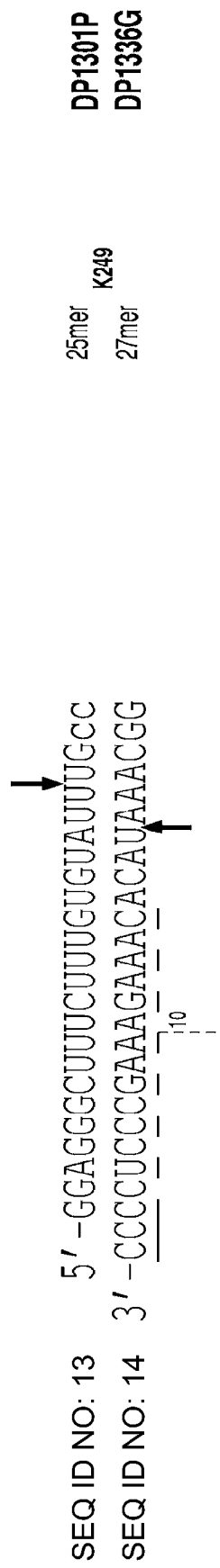
FIGS. 6A and B shows the sequence, structure, and predicted Dicer-mediated processing of exemplary "guide strand extended" DsiRNA agents targeting KRAS-249M, which have a guide strand 5' overhang 1-15 nucleotides in length.
Figure 8A:
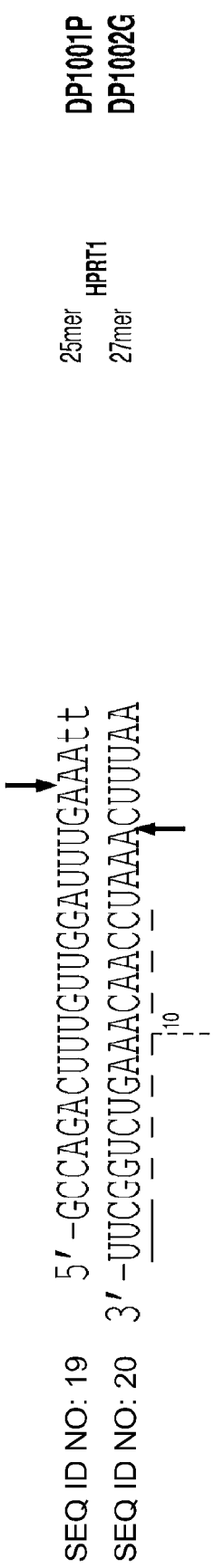
FIGS. 8A and B shows the sequence, structure, and predicted Dicer-mediated processing of exemplary "guide strand extended" DsiRNA agents targeting HPRT1, which have a guide strand 5' overhang 1-15 nucleotides in length.

The invention provides compositions and methods for reducing expression of a target gene in a cell, involving contacting a cell with an isolated double stranded nucleic acid in an amount effective to reduce expression of a target gene in a cell. The dsNAs of the invention possess a single stranded nucleotide region either at the 5' terminus of the antisense strand or at the 3' terminus of the sense strand are effective RNA interference agents (in most embodiments, the single stranded extension comprises at least one modified nucleotide and/or phosphate back bone modification). Surprisingly, as demonstrated herein, single-stranded extended Dicer-substrate siRNAs (DsiRNAs) were effective RNA inhibitory agents when compared to corresponding DsiRNAs.

The surprising discovery that single stranded extended DsiRNA agents do not exhibit decreases in efficacy allows for the generation of DsiRNAs that remain effective while providing greater spacing for, e.g., attachment of DsiRNAs to additional and/or distinct functional groups, inclusion/patterning of stabilizing modifications (e.g., PS-NA moieties) or other forms of modifications capable of adding further functionality and/or enhancing, e.g., pharmacokinetics, pharmacodynamics or biodistribution of such agents, as compared to dsRNA agents of corresponding length that do not contain such single stranded DNA-extended domains.

The advantage provided by the newfound ability to lengthen either the 5' guide strand, the 3' passenger strand, or the 5' passenger strand of DsiRNA-containing dsNA duplexes while retaining activity of a post-Dicer-processed siRNA agent at levels greater than dsRNA duplexes of similar length is emphasized by the results presented herein. The ability to extend either the 5' guide strand, the 3' passenger strand, or 5' passenger strand of DsiRNA agents without observing a corresponding reduction in RNA silencing activity can also allow for certain functional groups to be attached to such agents that would otherwise not be possible, because of the ability of such functional groups to interfere with RNA silencing activity when present in tighter configurations.

Additionally, single stranded extended DsiRNA agents may include a third short (1-16 nucleotides in length) oligonucleotide which base-pairs with the single stranded region of a single extended DsiRNAs, e.g., which base-pairs to a guide 5' single stranded extended region. The third oligo provides advantages to the use of single stranded extended DsiRNA agents: (a) to stabilize the single stranded extension (without being bound to a particular theory, the single strand extended DsiRNA might be rapidly degraded) and (b) to provide an independent entity to which a targeting molecule (or other active agent) could be attached, which could then be joined to the single-stranded extended DsiRNA via annealing (versus direct attachment of the targeting molecule to the single stranded extended DsiRNA).

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which, in certain cases, are metabolized in a manner similar to the reference nucleotides. Examples of such analogs include, without limitation, phosphorothioates, phosphoramidates, methylphosphonates, chiral-methyl phosphonates, 2-O-methyl ribonucleotides, peptide-nucleic acids (PNAs).

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, a "double-stranded nucleic acid" or "dsNA" is a molecule comprising two oligonucleotide strands which form a duplex. A dsNA may contain ribonucleotides, deoxyribonucleotides, modified nucleotides, and combinations thereof. The double-stranded NAs of the instant invention are substrates for proteins and protein complexes in the RNA interference pathway, e.g., Dicer and RISC. An exemplary structure of one form of dsNA of the invention is shown in FIG. 1A, Panel B, and such structures characteristically comprise an RNA duplex in a region that is capable of functioning as a Dicer substrate siRNA (DsiRNA) and a single stranded region, which is located at a position 5' of the projected Dicer cleavage site of the second strand of the DsiRNA/DNA agent. An exemplary structure of another form of dsNA of the invention is shown in FIG. 1A, Panel C, and such structures characteristically comprise an RNA duplex in a region that is capable of functioning as a Dicer substrate siRNA (DsiRNA) and a single stranded region, which is located at a position 3' of the projected Dicer cleavage site of the first strand of the DsiRNA/DNA agent. In further embodiments, the instant invention provides a structure that characteristically comprises an RNA duplex that is capable of functioning as a Dicer substrate siRNA (DsiRNA) and a single stranded region comprising at least one modified nucleotide and/or phosphate backbone modification, which is located at a position 3' of the projected Dicer cleavage site of the second strand of the DsiRNA/DNA agent. In alternative embodiments, the instant invention provides a structure that characteristically comprises an RNA duplex that is capable of functioning as a Dicer substrate siRNA (DsiRNA) and a single stranded region comprising at least one modified nucleotide and/or phosphate backbone modification, which is located at a position 5' of the projected Dicer cleavage site of the first strand of the DsiRNA/DNA agent In certain embodiments, the DsiRNAs of the invention can possess deoxyribonucleotide residues at sites immediately adjacent to the projected Dicer enzyme cleavage site(s). For example, in the all the DsiRNAs shown in FIG. 2 and in the sixth, seventh, eighth, ninth, tenth, eleventh, and twelfth DsiRNAs shown in FIG. 3, deoxyribonucleotides can be found (starting at the 5' terminal residue of the first strand as position 1) at position 24 and sites 3' of position 24 (e.g., 24, 25, 26, 27, 28, 29, 30, etc.). Deoxyribonucleotides may also be placed on the second strand commencing at the nucleotide that is complementary to position 20 of the first strand, and also at positions on the second strand that are located in the 5' direction of this nucleotide. Thus, certain effective DsiRNAs of the invention possess only 19 duplexed ribonucleotides prior to commencement of introduction of deoxyribonucleotides within the first strand, second strand, and/or both strands of such DsiRNAs.

As used herein, "duplex" refers to a double helical structure formed by the interaction of two single stranded nucleic acids. According to the present invention, a duplex may contain first and second strands which are sense and antisense, or which are target and antisense. A duplex is typically formed by the pairwise hydrogen bonding of bases, i.e., "base pairing", between two single stranded nucleic acids which are oriented antiparallel with respect to each other. As used herein, the term "duplex" refers to the regions of the first and second strands which align such that if the aligned bases of the strands are complementary, they may Watson-Crick base pair. The term "duplex" does not include one or more single stranded nucleotides which includes a 5' or 3' terminal single stranded nucleotide. The term "duplex" includes a region of aligned first and second strands which may be fully (100%) base paired and a region of aligned first and second strands which contains 1, 2, 3, 4, or 5 unpaired bases, as long as the first strand 5' terminal nucleotide and the first strand 3' terminal nucleotide are Watson-Crick base paired with a corresponding nucleotide of the second strand. As used herein, "fully duplexed" refers to all nucleotides in between the paired 5' and 3' terminal nucletides are base-paird. As used herein, "substantially duplexed" refers to a duplex between the strands such that there is 1, 2, 3, 4, 5 unpaired base pair(s) (consecutive or non-consecutive) between the between the 5' terminal and 3' terminal nucleotides of the first strand.

Pairing in duplexes generally occurs by Watson-Crick base pairing, e.g., guanine (G) forms a base pair with cytosine (C) in DNA and RNA (thus, the cognate nucleotide of a guanine deoxyribonucleotide is a cytosine deoxyribonucleotide, and vice versa), adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by stacking interactions between adjacent nucleotides. As used herein, a duplex may be established or maintained by base pairing or by stacking interactions. A duplex is formed by two complementary nucleic acid strands, which may be substantially complementary or fully complementary (see below).

As used herein, "corresponds to" or "corresponding to" refers to first and second strand bases that are aligned in a duplex such that the nucleotide residue of the second strand aligns with the residue of the first strand, when first strand position 1 is base paired with a nucleotide of said second strand such that said second strand comprises a 3' single stranded overhang of 1-6 nucleotides in length. "Corresponds to" does not require pairing via formation of a Watson-Crick base pair, but rather includes both aligned and unpaired first strand/second strand nucleotides as well as aligned and base paired first strand/second strand nucleotides.

By "complementary" or "complementarity" is meant that a nucleic acid can form hydrogen bond(s) with another nucleic acid sequence by either traditional Watson-Crick or Hoogsteen base pairing. In reference to the nucleic acid molecules of the present disclosure, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner, et al., CSH Symp. Quant. Biol. LII, pp. 123-133, 1987; Frier, et al., Proc. Nat. Acad. Sci. USA 83:9373-9377, 1986; Turner, et al., J. Am. Chem. Soc. 109:3783-3785, 1987). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary, respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

As used herein, the "3' region" with respect to the antisense strand refers to the consecutive nucleotides of the antisense strand that are 3' distal (on the antisense strand) to the nucleotide of the antisense strand that aligns with corresponding positions 1-19, 1-20 or 1-21 of the sense strand. To avoid doubt, the "3' region", when referring to the antisense strand, is meant to encompass antisense nucleotides in a duplex formed between the antisense strand and its cognate target RNA 3' distal to (on the antisense strand which correspond to nucleotides on the target RNA that are 5' distal to) the projected Argonaute 2 (Ago2) cut site.

The first and second strands of the agents of the invention (sense and antisense oligonucleotides) are not required to be completely complementary in the duplexed region. In one embodiment, the RNA sequence of the antisense strand contains one or more mismatches (1, 2, 3, 4 or 5, consecutive or nonconsecutive), i.e., mismatched with respect to the duplexed sense strand of the isolated double stranded nucleic acid according to the invention, contains one or more (1, 2, 3, 4 or 5, consecutive or nonconsecutive), modified nucleotides (base analog)s. In an exemplary embodiment, such mismatches occur within the 3' region, as defined hereinabove, of RNA sequence of the antisense strand. In one aspect, two, three, four or five mismatches or modified nucleotides with base analogs are incorporated within the RNA sequence of the antisense strand that is 3' in the antisense strand of the projected Ago2 cleavage site of the target RNA sequence when the target RNA sequence is hybridized.

The use of mismatches or decreased thermodynamic stability (specifically at or near the 3'-terminal residues of sense/5'-terminal residues of the antisense region of siRNAs) has been proposed to facilitate or favor entry of the antisense strand into RISC (Schwarz et al., 2003; Khvorova et al., 2003), presumably by affecting some rate-limiting unwinding steps that occur with entry of the siRNA into RISC. Thus, terminal base composition has been included in design algorithms for selecting active 21mer siRNA duplexes (Ui-Tei et al., 2004; Reynolds et al., 2004).

Inclusion of such mismatches within the DsiRNA agents of the instant invention can allow such agents to exert inhibitory effects that resemble those of naturally-occurring miRNAs, and optionally can be directed against not only naturally-occurring miRNA target RNAs (e.g., 3' UTR regions of target transcripts) but also against RNA sequences for which no naturally-occurring antagonistic miRNA is known to exist. For example, DsiRNAs of the invention possessing mismatched base pairs which are designed to resemble and/or function as miRNAs can be synthesized to target repetitive sequences within genes/transcripts that might not be targeted by naturally-occurring miRNAs (e.g., repeat sequences within the Notch protein can be targeted, where individual repeats within Notch can differ from one another (e.g., be degenerate) at the nucleic acid level, but which can be effectively targeted via a miRNA mechanism that allows for mismatch(es) yet also allows for a more promiscuous inhibitory effect than a corresponding, perfect match siRNA agent). In such embodiments, target RNA cleavage may or may not be necessary for the mismatch-containing DsiRNA agent to exert an inhibitory effect.

In one embodiment, a double stranded nucleic acid molecule of the invention comprises or functions as a microRNA (miRNA). By "microRNA" or "miRNA" is meant a small double stranded RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). In one embodiment, the microRNA of the invention, has partial complementarity (i.e., less than 100% complementarity) between the sense strand (e.g., first strand) or sense region and the antisense strand (e.g., second strand) or antisense region of the miRNA molecule or between the antisense strand or antisense region of the miRNA and a corresponding target nucleic acid molecule (e.g., target mRNA). For example, partial complementarity can include various mismatches or non-base paired nucleotides (e.g., 1, 2, 3, 4, 5 or more mismatches or non-based paired nucleotides, such as nucleotide bulges) within the double stranded nucleic acid molecule structure, which can result in bulges, loops, or overhangs that result between the sense strand or sense region and the antisense strand or antisense region of the miRNA or between the antisense strand or antisense region of the miRNA and a corresponding target nucleic acid molecule.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | Vender | Cat# | Lot# | m.w./Stock | To make 50 mL solution |
|---|---|---|---|---|---|---|
| NaCl | 100 mM | Sigma | S-5150 | 41K8934 | 5M | 1 mL |
| KCl | 80 mM | Sigma | P-9541 | 70K0002 | 74.55 | 0.298 g |
| MgCl$_2$ | 8 mM | Sigma | M-1028 | 120K8933 | 1M | 0.4 mL |
| sucrose | 2% w/v | Fisher | BP220-212 | 907105 | 342.3 | 1 g |
| Tris-HCl | 16 mM | Fisher | BP1757-500 | 12419 | 1M | 0.8 mL |
| NaH$_2$PO$_4$ | 1 mM | Sigma | S-3193 | 52H-029515 | 120.0 | 0.006 g |
| EDTA | 0.02 mM | Sigma | E-7889 | 110K89271 | 0.5M | 2 µL |
| H$_2$O | | Sigma | W-4502 | 51K2359 | | to 50 mL |
| pH = 7.0 at 20° C. | | | | adjust with HCl | | |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001);

Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

Certain dsNAs of this invention are chimeric dsNAs. "Chimeric dsNAs" or "chimeras", in the context of this invention, are dsNAs which contain two or more chemically distinct regions, each made up of at least one nucleotide. These dsNAs typically contain at least one region primarily comprising ribonucleotides (optionally including modified ribonucleotides) that form a Dicer substrate siRNA ("DsiRNA") molecule. This DsiRNA region is covalently attached, e.g., via conventional phosphate bonds or via modified phosphate linkages (e.g., phosphorothioate) to a second region comprising a single stranded nucleotide region ("a single stranded extended region") which confers one or more beneficial properties (such as, for example, increased efficacy, e.g., increased potency and/or duration of DsiRNA activity, function as a recognition domain or means of targeting a chimeric dsNA to a specific location, for example, when administered to cells in culture or to a subject, functioning as an extended region for improved attachment of functional groups, payloads, detection/detectable moieties, functioning as an extended region that allows for more desirable modifications and/or improved spacing of such modifications, etc.). This second region may also include modified or synthetic nucleotides and/or modified or synthetic deoxyribonucleotides.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide. As used herein, the term "deoxyribonucleotide" also includes a modified ribonucleotide that does not permit Dicer cleavage of a dsNA agent, e.g., a 2'-O-methyl ribonucleotide, a phosphorothioate-modified ribonucleotide residue, etc., that does not permit Dicer cleavage to occur at a bond of such a residue.

As used herein, the term "PS-NA" refers to a phosphorothioate-modified nucleotide residue. The term "PS-NA" therefore encompasses both phosphorothioate-modified ribonucleotides ("PS-RNAs") and phosphorothioate-modified deoxyribonucleotides ("PS-DNAs").

In certain embodiments, a chimeric DsiRNA/DNA agent of the invention comprises at least one duplex region of at least 23 nucleotides in length, within which at least 50% of all nucleotides are unmodified ribonucleotides. As used herein, the term "unmodified ribonucleotide" refers to a ribonucleotide possessing a hydroxyl (—OH) group at the 2' position of the ribose sugar.

In certain embodiments, a chimeric DsiRNA/DNA agent of the invention comprises at least one region, located 3' of the projected Dicer cleavage site on the first strand and 5' of the projected Dicer cleavage site on the second strand, having a length of at least 2 base paired nucleotides in length, wherein at least 50% of all nucleotides within this region of at least 2 base paired nucleotides in length are unmodified deoxyribonucleotides. As used herein, the term "unmodified deoxyribonucleotide" refers to a ribonucleotide possessing a single proton at the 2' position of the ribose sugar.

As used herein, antisense strand, guide strand and second oligonucleotide refer to the same strand of a given dicer substrate molecule according to the invention; while sense strand, passenger strand, and first oligonucleotide refer to the same strand of a given dicer substrate.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least be capable of forming a hybrid with, and thus be able to duplex with the antisense strand As used herein, "guide strand" refers to a single stranded nucleic acid molecule of a dsNA or dsNA-containing molecule, which has a sequence sufficiently complementary to that of a target RNA to result in RNA interference. After cleavage of the dsNA or dsNA-containing molecule by Dicer, a fragment of the guide strand remains associated with RISC, binds a target RNA as a component of the RISC complex, and promotes cleavage of a target RNA by RISC. A guide strand is an antisense strand.

As used herein, "target RNA" refers to an RNA that would be subject to modulation guided by the antisense strand, such as targeted cleavage or steric blockage. The target RNA could be, for example genomic viral RNA, mRNA, a pre-mRNA, or a non-coding RNA. The preferred target is mRNA, such as the mRNA encoding a disease associated protein, such as ApoB, Bcl2, Hif-lalpha, Survivin or a p21 ras, such as Ha. ras, K-ras or N-ras.

As used herein, "passenger strand" refers to an oligonucleotide strand of a dsNA or dsNA-containing molecule, which has a sequence that is complementary to that of the guide strand A passenger strand is a sense strand.

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments about 19-25 nucleotides long, usually with a two-base overhang on the 3' end. With respect to the dsNAs of the invention, the duplex formed by a dsRNA region of a dsNA of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP_085124, hereby incorporated by reference.

Dicer "cleavage" is determined as follows (e.g., see Collingwood et al., Oligonucleotides 18:187-200 (2008)). In a Dicer cleavage assay, RNA duplexes (100 µmol) are incubated in 20 µL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-35 by dsRNA, preferably 26-30 by dsRNA, optionally extended as described herein) is cleaved to a shorter dsRNA (e.g., 19-23 by dsRNA, preferably, 21-23 by dsRNA).

As used herein, "Dicer cleavage site" refers to the sites at which Dicer cleaves a dsRNA (e.g., the dsRNA region of a dsNA of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae I, et al. (2006). "Structural basis for double-stranded RNA processing by Dicer". *Science* 311 (5758): 195-8.). As shown, e.g., in FIG. 2, Dicer is projected to cleave certain double-stranded nucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsNA molecules distinct from those depicted in FIG. 2 may be similarly identified via art-recognized methods, including those described in Macrae et al. While the Dicer cleavage event depicted in FIG. 2 generates a 21 nucleotide siRNA, it is noted that Dicer cleavage of a dsNA (e.g., DsiRNA) can result in generation of Dicer-processed siRNA lengths of 19 to 23 nucleotides in length. Indeed, in one aspect of the invention that is described in greater detail below, a double stranded DNA region is included within a dsNA for purpose of directing prevalent Dicer excision of a typically non-preferred 19mer siRNA.

As used herein, "overhang" refers to unpaired nucleotides, in the context of a duplex having two or four free ends at either the 5' terminus or 3' terminus of a dsNA. In certain embodiments, the overhang is a 3' or 5' overhang on the antisense strand or sense strand.

As used herein, "target" refers to any nucleic acid sequence whose expression or activity is to be modulated. In particular embodiments, the target refers to an RNA which duplexes to a single stranded nucleic acid that is an antisense strand in a RISC complex. Hybridization of the target RNA to the antisense strand results in processing by the RISC complex. Consequently, expression of the RNA or proteins encoded by the RNA, e.g., mRNA, is reduced.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by any of several endo- or exo-nucleases (e.g., RNase III, RNase P, RNase T1, RNase A (1, 2, 3, 4/5), oligonucleotidase, etc.).

As used herein, "reference" is meant a standard or control. As is apparent to one skilled in the art, an appropriate reference is where only one element is changed in order to determine the effect of the one element.

As used herein, "modified nucleotide" refers to a nucleotide that has one or more modifications to the nucleoside, the nucleobase, furanose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 21-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in Eckstein et al., U.S. Pat. No. 5,672,695 and Matulic-Adamic et al., U.S. Pat. No. 6,248,878.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

In reference to the nucleic acid molecules of the present disclosure, nucleotides in certain positions on either strand of the dsNA may be specified. With reference to FIGS. 1-3, the conventions for denoting positions of the DsiRNAs of the invention are shown in Table 2.

TABLE 2

Description of Numbering Convention as to Strand Positions

| | |
|---|---|
| position | A position located on the passenger strand is denoted by a number without a superscript label.(e.g., position 1). Position 1 of the passenger strand is the 5'-terminal nucleotide, except for the 5' extended passenger strands, where the 5' terminal nucleotide occurs in the extended region and is accorded the highest number with a superscript E (see below and FIG. 1A). |
| position$^A$ | A position located on the guide strand is designated with a superscript A (e.g., position 1$^A$. The guide strand is numbered such that the first base paired nucleotide at its 3' terminus is referred to as (e.g., position 1$^A$). Where the guide strand contains a 3' terminal single stranded overhang of 1-6 nucleotides, those nucleotides are simply referred to as 3' terminal guide strand unpaired or single stranded residues. |

TABLE 2-continued

Description of Numbering Convention as to Strand Positions

| | |
|---|---|
| position$^B$ | A position located on the guide strand in the extended 5' region is labeled with a superscript B (e.g., position $1^B$ represents the 5' terminal nucleotide of an extended guide strand (see FIG. 1A)). |
| position$^C$ | A position located on the third oligonucleotide. The third oligonucleotide is complementary to the extended region of the guide strand and is discontinuous with the passenger strand. Position $1^C$ (see FIG. 1A) represents the 5' terminal nucleotide of the third oligoncleotide. |
| position$^D$ | A position located on a 3' extended passenger strand, such that position $1^D$ references the 3' terminal nucleotide residue of the extended passenger strand |
| position$^E$ | A position located on the extended region of a 5' extended passenger strand. Position $1^E$ is the unpaired nucleotide consecutive (i.e., adjacent) to the first paired nucleotide of the passenger strand (see FIG. 1A). |
| position$^F$ | A position located in the duplex region of a 5' extended passenger strand, such that position $1^F$ references the first paired nucleotide on the 5' passenger strand (starting from the 5' end) and is the nucleotide consecutive to the position $1^E$ of the passenger strand, which is an unpaired nucleotide of the strand 5' single stranded extension.(see FIG. 1A). |

In reference to the nucleic acid molecules of the present disclosure, the modifications may exist in patterns on a strand of the dsNA. As used herein, "alternating positions" refers to a pattern where every other nucleotide is a modified nucleotide or there is an unmodified nucleotide (e.g., an unmodified ribonucleotide) between every modified nucleotide over a defined length of a strand of the dsNA (e.g., 5'-MNMNMN-3'; 3'-MNMNMN-5'; where M is a modified nucleotide and N is an unmodified nucleotide). The modification pattern starts from the first nucleotide position at either the 5' or 3' terminus according to any of the position numbering conventions described herein (in certain embodiments, position 1 is designated in reference to the terminal residue of a strand following a projected Dicer cleavage event of a DsiRNA agent of the invention; thus, position 1 does not always constitute a 3' terminal or 5' terminal residue of a pre-processed agent of the invention). The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand of the dsNA (e.g., 5'-MMNNMMNNMMNN-3'; 3'-MMNNMMNNMMNN-5'; where M is a modified nucleotide and N is an unmodified nucleotide). The modification pattern starts from the first nucleotide position at either the 5' or 3' terminus according to any of the position numbering conventions described herein. The pattern of modified nucleotides at alternating positions may run the full length of the strand, but preferably includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In the dsNAs of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the compounds and methods of the invention., e.g., those disclosed in U.S. Pat. Nos. 5,432,272 and 6,001,983 to Benner and US Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3-β-D-ribofuranosyl-(1-methyl-pyrazolo[4,3-d]pyrimidine-5,7(4H,6H)-dione) (P), iso-cytosine (iso-C), iso-guanine (iso-G), 1-β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S),2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc.,122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Preferably, the universal bases does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43).

As used herein, "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins, stem loops, or extended loops.

As used herein, "extended loop" in the context of a dsRNA refers to a single stranded loop and in addition 1, 2, 3, 4, 5, 6 or up to 20 base pairs or duplexes flanking the loop. In an extended loop, nucleotides that flank the loop on the 5' side form a duplex with nucleotides that flank the loop on the 3' side. An extended loop may form a hairpin or stem loop.

As used herein, "tetraloop" in the context of a dsRNA refers to a loop (a single stranded region) consisting of four nucleotides that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the four nucleotides in a tetraloop include but are not limited to non-Watson-Crick base pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM $NaHPO_4$ to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002.; SHINJI et al. Nippon Kagakkai Koen Yokoshu VOL. 78th; NO. 2; PAGE. 731 (2000).)

As used herein, "increase" or "enhance" is meant to alter positively by at least 5% compared to a reference in an assay. An alteration may be by 5%, 10%, 25%, 30%, 50%, 75%, or even by 100% compared to a reference in an assay. By "enhance Dicer cleavage," it is meant that the processing of a quantity of a dsRNA or dsRNA-containing molecule by Dicer results in more Dicer cleaved dsRNA products, that Dicer cleavage reaction occurs more quickly compared to the processing of the same quantity of a reference dsRNA or dsRNA-containing molecule in an in vivo or in vitro assay of this disclosure, or that Dicer cleavage is directed to cleave at a specific, preferred site within a dsNA and/or generate higher prevalence of a preferred population of cleavage products (e.g., by inclusion of DNA residues as described herein). In one embodiment, enhanced or increased Dicer cleavage of a dsNA molecule is above the level of that observed with an appropriate reference dsNA molecule. In another embodiment, enhanced or increased Dicer cleavage of a dsNA molecule is above the level of that observed with an inactive or attenuated molecule.

As used herein "reduce" is meant to alter negatively by at least 5% compared to a reference in an assay. An alteration may be by 5%, 10%, 25%, 30%, 50%, 75%, or even by 100% compared to a reference in an assay. By "reduce expression," it is meant that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., dsRNA molecule or dsRNA-containing molecule) in an in vivo or in vitro assay of this disclosure. In one embodiment, inhibition, down-regulation or reduction with a dsNA molecule is below that level observed in the presence of an inactive or attenuated molecule. In another embodiment, inhibition, down-regulation, or reduction with dsNA molecules is below that level observed in the presence of, e.g., a dsNA molecule with scrambled sequence or with mismatches. In another embodiment, inhibition, down-regulation, or reduction of gene expression with a nucleic acid molecule of the instant disclosure is greater in the presence of the nucleic acid molecule than in its absence.

As used herein, "cell" is meant to include both prokaryotic (e.g., bacterial) and eukaryotic (e.g., mammalian or plant) cells. Cells may be of somatic or germ line origin, may be totipotent or pluripotent, and may be dividing or non-dividing. Cells can also be derived from or can comprise a gamete or an embryo, a stem cell, or a fully differentiated cell. Thus, the term "cell" is meant to retain its usual biological meaning and can be present in any organism such as, for example, a bird, a plant, and a mammal, including, for example, a human, a cow, a sheep, an ape, a monkey, a pig, a dog, and a cat. Within certain aspects, the term "cell" refers specifically to mammalian cells, such as human cells, that contain one or more isolated dsNA molecules of the present disclosure. In particular aspects, a cell processes dsRNAs or dsRNA-containing molecules resulting in RNA intereference of target nucleic acids, and contains proteins and protein complexes required for RNAi, e.g., Dicer and RISC.

As used herein, "animal" is meant a multicellular, eukaryotic organism, including a mammal, particularly a human. The methods of the invention in general comprise administration of an effective amount of the agents herein, such as an agent of the structures of formulae herein, to a subject (e.g., animal, human) in need thereof, including a mammal, particularly a human. Such treatment will be suitably administered to subjects, particularly humans, suffering from, having, susceptible to, or at risk for a disease, or a symptom thereof.

By "pharmaceutically acceptable carrier" is meant, a composition or formulation that allows for the effective distribution of the nucleic acid molecules of the instant disclosure in the physical location most suitable for their desired activity.

The present invention is directed to compositions that comprise both a double stranded RNA ("dsRNA") duplex and DNA-containing extended region—in most embodiments, a dsDNA duplex—within the same agent, and methods for preparing them, that are capable of reducing the expression of target genes in eukaryotic cells. One of the strands of the dsRNA region contains a region of nucleotide sequence that has a length that ranges from about 15 to about 22 nucleotides that can direct the destruction of the RNA transcribed from the target gene. The dsDNA duplex region of such an agent is not necessarily complementary to the target RNA, and, therefore, in such instances does not enhance target RNA hybridization of the region of nucleotide sequence capable of directing destruction of a target RNA. Double stranded NAs of the invention can possess strands that are chemically linked, or can also possess an extended loop, optionally comprising a tetraloop, that links the first and second strands. In some embodiments, the extended loop containing the tetraloop is at the 3' terminus of the sense strand, at the 5' terminus of the antisense strand, or both.

In one embodiment, the dsNA of the invention comprises a double stranded RNA duplex region comprising 18-30 nts (for example, 18, 19, 20, 21, 22, 23, 24, 25, 26, 27, 28, 29 and 30 nts) in length.

"Extended" DsiRNA agents according to the invention can be categorized as either "guide extended" (the nucleotide region at the 5' terminus of the antisense strand that is present on the molecule in addition to the 26-30 base antisense sequence required for participation of the antisense strand in a dicer substrate) or "passenger extended" (the nucleotide region at the 3' terminus of the sense strand that is optionally present on the molecule in addition to the 25-30 base sense sequence required for sense strand participation in a dicer substrate; or the nucleotide region at the 5' terminus of the sense strand that is optionally present on the sense strand in addition to the 25-30 base sequence required for sense strand participation in a dicer substrate). Therefore, as used herein, the term "extended" is not meant to refer to the antisense (or second strand, or guide strand) 3' overhang of 1-6 single stranded nucleotides; rather "extended" as used herein refers to the opposite end of the dicer substrate molecule, that is, a 5' extended antisense strand, where the extended region is 10-30, preferably 10-15 nucleotides in length or a 3' extended sense strand, where the extended region is 10-30, preferably 10-15 nucleotides in length. The 5' extended antisense strand may be single stranded, and optionally may be duplexed with a third nucleic acid molecule which is complementary, preferably fully (100%) complementary, to the 5' extended single stranded region of the antisense strand. Therefore, in some embodiments, i.e., when the third nucleic acid molecule is present, the 5' extended region of the antisense strand is not single stranded, but rather is a duplex, or double stranded region. Preferably, according to the invention, the third nucleic acid molecule, i.e., the sense region that is complementary to the 5' extended antisense region, is not present unless a cognate 5' extended antisense region is present.

The DsiRNA/dsDNA agents of the instant invention can enhance the following attributes of such agents relative to DsiRNAs lacking extended second strand (e.g., antisense) 5' regions or extended first strand (e.g., sense) 3' regions: in vitro efficacy (e.g., potency and duration of effect), in vivo efficacy (e.g., potency, duration of effect, pharmacokinetics, pharmacodynamics, intracellular uptake, reduced toxicity). In certain embodiments, the 5' extended region of the second strand or 3' extended region of the first strand can optionally provide an additional agent (or fragment thereof), such as an aptamer or fragment thereof; a binding site (e.g., a "decoy" binding site) for a native or exogenously introduced moiety capable of binding to a 5' extended second strand nucleotide region or 3' extended first strand region, respectively in either a non-sequence-selective or sequence-specific manner (e.g., the 5' extended second strand nucleotide region of an agent of the instant invention can be designed to comprise one or more transcription factor recognition sequences and/or the 5' extended second strand nucleotide region can provide a sequence-specific recognition domain for a probe, marker, etc.).

As used herein, the term "pharmacokinetics" refers to the process by which a drug is absorbed, distributed, metabolized, and eliminated by the body. In certain embodiments of the instant invention, enhanced pharmacokinetics of a 5' extended second strand pr 3' extended first strand DsiRNA agent relative to an appropriate control DsiRNA refers to increased absorption and/or distribution of such an agent, and/or slowed metabolism and/or elimination of such a 5' second strand extended DsiRNA agent or 3' first strand extended DsiRNA agent from a subject administered such an agent.

As used herein, the term "pharmacodynamics" refers to the action or effect of a drug on a living organism. In certain embodiments of the instant invention, enhanced pharmacodynamics of a 5' second strand extended DsiRNA agent or 3' first strand extended DsiRNA agent relative to an appropriate control DsiRNA refers to an increased (e.g., more potent or more prolonged) action or effect of a 5' second strand extended DsiRNA agent or 3' first strand extended DsiRNA agent, respectively, upon a subject administered such agent, relative to an appropriate control DsiRNA.

As used herein, the term "stabilization" refers to a state of enhanced persistence of an agent in a selected environment (e.g., in a cell or organism). In certain embodiments, the 5' second strand extended DsiRNA or 3' first strand extended DsiRNA agents of the instant invention exhibit enhanced stability relative to appropriate control DsiRNAs. Such enhanced stability can be achieved via enhanced resistance of such agents to degrading enzymes (e.g., nucleases) or other agents.

In addition to the attributes described above for the 5' antisense extended dicer substrates according to the invention, where the optional third nucleic acid sense molecule of 10-30, preferably 10-15 nucleotides is present in a molecule, this third sense molecule may function to stabilize the entire molecule, and/or to confer another advantage, such as increase potency, prolong action or effect, enhance pharmacodynamic or pharmacological effects, and/or to provide an additional agent (or portion thereof), such as an aptamer or fragment thereof; a binding site (e.g., a "decoy" binding site) for a native or exogenously introduced moiety (e.g., a label) that is bound to and thus carried by the third molecule as it participates in the dicer substrate.

DsiRNA Design/Synthesis

It was previously shown that longer dsRNA species of from 25 to about 30 nucleotides (DsiRNAs) yield unexpectedly effective RNA inhibitory results in terms of potency and duration of action, as compared to 19-23mer siRNA agents. Without wishing to be bound by the underlying theory of the dsRNA processing mechanism, it is thought that the longer dsRNA species serve as a substrate for the Dicer enzyme in the cytoplasm of a cell. In addition to cleaving the dsNA of the invention into shorter segments, Dicer is thought to facilitate the incorporation of a single-stranded cleavage product derived from the cleaved dsNA into the RISC complex that is responsible for the destruction of the cytoplasmic RNA of or derived from the target gene. Prior studies (Rossi et al., U.S. Patent Application No. 2007/0265220) have shown that the cleavability of a dsRNA species (specifically, a DsiRNA agent) by Dicer corresponds with increased potency and duration of action of the dsRNA species. The instant invention, at least in part, provides for design of RNA inhibitory agents that direct the site of Dicer cleavage, such that preferred species of Dicer cleavage products are thereby generated.

In a model of DsiRNA processing, Dicer enzyme binds to a DsiRNA agent, resulting in cleavage of the DsiRNA at a position 19-23 nucleotides removed from a Dicer PAZ domain-associated 3' overhang sequence of the antisense strand of the DsiRNA agent. This Dicer cleavage event results in excision of those duplexed nucleic acids previously located at the 3' end of the passenger (sense) strand and 5' end of the guide (antisense) strand. Cleavage of a DsiRNA typically yields a 19mer duplex with 2-base overhangs at each end. As presently modeled in FIG. 2, this Dicer cleavage event generates a 21-23 nucleotide guide (antisense) strand (or, in certain instances where a longer guide strand 3' overhang is present, 24-27 nucleotide guide strands could result from Dicer cleavage) capable of directing sequence-specific inhibition of target mRNA as a RISC component.

The first and second oligonucleotides of the DsiRNA agents of the instant invention are not required to be completely complementary in the duplexed region. In one embodiment, the 3'-terminus of the sense strand contains one or more mismatches. In one aspect, about two mismatches are incorporated at the 3' terminus of the sense strand. In another embodiment, the DsiRNA of the invention is a double stranded RNA molecule containing two RNA oligonucleotides in the range of 25-66 nucleotides in length and, when annealed to each other, have a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003; Khvorova et al., 2003), presumably by affecting some rate-limiting unwinding steps that occur with entry of the siRNA into RISC. Thus, terminal base composition has been included in design algorithms for selecting active 21mer siRNA duplexes (Ui-Tei et al., 2004; Reynolds et al., 2004). With Dicer cleavage of the dsRNA region of this embodiment, the small end-terminal sequence which contains the mismatches will either be left unpaired with the antisense strand (become part of a 3'-overhang) or be cleaved entirely off the final 21-mer siRNA. These specific forms of "mismatches", therefore, do not persist as mismatches in the final RNA component of RISC. The finding that base mismatches or destabilization of segments at the 3'-end of the sense strand of Dicer substrate improved the potency of synthetic duplexes in RNAi, presumably by facilitating processing by Dicer, was a surprising finding of past works describing the design and use of 25-30mer dsRNAs (also termed "DsiRNAs" herein; Rossi et al., U.S. Patent Application Nos. 2005/0277610, 2005/0244858 and 2007/0265220). Exemplary mismatched or wobble base pairs of agents possessing mismatches are G:A, C:A, C:U, G:G, A:A, C:C, U:U, I:A, I:U and I:C. Base pair strength of such agents can also be lessened via modification of the nucleotides of such agents, including, e.g., 2-amino- or 2,6-diamino modifications of guanine and adenine nucleotides.

Exemplary Structures of DsiRNA Agent Compositions

The compositions of the invention comprise a dsNA which is a precursor molecule, i.e., the dsNA of the present invention is processed in vivo to produce an active small interfering nucleic acid (siRNA). The dsNA is processed by Dicer to an active siRNA which is incorporated into RISC.

In one aspect, the present invention provides compositions for RNA interference (RNAi) having a first or second strand that has at least 8 contiguous ribonucleotides. In certain embodiments, a DsiRNA of the invention has 9, 10, 11, 12, 13, 14, 15, 16, 17, 18, 19, 20, 21, 22, 23 or more (e.g., 24, 25, 26, 27, 28, 29, 30, 31, 32, 33, 34, 35, 26, or more, up to the full length of the strand) ribonucleotides, modified ribonucleotides (2'-O-methyl ribonucleotides, phosphorothioate linkages). In certain embodiments, the ribonucleotides or modified ribonucleotides are contiguous.

In one aspect, the present invention provides compositions for RNA interference (RNAi) that possess one or more deoxyribonucleotides within a region of a double stranded nucleic acid that is positioned 3' of a projected sense strand Dicer cleavage site and correspondingly 5' of a projected antisense strand Dicer cleavage site. In one embodiment, at least one nucleotide of the guide strand between and including the guide strand nucleotides corresponding to and thus base paired with passenger strand positions 24 to the 3' terminal nucleotide residue of the passenger strand is a deoxyribonucleotide. In some embodiments, the double stranded nucleic acid possesses one or more base paired deoxyribonucleotides within a region of the double stranded nucleic acid that is positioned 3' of a projected sense strand Dicer cleavage site and correspondingly 5' of a projected antisense strand Dicer cleavage site In certain embodiments, the DsiRNA agents of the invention can have any of the following exemplary structures:

In one such embodiment, the DsiRNA comprises:

5'-XXXXXXXXXXXXXXXXXXXXXXXXX$_{N*}$-3'

3'-YXXXXXXXXXXXXXXXXXXXXXXXXX$_{N*}$Z$_{N}$-5' wherein "X"=RNA, "Y" is an optional overhang domain comprised of 0-10 RNA monomers that are optionally 2'-O-methyl RNA monomers—in certain embodiments, "Y" is an overhang domain comprised of 0-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In a related embodiment, the DsiRNA comprises:

$$5'-XXXXXXXXXXXXXXXXXXXXXXX_{N*}DD-3'$$
$$3'-YXXXXXXXXXXXXXXXXXXXXXXX_{N*}XXZ_{N}-5'$$

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In another such embodiment, the DsiRNA comprises:

$$5'-XXXXXXXXXXXXXXXXXXXXXXX_{N*}|E_{N}-3'$$
$$3'-YXXXXXXXXXXXXXXXXXXXXXXX_{N*}Z_{N}-5'$$

wherein "X"=RNA, "Y" is an optional overhang domain comprised of 0-10 RNA monomers that are optionally 2'-O-methyl RNA monomers—in certain embodiments, "Y" is an overhang domain comprised of 0-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "E"=DNA, RNA, or modified nucleotide, "|"=a discontinuity, and "N"=1 to 50 or more, but is optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In a related embodiment, the DsiRNA comprises:

$$5'-XXXXXXXXXXXXXXXXXXXXXXX_{N*}DD|E_{N}-3'$$
$$3'-YXXXXXXXXXXXXXXXXXXXXXXX_{N*}XXZ_{N}-5'$$

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In another such embodiment, the DsiRNA comprises:

$$5'-XXXXXXXXXXXXXXXXXXXXXXX_{N*}Z_{N}-3'$$
$$3'-YXXXXXXXXXXXXXXXXXXXXXXX_{N*}-5'$$

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In a related embodiment, the DsiRNA comprises:

$$5'-XXXXXXXXXXXXXXXXXXXXXXX_{N}*DDZ_{N}-3'$$
$$3'-YXXXXXXXXXXXXXXXXXXXXXXX_{N}*XX-5'$$

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In an additional embodiment, the DsiRNA comprises:

$$5'-XXXXXXXXXXXXXXXXXXXXXXX_{N}*DDZ_{N}-3'$$
$$3'-Y\underline{X}XXXXXXXXXXXXXXXXXXXXXXX_{N}*XX-5'$$

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In another such embodiment, the DsiRNA comprises:

$$5'-XXXXXXXXXXXXXXXXXXXXXXX_{N}*-3'$$
$$3'-Y\underline{XXXXXXXXXXXXX}XXXXXXXXXX_{N}*Z_{N}-5'$$

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

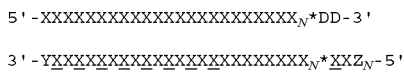

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In any of the above-depicted structures, the 5' end of either the sense strand or antisense strand optionally comprises a phosphate group.

In another such embodiment, the DsiRNA comprises:

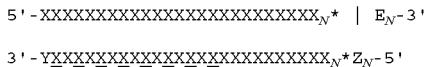

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "E"=DNA, RNA, or modified nucleotide, "|"=a discontinuity, and "N"=1 to 50 or more, but is optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

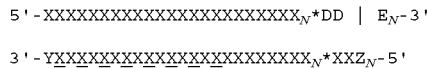

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

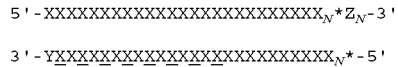

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

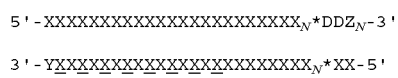

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In one embodiment, a extended DsiRNA agent is provided that comprises deoxyribonucleotides positioned at sites modeled to function via specific direction of Dicer cleavage. An exemplary structure for such a molecule is shown:

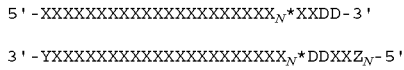

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

The above structure is modeled to force Dicer to cleave a maximum of a 21mer duplex as its primary post-processing form. In embodiments where the bottom strand of the above structure is the antisense strand, the positioning of two deoxyribonucleotide residues at the ultimate and penultimate residues of the 5' end of the antisense strand is likely to reduce off-target effects (as prior studies have shown a 2'-O-methyl modification of at least the penultimate position from the 5' terminus of the antisense strand to reduce off-target effects; see, e.g., US 2007/0223427).

In a related embodiment, the DsiRNA comprises:

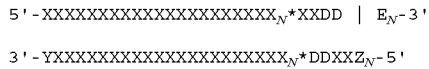

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In a related embodiment, the DsiRNA comprises:

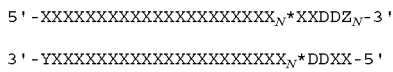

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA, RNA, or modified nucleotide, and "N"=1 to 50 or more, but is optionally 1-30 or, optionally 1-15 or, optionally, 1-10. "N*"=0 to 15 or more, but is optionally 0, 1, 2, 3, 4, or 5. In one embodiment, the top strand is the sense strand, and the bottom strand is the antisense strand. Alternatively, the bottom strand is the sense strand and the top strand is the antisense strand.

In any of the above-depicted structures, the 5' end of either the sense strand or antisense strand optionally comprises a phosphate group.

In one embodiment, the present invention provides a double stranded nucleic acid having a substantially duplexed region between the first and second strands comprising a fully duplexed region having no unpaired bases between the 5' terminal and 3' terminal nucleotides of the first strand that are paired with corresponding nucleotides of the second strand. In another embodiment, the present invention provides a double stranded nucleic acid having a substantially duplexed region comprising, between the 5' terminal and 3' terminal nucleotides of the first strand that are paired with corresponding nucleotides of the second strand, 1 unpaired base pair, 2 unpaired base pairs, 3 unpaired base pairs, 4 unpaired base pairs, and 5 unpaired base pairs. In some embodiments, the unpaired base pairs are consecutive. In other embodiments, the unpaired base pairs are non-consecutive.

As used herein "DsiRNAmm" refers to a DsiRNA having a "mismatch tolerant region" containing one, two, three or four mismatched base pairs of the duplex formed by the sense and antisense strands of the DsiRNA, where such mismatches are positioned within the DsiRNA at a location(s) lying between (and thus not including) the two terminal base pairs of either end of the double stranded region of the DsiRNA. The mismatched base pairs are located within a "mismatch-tolerant region" which is defined herein with respect to the location of the projected Ago2 cut site of the corresponding target nucleic acid. The mismatch tolerant region is located "upstream of" the projected Ago2 cut site of the target strand. "Upstream" in this context will be understood as the 5'-most portion of the DsiRNAmm duplex, where 5' refers to the orientation of the sense strand of the DsiRNA duplex. Therefore, the mismatch tolerant region is upstream of the base on the sense (passenger) strand that corresponds to the projected Ago2 cut site of the target nucleic acid; alternatively, when referring to the antisense (guide) strand of the DsiRNAmm, the mismatch tolerant region can also be described as positioned downstream of the base that is complementary to the projected Ago2 cut site of the target nucleic acid, that is, the 3'-most portion of the antisense strand of the DsiRNAmm (where position 1 of the antisense strand is the 5' terminal nucleotide of the antisense strand).

In one embodiment, for example, the mismatch tolerant region is positioned between and including base pairs 3-9 when numbered from the nucleotide starting at the 5' end of the sense strand of the duplex. Therefore, a DsiRNAmm of the invention possesses a single mismatched base pair at any one of positions 3, 4, 5, 6, 7, 8 or 9 of the sense strand of a right-hand extended DsiRNA (where position 1 is the 5' terminal nucleotide of the sense strand and position 9 is the nucleotide residue of the sense strand that is immediately 5' of the projected Ago2 cut site of the target RNA sequence corresponding to the sense strand sequence). In certain embodiments, for a DsiRNAmm that possesses a mismatched base pair nucleotide at any of positions 3, 4, 5, 6, 7, 8 or 9 of the sense strand, the corresponding mismatched base pair nucleotide of the antisense strand not only forms a mismatched base pair with the DsiRNAmm sense strand sequence, but also forms a mismatched base pair with a DsiRNAmm target RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet base pairs with its corresponding target RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target RNA sequence).

A DsiRNAmm of the invention that possesses a single mismatched base pair within the mismatch-tolerant region (mismatch region) as described above (e.g., a DsiRNAmm harboring a mismatched nucleotide residue at any one of positions 3, 4, 5, 6, 7, 8 or 9 of the sense strand) can further include one, two or even three additional mismatched base pairs. In preferred embodiments, these one, two or three additional mismatched base pairs of the DsiRNAmm occur at position(s) 3, 4, 5, 6, 7, 8 and/or 9 of the sense strand (and at corresponding residues of the antisense strand). In one embodiment where one additional mismatched base pair is present within a DsiRNAmm, the two mismatched base pairs of the sense strand can occur, e.g., at nucleotides of both position 4 and position 6 of the sense strand (with mismatch also occurring at corresponding nucleotide residues of the antisense strand).

In DsiRNAmm agents possessing two mismatched base pairs, mismatches can occur consecutively (e.g., at consecutive positions along the sense strand nucleotide sequence). Alternatively, nucleotides of the sense strand that form mismatched base pairs with the antisense strand sequence can be interspersed by nucleotides that base pair with the antisense strand sequence (e.g., for a DsiRNAmm possessing mismatched nucleotides at positions 3 and 6, but not at positions 4 and 5, the mismatched residues of sense strand positions 3 and 6 are interspersed by two nucleotides that form matched base pairs with corresponding residues of the antisense strand). For example, two residues of the sense strand (located within the mismatch-tolerant region of the sense strand) that form mismatched base pairs with the corresponding antisense strand sequence can occur with zero, one, two, three, four or five matched base pairs located between these mismatched base pairs.

For certain DsiRNAmm agents possessing three mismatched base pairs, mismatches can occur consecutively (e.g., in a triplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 4 and 8, but not at positions 5, 6 and 7, the mismatched residues of sense strand positions 3 and 4 are adjacent to one another, while the mismatched residues of sense strand positions 4 and 8 are interspersed by three nucleotides that form matched base pairs with corresponding residues of the antisense strand). For example, three residues of the sense strand (located within the mismatch-tolerant region of the sense strand) that form mismatched base pairs with the corresponding antisense strand sequence can occur with zero, one, two, three or four matched base pairs located between any two of these mismatched base pairs.

For certain DsiRNAmm agents possessing four mismatched base pairs, mismatches can occur consecutively (e.g., in a quadruplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 5, 7 and 8, but not at positions 4 and 6, the mismatched residues of sense strand positions 7 and 8 are adjacent to one another, while the mismatched residues of sense strand positions 3 and 5 are interspersed by one nucleotide that forms a matched base pair with the corresponding residue of the antisense strand—similarly, the mismatched residues of sense strand positions 5 and 7 are also interspersed by one nucleotide that forms a matched base pair with the corresponding residue of the antisense strand). For example, four residues of the sense strand (located within the mismatch-tolerant region of the sense strand) that form mismatched base pairs with the corresponding antisense strand sequence can occur with zero, one, two or three matched base pairs located between any two of these mismatched base pairs.

In another embodiment, a DsiRNAmm of the invention comprises a mismatch tolerant region which possesses a single mismatched base pair nucleotide at any one of positions 13, 14, 15, 16, 17, 18, 19, 20 or 21 of the antisense strand of a left-hand extended DsiRNA (where position 1 is the 5' terminal nucleotide of the antisense strand and position 13 is the nucleotide residue of the antisense strand that is immediately 3' (downstream) in the antisense strand of the projected Ago2 cut site of the target RNA sequence sufficiently complementary to the antisense strand sequence). In certain embodiments, for a DsiRNAmm that possesses a mismatched base pair nucleotide at any of positions 13, 14, 15, 16, 17, 18, 19, 20 or 21 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet base pairs with its corresponding target RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target RNA sequence).

A DsiRNAmm of the invention that possesses a single mismatched base pair within the mismatch-tolerant region as described above (e.g., a DsiRNAmm harboring a mismatched nucleotide residue at positions 13, 14, 15, 16, 17, 18, 19, 20 or 21 of the antisense strand) can further include one, two or even three additional mismatched base pairs. In preferred embodiments, these one, two or three additional mismatched base pairs of the DsiRNAmm occur at position(s) 13, 14, 15, 16, 17, 18, 19, 20 and/or 21 of the antisense strand (and at corresponding residues of the sense strand). In one embodiment where one additional mismatched base pair is present within a DsiRNAmm, the two mismatched base pairs of the antisense strand can occur, e.g., at nucleotides of both position 14 and position 18 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 13 and 16, but not at positions 14 and 15, the mismatched residues of antisense strand positions 13 and 16 are interspersed by two nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 13, 14 and 18, but not at positions 15, 16 and 17, the mismatched residues of antisense strand positions 13 and 14 are adjacent to one another, while the mismatched residues of antisense strand positions 14 and 18 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 13, 15, 17 and 18, but not at positions 14 and 16, the mismatched residues of antisense strand positions 17 and 18 are adjacent to one another, while the mismatched residues of antisense strand positions 13 and 15 are interspersed by one nucleotide that forms a matched base pair with the corresponding residue of the sense strand—similarly, the mismatched residues of antisense strand positions 15 and 17 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

In a further embodiment, a DsiRNAmm of the invention possesses a single mismatched base pair nucleotide at any one of positions 11, 12, 13, 14, 15, 16, 17, 18 or 19 of the antisense strand of a left-hand extended DsiRNA (where position 1 is the 5' terminal nucleotide of the antisense strand and position 11 is the nucleotide residue of the antisense strand that is immediately 3' (downstream) in the antisense strand of the projected Ago2 cut site of the target RNA sequence sufficiently complementary to the antisense strand sequence). In certain embodiments, for a DsiRNAmm that possesses a mismatched base pair nucleotide at any of positions 11, 12, 13, 14, 15, 16, 17, 18 or 19 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet this same antisense strand nucleotide base pairs with its corresponding target RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target RNA sequence).

A DsiRNAmm of the invention that possesses a single mismatched base pair within the mismatch-tolerant region as described above (e.g., a DsiRNAmm harboring a mismatched nucleotide residue at positions 11, 12, 13, 14, 15, 16, 17, 18 or 19 of the antisense strand) can further include one, two or even three additional mismatched base pairs. In preferred embodiments, these one, two or three additional mismatched base pairs of the DsiRNAmm occur at position(s) 11, 12, 13, 14, 15, 16, 17, 18 and/or 19 of the antisense strand (and at corresponding residues of the sense strand). In one embodiment where one additional mismatched base pair is present within a DsiRNAmm, the two mismatched base pairs of the antisense strand can occur, e.g., at nucleotides of both position 14 and position 18 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 12 and 15, but not at positions 13 and 14, the mismatched residues of antisense strand positions 12 and 15 are interspersed by two nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 13, 14 and 18, but not at positions 15, 16 and 17, the mismatched residues of antisense strand positions 13 and 14 are adjacent to one another, while the mismatched residues of antisense strand positions 14 and 18 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 13, 15, 17 and 18, but not at positions 14 and 16, the mismatched residues of antisense strand positions 17 and 18 are adjacent to one another, while the mismatched residues of antisense strand positions 13 and 15 are interspersed by one nucleotide that forms a matched base pair with the corresponding residue of the sense strand—similarly, the mismatched residues of antisense strand positions 15 and 17 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

In an additional embodiment, a DsiRNAmm of the invention possesses a single mismatched base pair nucleotide at any one of positions 15, 16, 17, 18, 19, 20, 21, 22 or 23 of the antisense strand of a left-hand extended DsiRNA (where position 1 is the 5' terminal nucleotide of the antisense strand and position 15 is the nucleotide residue of the antisense strand that is immediately 3' (downstream) in the antisense strand of the projected Ago2 cut site of the target RNA sequence sufficiently complementary to the antisense strand sequence). In certain embodiments, for a DsiRNAmm that possesses a mismatched base pair nucleotide at any of positions 15, 16, 17, 18, 19, 20, 21, 22 or 23 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet this same antisense strand nucleotide base pairs with its corresponding target RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target RNA sequence).

A DsiRNAmm of the invention that possesses a single mismatched base pair within the mismatch-tolerant region as described above (e.g., a DsiRNAmm harboring a mismatched nucleotide residue at positions 15, 16, 17, 18, 19, 20, 21, 22 or 23 of the antisense strand) can further include one, two or even three additional mismatched base pairs. In preferred embodiments, these one, two or three additional mismatched base pairs of the DsiRNAmm occur at position(s) 15, 16, 17, 18, 19, 20, 21, 22 and/or 23 of the antisense strand (and at corresponding residues of the sense strand). In one embodiment where one additional mismatched base pair is present within a DsiRNAmm, the two mismatched base pairs of the antisense strand can occur, e.g., at nucleotides of both position 16 and position 20 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 16 and 20, but not at positions 17, 18 and 19, the mismatched residues of antisense strand positions 16 and 20 are interspersed by three nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 16, 17 and 21, but not at positions 18, 19 and 20, the mismatched residues of antisense strand positions 16 and 17 are adjacent to one another, while the mismatched residues of antisense strand positions 17 and 21 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 17, 19, 21 and 22, but not at positions 18 and 20, the mismatched residues of antisense strand positions 21 and 22 are adjacent to one another, while the mismatched residues of antisense strand positions 17 and 19 are interspersed by one nucleotide that forms a matched base pair with the corresponding residue of the sense strand—similarly, the mismatched residues of antisense strand positions 19 and 21 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

For reasons of clarity, the location(s) of mismatched nucleotide residues within the above DsiRNAmm agents are numbered in reference to the 5' terminal residue of either sense or antisense strands of the DsiRNAmm. The numbering of positions located within the mismatch-tolerant region (mismatch region) of the antisense strand can shift with variations in the proximity of the 5' terminus of the antisense strand to the projected Ago2 cleavage site. Thus, the location(s) of preferred mismatch sites within either antisense strand or sense strand can also be identified as the permissible proximity of such mismatches to the projected Ago2 cut site. Accordingly, in one preferred embodiment, the position of a mismatch nucleotide of the sense strand of a DsiRNAmm is the nucleotide residue of the sense strand that is located immediately 5' (upstream) of the projected Ago2 cleavage site of the corresponding target RNA sequence. In other preferred embodiments, a mismatch nucleotide of the sense strand of a DsiRNAmm is positioned at the nucleotide residue of the sense strand that is located two nucleotides 5' (upstream) of the projected Ago2 cleavage site, three nucleotides 5' (upstream) of the projected Ago2 cleavage site, four nucleotides 5' (upstream) of the projected Ago2 cleavage site, five nucleotides 5' (upstream) of the projected Ago2 cleavage site, six nucleotides 5' (upstream) of the projected Ago2 cleavage site, seven nucleotides 5' (upstream) of the projected Ago2 cleavage site, eight nucleotides 5' (upstream) of the projected Ago2 cleavage site, or nine nucleotides 5' (upstream) of the projected Ago2 cleavage site.

Exemplary single mismatch-containing, 5' guide single strand extended DsiRNAs (DsiRNAmm) include the following structures (such mismatch-containing structures may also be incorporated into other exemplary DsiRNA structures shown herein).

```
5'-XX^MXXXXXXXXXXXXXXXXXXXX_N*DD-3'
3'-YXX_MXXXXXXXXXXXXXXXXXXXX_N*XXZ_N-5'

5'-XXX^MXXXXXXXXXXXXXXXXXXX_N*DD-3'
3'-YXXX_MXXXXXXXXXXXXXXXXXXX_N*XXZ_N-5'

5'-XXXX^MXXXXXXXXXXXXXXXXXX_N*DD-3'
3'-YXXXX_MXXXXXXXXXXXXXXXXXX_N*XXZ_N-5'

5'-XXXXX^MXXXXXXXXXXXXXXXXX_N*DD-3'
3'-YXXXXX_MXXXXXXXXXXXXXXXXX_N*XXZ_N-5'

5'-XXXXXX^MXXXXXXXXXXXXXXXX_N*DD-3'
3'-YXXXXXX_MXXXXXXXXXXXXXXXX_N*XXZ_N-5'

5'-XXXXXXX^MXXXXXXXXXXXXXXX_N*DD-3'
3'-YXXXXXXX_MXXXXXXXXXXXXXXX_N*XXZ_N-5'

5'-XXXXXXXX^MXXXXXXXXXXXXXX_N*DD-3'
3'-YXXXXXXXX_MXXXXXXXXXXXXXX_N*XXZ_N-5'
``` wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, "N"=1 to 50 or more, but is optionally 1-30 or, optionally 1-15 or, optionally, 1-10. "N*"=0 to 15 or more, but is optionally 0, 1, 2, 3, 4, or 5, and "D"=DNA, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNAmm agents. For the above mismatch structures, the top strand is the sense strand, and the bottom strand is the antisense strand.

In certain embodiments, a DsiRNA of the invention can contain mismatches that exist in reference to the target RNA sequence yet do not necessarily exist as mismatched base pairs within the two strands of the DsiRNA—thus, a DsiRNA can possess perfect complementarity between first and second strands of a DsiRNA, yet still possess mismatched residues in reference to a target RNA (which, in certain embodiments, may be advantageous in promoting efficacy and/or potency and/or duration of effect). In certain embodiments, where mismatches occur between antisense strand and target RNA sequence, the position of a mismatch is located within the antisense strand at a position(s) that corresponds to a sequence of the sense strand located 5' of the projected Ago2 cut site of the target region—e.g., antisense strand residue(s) positioned within the antisense strand to the 3' of the antisense residue which is complementary to the projected Ago2 cut site of the target sequence.

Exemplary 25/27mer DsiRNAs that harbor a single mismatched residue in reference to target sequences include the following preferred structures.

```
Target RNA Sequence:
5'-  . . . AXXXXXXXXXXXXXXXXXXXX . . . -3'

DsiRNAmm Sense Strand:
5'-XXXXXXXXXXXXXXXXXXXXXXXXX_N*DD-3'

DsiRNAmm Antisense Strand:
3'-EXXXXXXXXXXXXXXXXXXXXXXXX_N*XXZ_N-5'

Target RNA Sequence:
5'-  . . . XAXXXXXXXXXXXXXXXXXXX . . . -3'

DsiRNAmm Sense Strand:
5'-XXXXXXXXXXXXXXXXXXXXXXXXX_N*DD-3'

DsiRNAmm Antisense Strand:
3'-XEXXXXXXXXXXXXXXXXXXXXXXX_N*XXZ_N-5'

Target RNA Sequence:
5'-  . . . AXXXXXXXXXXXXXXXXXXX . . . -3'

DsiRNAmm Sense Strand:
5'-BXXXXXXXXXXXXXXXXXXXXXXXX_N*DD-3'

DsiRNAmm Antisense Strand:
3'-XXEXXXXXXXXXXXXXXXXXXXXXX_N*XXZ_N-5'

Target RNA Sequence:
5'-  . . . XAXXXXXXXXXXXXXXXXXX . . . -3'
```

-continued
```
DsiRNAmm Sense Strand:
5'-XBXXXXXXXXXXXXXXXXXXXX<sub>N</sub>*DD-3'

DsiRNAmm Antisense Strand:
3'-XXXEXXXXXXXXXXXXXXXXXXXXX<sub>N</sub>*XXZ<sub>N</sub>-5'

Target RNA Sequence:
5'- . . . XXAXXXXXXXXXXXXXX . . . -3'

DsiRNAmm Sense Strand:
5'-XXBXXXXXXXXXXXXXXXXXXXX<sub>N</sub>*DD-3'

DsiRNAmm Antisense Strand:
3'-XXXXEXXXXXXXXXXXXXXXXXXXX<sub>N</sub>*XXZ<sub>N</sub>-5'

Target RNA Sequence:
5'- . . . XXXAXXXXXXXXXXXXX . . . -3'

DsiRNAmm Sense Strand:
5'-XXXBXXXXXXXXXXXXXXXXXXXX<sub>N</sub>*DD-3'

DsiRNAmm Antisense Strand:
3'-XXXXXEXXXXXXXXXXXXXXXXXXXX<sub>N</sub>*XXZ<sub>N</sub>-5'

Target RNA Sequence:
5'- . . . XXXXAXXXXXXXXXXXX . . . -3'

DsiRNAmm Sense Strand:
5'-XXXXBXXXXXXXXXXXXXXXXXXX<sub>N</sub>*DD-3'

DsiRNAmm Antisense Strand:
3'-XXXXXXEXXXXXXXXXXXXXXXXXXXX<sub>N</sub>*XXZ<sub>N</sub>-5'

Target RNA Sequence:
5'- . . . XXXXXAXXXXXXXXXXX . . . -3'

DsiRNAmm Sense Strand:
5'-XXXXXBXXXXXXXXXXXXXXXXXXX<sub>N</sub>*DD-3'

DsiRNAmm Antisense Strand:
3'-XXXXXXXEXXXXXXXXXXXXXXXXXXXX<sub>N</sub>*XXZ<sub>N</sub>-5'

Target RNA Sequence:
5'- . . . XXXXXXAXXXXXXXXXXX . . . -3'

DsiRNAmm Sense Strand:
5'-XXXXXXBXXXXXXXXXXXXXXXXXXX<sub>N</sub>*DD-3'

DsiRNAmm Antisense Strand:
3'-XXXXXXXXEXXXXXXXXXXXXXXXXXXXX<sub>N</sub>*XXZ<sub>N</sub>-5'

Target RNA Sequence:
5'- . . . XXXXXXXAXXXXXXXXXX . . . -3'

DsiRNAmm Sense Strand:
5'-XXXXXXXBXXXXXXXXXXXXXXXXXXX<sub>N</sub>*DD-3'

DsiRNAmm Antisense Strand:
3'-XXXXXXXXXEXXXXXXXXXXXXXXXXXXXX<sub>N</sub>*XXZ<sub>N</sub>-5'

Target RNA Sequence:
5'- . . . XXXXXXXXAXXXXXXXXX . . . -3'

DsiRNAmm Sense Strand:
5'-XXXXXXXXBXXXXXXXXXXXXXXXXXXX<sub>N</sub>*DD-3'

DsiRNAmm Antisense Strand:
3'-XXXXXXXXXXEXXXXXXXXXXXXXXXXXXXX<sub>N</sub>*XXZ<sub>N</sub>-5'
``` wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "Z"=DNA, RNA, or modified nucleotide, "N"=1 to 50 or more, but is optionally 1-30 or, optionally 1-15 or, optionally, 1-10. "N*"=0 to 15 or more, but is optionally 0, 1, 2, 3, 4, or 5, "D"=DNA, "p"=a phosphate group, "E"=Nucleic acid residues (RNA, DNA or non-natural or modified nucleic acids) that do not base pair (hydrogen bond) with corresponding "A" RNA residues of otherwise complementary (target) strand when strands are annealed, yet optionally do base pair with corresponding "B" residues ("B" residues are also RNA, DNA or non-natural or modified nucleic acids). Any of the residues of such agents can optionally be 2'-O-methyl RNA monomers—e.g., alternating positioning of 2'-O-methyl RNA monomers that commences from the 3'-terminal residue of the bottom (second) strand, as shown above, or other patterns of 2'-O-methyl and/or other modifications as described herein can also be used in the above DsiRNA agents.

In addition to the above-exemplified structures, DsiRNAs of the invention can also possess one, two or three additional residues that form further mismatches with the target RNA sequence. Such mismatches can be consecutive, or can be interspersed by nucleotides that form matched base pairs with the target RNA sequence. Where interspersed by nucleotides that form matched base pairs, mismatched residues can be spaced apart from each other within a single strand at an interval of one, two, three, four, five, six, seven or even eight base paired nucleotides between such mismatch-forming residues.

As for the above-described DsiRNAmm agents, a preferred location within DsiRNAs for antisense strand nucleotides that form mismatched base pairs with target RNA sequence (yet may or may not form mismatches with corresponding sense strand nucleotides) is within the antisense strand region that is located 3' (downstream) of the antisense strand sequence which is complementary to the projected Ago2 cut site of the DsiRNA. Thus, in one preferred embodiment, the position of a mismatch nucleotide (in relation to the target RNA sequence) of the antisense strand of a DsiRNAmm is the nucleotide residue of the antisense strand that is located immediately 3' (downstream) within the antisense strand sequence of the projected Ago2 cleavage site of the corresponding target RNA sequence. In other preferred embodiments, a mismatch nucleotide of the antisense strand of a DsiRNAmm (in relation to the target RNA sequence) is positioned at the nucleotide residue of the antisense strand that is located two nucleotides 3' (downstream) of the corresponding projected Ago2 cleavage site, three nucleotides 3' (downstream) of the corresponding projected Ago2 cleavage site, four nucleotides 3' (downstream) of the corresponding projected Ago2 cleavage site, five nucleotides 3' (downstream) of the corresponding projected Ago2 cleavage site, six nucleotides 3' (downstream) of the projected Ago2 cleavage site, seven nucleotides 3' (downstream) of the projected Ago2 cleavage site, eight nucleotides 3' (downstream) of the projected Ago2 cleavage site, or nine nucleotides 3' (downstream) of the projected Ago2 cleavage site.

In DsiRNA agents possessing two mismatch-forming nucleotides of the antisense strand (where mismatch-forming nucleotides are mismatch forming in relation to target RNA sequence), mismatches can occur consecutively (e.g., at consecutive positions along the antisense strand nucleotide sequence). Alternatively, nucleotides of the antisense strand that form mismatched base pairs with the target RNA sequence can be interspersed by nucleotides that base pair with the target RNA sequence (e.g., for a DsiRNA possessing mismatch-forming nucleotides at positions 13 and 16 (starting from the 5' terminus (position 1) of the antisense strand), but not at positions 14 and 15, the mismatched residues of sense strand positions 13 and 16 are interspersed by two nucleotides that form matched base pairs with corresponding residues of the target RNA sequence). For example, two residues of the antisense strand (located within the mismatch-tolerant region of the antisense strand) that form mismatched base pairs with the corresponding target RNA sequence can occur with zero, one, two, three, four or five matched base pairs (with respect to target RNA sequence) located between these mismatch-forming base pairs.

For certain DsiRNAs possessing three mismatch-forming base pairs (mismatch-forming with respect to target RNA sequence), mismatch-forming nucleotides can occur consecutively (e.g., in a triplet along the antisense strand nucleotide sequence). Alternatively, nucleotides of the antisense strand that form mismatched base pairs with the target RNA sequence can be interspersed by nucleotides that form matched base pairs with the target RNA sequence (e.g., for a DsiRNA possessing mismatched nucleotides at positions 13, 14 and 18, but not at positions 15, 16 and 17, the mismatch-forming residues of antisense strand positions 13 and 14 are adjacent to one another, while the mismatch-forming residues of antisense strand positions 14 and 18 are interspersed by three nucleotides that form matched base pairs with corresponding residues of the target RNA). For example, three residues of the antisense strand (located within the mismatch-tolerant region of the antisense strand) that form mismatched base pairs with the corresponding target RNA sequence can occur with zero, one, two, three or four matched base pairs located between any two of these mismatch-forming base pairs.

For certain DsiRNAs possessing four mismatch-forming base pairs (mismatch-forming with respect to target RNA sequence), mismatch-forming nucleotides can occur consecutively (e.g., in a quadruplet along the sense strand nucleotide sequence). Alternatively, nucleotides of the antisense strand that form mismatched base pairs with the target RNA sequence can be interspersed by nucleotides that form matched base pairs with the target RNA sequence (e.g., for a DsiRNA possessing mismatch-forming nucleotides at positions 13, 15, 17 and 18, but not at positions 14 and 16, the mismatch-forming residues of antisense strand positions 17 and 18 are adjacent to one another, while the mismatch-forming residues of antisense strand positions 13 and 15 are interspersed by one nucleotide that forms a matched base pair with the corresponding residue of the target RNA sequence—similarly, the mismatch-forming residues of antisense strand positions 15 and 17 are also interspersed by one nucleotide that forms a matched base pair with the corresponding residue of the target RNA sequence). For example, four residues of the antisense strand (located within the mismatch-tolerant region of the antisense strand) that form mismatched base pairs with the corresponding target RNA sequence can occur with zero, one, two or three matched base pairs located between any two of these mismatch-forming base pairs.

The above DsiRNAmm and other DsiRNA structures are described in order to exemplify certain structures of DsiRNAmm and DsiRNA agents. Design of the above DsiRNAmm and DsiRNA structures can be adapted to generate, e.g., DsiRNAmm forms of a extended DsiRNA agent shown infra (including, e.g., design of mismatch-containing DsiRNAmm agents). As exemplified above, DsiRNAs can also be designed that possess single mismatches (or two, three or four mismatches) between the antisense strand of the DsiRNA and a target sequence, yet optionally can retain perfect complementarity between sense and antisense strand sequences of a DsiRNA.

It is further noted that the DsiRNA agents exemplified infra can also possess insertion/deletion (in/del) structures within their double-stranded and/or target RNA-aligned structures. Accordingly, the DsiRNAs of the invention can be designed to possess in/del variations in, e.g., antisense strand sequence as compared to target RNA sequence and/or antisense strand sequence as compared to sense strand sequence, with preferred location(s) for placement of such in/del nucleotides corresponding to those locations described above for positioning of mismatched and/or mismatch-forming base pairs.

In certain embodiments, the "D" residues of any of the above structures include at least one PS-DNA or PS-RNA. Optionally, the "D" residues of any of the above structures include at least one modified nucleotide that inhibits Dicer cleavage.

In one embodiment, the DsiRNA agent has an asymmetric structure, with the sense strand having a 25-base pair length, the antisense strand having a 42-nucleotide length with a 2 base 3'-overhang (and, therefore, the DsiRNA agent possesses a 5' overhang 15 nucleotides in length at the 3' end of the sense strand/5' end of the antisense strand), and with deoxyribonucleotides located at positions 24 and 25 of the sense strand (numbering from position 1 at the 5' of the sense strand) and each base paired with a cognate nucleotide of the antisense strand. The 5' overhang comprises a modified nucleotide, preferably a 2'-O-methyl ribonucleotide, and/or a phosphate backbone modification, preferably phosphorothioate.

In another embodiment, the DsiRNA agent has a structure, with the sense strand having a 40-nucleotide length, the antisense strand having a 27-nucleotide length with a 2 base 3'-overhang (and, therefore, the DsiRNA agent possesses a 3' overhang 15 nucleotides in length at the 3' end of the sense strand/5' end of the antisense strand), and with deoxyribonucleotides located at positions 24 and 25 of the sense strand (numbering from position 1 at the 5' of the sense strand) and each base paired with a cognate nucleotide of the antisense strand. The 3' overhang comprises a deoxyribonucleotide and/or a phosphate backbone modification, preferably methylphosphonate.

Modification of DsiRNAs

One major factor that inhibits the effect of double stranded RNAs ("dsRNAs") is the degradation of dsRNAs (e.g., siRNAs and DsiRNAs) by nucleases. A 3'-exonuclease is the primary nuclease activity present in serum and modification of the 3'-ends of antisense DNA oligonucleotides is crucial to prevent degradation (Eder et al., 1991). An RNase-T family nuclease has been identified called ERI-1 which has 3' to 5' exonuclease activity that is involved in regulation and degradation of siRNAs (Kennedy et al., 2004; Hong et al., 2005). This gene is also known as Thex1 (NM_02067) in mice or THEX1 (NM_153332) in humans and is involved in degradation of histone mRNA; it also mediates degradation of 3'-overhangs in siRNAs, but does not degrade duplex RNA (Yang et al., 2006). It is therefore reasonable to expect that 3'-end-stabilization of dsRNAs, including the DsiRNAs of the instant invention, will improve stability.

XRN1 (NM_019001) is a 5' to 3' exonuclease that resides in P-bodies and has been implicated in degradation of mRNA targeted by miRNA (Rehwinkel et al., 2005) and may also be responsible for completing degradation initiated by internal cleavage as directed by a siRNA. XRN2 (NM_012255) is a distinct 5' to 3' exonuclease that is involved in nuclear RNA processing. Although not currently implicated in degradation or processing of siRNAs and miRNAs, these both are known nucleases that can degrade RNAs and may also be important to consider.

RNase A is a major endonuclease activity in mammals that degrades RNAs. It is specific for ssRNA and cleaves at the 3'-end of pyrimidine bases. SiRNA degradation products consistent with RNase A cleavage can be detected by mass spectrometry after incubation in serum (Turner et al., 2007). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006). This suggests the possibility that lower stability regions of the duplex may "breathe" and offer transient single-stranded species available for degradation by RNase A. RNase A inhibitors can be added to serum and improve siRNA longevity and potency (Haupenthal et al., 2007).

In 21mers, phosphorothioate or boranophosphate modifications directly stabilize the internucleoside phosphate linkage. Boranophosphate modified RNAs are highly nuclease resistant, potent as silencing agents, and are relatively nontoxic. Boranophosphate modified RNAs cannot be manufactured using standard chemical synthesis methods and instead are made by in vitro transcription (IVT) (Hall et al., 2004 and Hall et al., 2006). Phosphorothioate (PS) modifications can be readily placed in an RNA duplex at any desired position and can be made using standard chemical synthesis methods, though the ability to use such modifications within an RNA duplex that retains RNA silencing activity can be limited.

In certain embodiments, the 5' single strand extended region of the guide strand or 3' single strand extended region of the passenger strand has at least one phosphorothioate backbone modification. In some embodiments, every linkage of the 5' single strand extended region of the guide strand or 3' single strand extended region of the passenger strand has a phosphorothioate backbone modification. In some embodiments, every linkage of the 5' single strand extended region of the guide strand has a phosphorothioate backbone modification except the linkage of the terminal 5' nucleotide of the guide strand. In certain embodiments, the 5' single strand extended region of the guide strand or 3' single strand extended region of the passenger strand has at least one methylphosphonate backbone modification. In some embodiments, every linkage of the 5' single strand extended region of the guide strand or 3' single strand extended region of the passenger strand has a methylphosphonate backbone modification. In some embodiments, every linkage of the 3' single strand extended region of the passenger strand has a phosphorothioate backbone modification except the terminal 5' nucleotide of the guide strand.

It is noted, however, that the PS modification shows dose-dependent toxicity, so most investigators have recommended limited incorporation in siRNAs, historically favoring the 3'-ends where protection from nucleases is most important (Harborth et al., 2003; Chiu and Rana, 2003; Braasch et al., 2003; Amarzguioui et al., 2003). More extensive PS modification can be compatible with potent RNAi activity; however, use of sugar modifications (such as 2'-O-methyl RNA) may be superior (Choung et al., 2006).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung et al., 2006; Czauderna et al., 2003).

The 21-fluoro (2'-F) modification is also compatible with dsRNA (e.g., siRNA and DsiRNA) function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005; Prakash et al., 2005; Kraynack and Baker, 2006) and can improve performance and extend duration of action when used in vivo (Morrissey et al., 2005a; Morrissey et al., 2005b). A highly potent, nuclease stable, blunt 19mer duplex containing alternative 2'-F and 21-O-Me bases is taught by Allerson. In this design, alternating 21-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 21-O-Me RNA and 2'-F RNA, this duplex includes DNA, RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004) employed a duplex in vivo and was mostly RNA with two 21-O-Me RNA bases and limited 3'-terminal PS internucleoside linkages.

Locked nucleic acids (LNAs) are a different class of 21-modification that can be used to stabilize dsRNA (e.g., siRNA and DsiRNA). Patterns of LNA incorporation that retain potency are more restricted than 2'-O-methyl or 2'-F bases, so limited modification is preferred (Braasch et al., 2003; Grunweller et al., 2003; Elmen et al., 2005). Even with limited incorporation, the use of LNA modifications can improve dsRNA performance in vivo and may also alter or improve off target effect profiles (Mook et al., 2007).

Synthetic nucleic acids introduced into cells or live animals can be recognized as "foreign" and trigger an immune response Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005; Schlee et al., 2006). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005b; Sioud and Sorensen, 2003; Sioud, 2005; Ma et al., 2005). RNAs transcribed within the cell are less immunogenic (Robbins et al., 2006) and synthetic RNAs that are immunogenic when delivered using lipid-based methods can evade immune stimulation when introduced unto cells by mechanical means, even in vivo (Heidel et al., 2004). However, lipid based delivery methods are convenient, effective, and widely used. Some general strategy to prevent immune responses is needed, especially for in vivo application where all cell types are present and the risk of generating an immune response is highest. Use of chemically modified RNAs may solve most or even all of these problems.

Although certain sequence motifs are clearly more immunogenic than others, it appears that the receptors of the innate immune system in general distinguish the presence or absence of certain base modifications which are more commonly found in mammalian RNAs than in prokaryotic RNAs. For example, pseudouridine, N6-methyl-A, and 2'-O-methyl modified bases are recognized as "self" and inclusion of these residues in a synthetic RNA can help evade immune detection (Kariko et al., 2005). Extensive 2'-modification of a sequence that is strongly immunostimulatory as unmodified RNA can block an immune response when administered to mice intravenously (Morrissey et al., 2005b). However, extensive modification is not needed to escape immune detection and substitution of as few as two 2'-O-methyl bases in a single strand of a siRNA duplex can be sufficient to block a type 1 IFN response both in vitro and in vivo; modified U and G bases are most effective (Judge et al., 2006). As an added benefit, selective incorporation of 2'-O-methyl bases can reduce the magnitude of off-target effects (Jackson et al., 2006). Use of 2'-O-methyl bases should therefore be considered for all dsRNAs intended for in vivo applications as a means of blocking immune responses and has the added benefit of improving nuclease stability and reducing the likelihood of off-target effects.

Although cell death can result from immune stimulation, assessing cell viability is not an adequate method to monitor induction of IFN responses. IFN responses can be present without cell death, and cell death can result from target knockdown in the absence of IFN triggering (for example, if the targeted gene is essential for cell viability). Relevant cytokines can be directly measured in culture medium and a variety of commercial kits exist which make performing such assays routine. While a large number of different immune effector molecules can be measured, testing levels of IFN-α, TNF-α, and IL-6 at 4 and 24 hours post transfection is usually sufficient for screening purposes. It is important to include a "transfection reagent only control" as cationic lipids can trigger immune responses in certain cells in the absence of any nucleic acid cargo. Including controls for IFN pathway induction should be considered for cell culture work. It is essential to test for immune stimulation whenever administering nucleic acids in vivo, where the risk of triggering IFN responses is highest.

Modifications can be included in the DsiRNA agents of the present invention so long as the modification does not prevent the DsiRNA agent from serving as a substrate for Dicer. Indeed, one surprising finding of the instant invention is that a 5' extended single stranded nucleotide region of the antisense strand or 3' extended single stranded nucleotide region of the sense strand can be attached to previously described DsiRNA molecules, resulting in enhanced RNAi efficacy and duration, provided that such extension is performed in a region of the extended molecule that does not interfere with Dicer processing (e.g., 3' of the Dicer cleavage site of the sense strand/5' of the Dicer cleavage site of the antisense strand). In one embodiment, one or more modifications are made that enhance Dicer processing of the DsiRNA agent. In a second embodiment, one or more modifications are made that result in more effective RNAi generation. In a third embodiment, one or more modifications are made that support a greater RNAi effect. In a fourth embodiment, one or more modifications are made that result in greater potency per each DsiRNA agent molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind, any number and combination of modifications can be incorporated into the DsiRNA agent. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, locked nucleic acids (LNA), morpholino, bicyclic furanose analogs and the like. Examples of modifications contemplated for the sugar moiety include 2'-alkyl pyrimidine, such as 2'-O-methyl, 21-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1. Other modifications are disclosed in Herdewijn (2000), Eckstein (2000), Rusckowski et al. (2000), Stein et al. (2001); Vorobjev et al. (2001).

One or more modifications contemplated can be incorporated into either strand. The placement of the modifications in the DsiRNA agent can greatly affect the characteristics of the DsiRNA agent, including conferring greater potency and stability, reducing toxicity, enhance Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that comprises 2'-O-methyl modified nucleotides. The antisense strand could also include additional 2'-O-methyl modified nucleotides.

In certain embodiments, the 5' single strand extended region of the guide strand, 3' single strand extended region of the passenger strand, or 5' single strand extended region of the passenger strand has at least one modified nucleotide, optionally a 2'-O-methyl ribonucleotide. In some embodiments, every nucleotide of the 5' single strand extended region of the guide strand or 3' single strand extended region of the passenger strand is a modified ribonucleotide, optionally a 2'-O-methyl ribonucleotide. In certain embodiments, an oligonucleotide complementary to the 5' single strand extended region of the guide strand has at least one modified nucleotide, optionally a 2'-O-methyl ribonucleotide. In some embodiments, every nucleotide of an oligonucleotide complementary to the 5' single strand extended region of the guide strand is a modified nucleotide, optionally a 2'-O-methyl ribonucleotide.

In certain embodiments of the present invention, the DsiRNA agent has one or more properties which enhance its processing by Dicer. According to these embodiments, the DsiRNA agent has a length sufficient such that it is processed by Dicer to produce an active siRNA and at least one of the following properties: (i) the DsiRNA agent is asymmetric, e.g., has a 3' overhang on the antisense strand and (ii) the DsiRNA agent has a modified 3' end on the sense strand to direct orientation of Dicer binding and processing of the dsRNA region to an active siRNA. In certain such embodiments, the presence of one or more base paired deoxyribonucleotides in a region of the sense strand that is 3' to the projected site of Dicer enzyme cleavage and corresponding region of the antisense strand that is 5' of the projected site of Dicer enzyme cleavage can also serve to orient such a molecule for appropriate directionality of Dicer enzyme cleavage.

In certain embodiments, the length of the 5' single stranded antisense extended region (5' antisense extension) or 3' single stranded sense extended region (3' sense extension) is 1-30 nucleotides, optionally 1-15 nucleotides, preferably 10-15 nucleotides, more preferably 11-15 nucleotides. Thus, a single stranded extended DsiRNA of the instant invention may possess a single strand extended region at the 5' terminus of a antisense/guide strand or at the 3' terminus of a sense/passenger strand that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more (e.g., 31, 32, 33, 34, 35, 36, 37, 38, 39, 40 or more) nucleotides in length.

In some embodiments, the longest strand in the double stranded nucleic acid comprises 36-66 nucleotides. In one embodiment, the DsiRNA agent has a structure such that the 5' end of the antisense strand overhangs the 3' end of the sense strand, the 3' end of the antisense strand overhangs the 5' end of the sense strand. In certain embodiments, the 5' overhang of the antisense strand is 1-30 nucleotides, and optionally is 10-30 nucleotides, for example 15 nucleotides. In another embodiment, the DsiRNA agent has a structure such that the 3' end of the sense strand overhangs the 5' end of the antisense strand, and the 3' end of the antisense strand overhangs the 5' end of the sense strand. In certain embodiments, the 3' overhang of the sense strand is 1-30 nucleotides, and optionally is 10-30 nucleotides, for example 15 nucleotides. In certain embodiments, the 3' overhang of the antisense strand is 1-10 nucleotides, and optionally is 1-6 nucleotides, preferably 1-4 nucleotides, for example 2 nucleotides. In another embodiment, the DsiRNA agent has a structure such that the 5' end of the sense strand overhangs the 3' end of the antisense strand. In certain embodiments, the 5' overhang of the sense strand is 4-30 nucleotides, and optionally is 10-30 nucleotides, for example 15 nucleotides. Both the sense and the antisense strand may also have a 5' phosphate.

In certain embodiments, the sense strand of a DsiRNA of the invention has a total length of between 25 nucleotides and 30 or more nucleotides (e.g., the sense strand possesses a length of 25, 26, 27, 28, 29, 30 or more (e.g., 31, 32, 33, 34, 35, 36, 37, 38, 39, 40 or more) nucleotides). In certain embodiments, the length of the sense strand is between 25 nucleotides and 30 nucleotides, optionally between 26 and 30 nucleotides, or, optionally, between 27 and 30 nucleotides in length. In related embodiments, the antisense strand has a length of between 36 and 66 or more nucleotides (e.g., the sense strand possesses a length of 236, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 or more (e.g., 67, 28, 69, 70, 71, 72, 73, 74, 75, 76, 77, 78, 79, 80 or more) nucleotides). In certain such embodiments, the antisense strand has a length of between 37 and 57 nucleotides in length, or between 37 and 52 nucleotides in length, or between 37 and 47 nucleotides in length, or between 42 and 62 nucleotides in length, or between 42 and 57 nucleotides in length, or between 42 and 47 nucleotides in length.

In certain embodiments, the sense strand of a DsiRNA of the invention has a total length of between 25 nucleotides and 60 or more nucleotides (e.g., the sense strand possesses a length of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more (e.g., 61, 62, 63, 64, 65, 66, 67, 68, 69, 70 or more) nucleotides). In certain embodiments, the length of the sense strand is between 25 nucleotides and 30 nucleotides, optionally between 35 and 55 nucleotides, or, optionally, between 40 and 55 nucleotides in length, or, optionally, between 40 and 60 nucleotides in length, or, optionally, between 45 and 60 nucleotides in length. In related embodiments, the antisense strand has a length of between 25 and 36 or more nucleotides (e.g., the sense strand possesses a length of 25, 27, 28, 29, 30, 31, 32, 33, 34, 35, 36, or more (e.g., 37, 38, 39, 40, 41, 42, 43, 44, 45, 46, 47, 48, 49, 50 or more) nucleotides). In certain such embodiments, the antisense strand has a length of between 27 and 32 nucleotides in length.

In certain embodiments, the presence of one or more base paired deoxyribonucleotides in a region of the sense strand that is 3' of the projected site of Dicer enzyme cleavage and corresponding region of the antisense strand that is 5' of the projected site of Dicer enzyme cleavage can serve to direct Dicer enzyme cleavage of such a molecule. While certain exemplified agents of the invention possess a sense strand deoxyribonucleotide that is located at position 24 or more 3' when counting from position 1 at the 5' end of the sense strand, and having this position 24 or more 3' deoxyribonucleotide of the sense strand base pairing with a cognate deoxyribonucleotide of the antisense strand, in some embodiments, it is also possible to direct Dicer to cleave a shorter product, e.g., a 19mer or a 20mer via inclusion of deoxyribonucleotide residues at, e.g., position 20 of the sense strand. Such a position 20 deoxyribonucleotide base pairs with a corresponding deoxyribonucleotide of the antisense strand, thereby directing Dicer-mediated excision of a 19mer as the most prevalent Dicer product (it is noted that the antisense strand can also comprise one or two deoxyribonucleotide residues immediately 3' of the antisense residue that base pairs with the position 20 deoxyribonucleotide residue of the sense strand in such embodiments, to further direct Dicer cleavage of the antisense strand). In such embodiments, the double-stranded DNA region (which is inclusive of modified nucleic acids that block Dicer cleavage) will generally possess a length of greater than 1 or 2 base pairs (e.g., 3 to 5 base pairs or more), in order to direct Dicer cleavage to generate what is normally a non-preferred length of Dicer cleavage product. A parallel approach can also be taken to direct Dicer excision of 20mer siRNAs, with the positioning of the first deoxyribonucleotide residue of the sense strand (when surveying the sense strand from position 1 at the 5' terminus of the sense strand) occurring at position 21.

In certain embodiments, the sense strand of the DsiRNA agent is modified for Dicer processing by suitable modifiers located at the 3' end of the sense strand, i.e., the DsiRNA agent is designed to direct orientation of Dicer binding and processing via sense strand modification. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the DsiRNA agent to direct the orientation of Dicer processing of the antisense strand. In a further embodiment of the present invention, two terminal DNA bases are substituted for two ribonucleotides on the 3'-end of the sense strand forming a blunt end of the duplex on the 3' end of the sense strand and the 5' end of the antisense strand, and a two-nucleotide RNA overhang is located on the 3'-end of the antisense strand. This is an asymmetric composition with DNA on the blunt end and RNA bases on the overhanging end. In certain embodiments of the instant invention, the modified nucleotides (e.g., deoxyribonucleotides) of the penultimate and ultimate positions of the 3' terminus of the sense strand base pair with corresponding modified nucleotides (e.g., deoxyribonucleotides) of the antisense strand (optionally, the penultimate and ultimate residues of the 5' end of the antisense strand in those DsiRNA agents of the instant invention possessing a blunt end at the 3' terminus of the sense strand/5' terminus of the antisense strand).

The sense and antisense strands of a DsiRNA agent of the instant invention anneal under biological conditions, such as the conditions found in the cytoplasm of a cell. In addition, a region of one of the sequences, particularly of the antisense strand, of the DsiRNA agent has a sequence length of at least 19 nucleotides, wherein these nucleotides are in the 21-nucleotide region adjacent to the 3' end of the antisense strand and are sufficiently complementary to a nucleotide sequence of the RNA produced from the target gene to anneal with and/or decrease levels of such a target RNA.

The DsiRNA agent of the instant invention may possess one or more deoxyribonucleotide base pairs located at any positions of sense and antisense strands that are located 3' of the projected Dicer cleavage site of the sense strand and 5' of the projected Dicer cleavage site of the antisense strand. In certain embodiments, one, two, three or all four of positions 24-27 of the sense strand (starting from position 1 at the 5' terminus of the sense strand) are deoxyribonucleotides, each deoxyribonucleotide of which base pairs with a corresponding deoxyribonucleotide of the antisense strand. In certain embodiments, the deoxyribonucleotides of the 5' region of the antisense strand (e.g., the region of the antisense strand located 5' of the projected Dicer cleavage site for a given DsiRNA molecule) are not complementary to the target RNA to which the DsiRNA agent is directed. In related embodiments, the entire region of the antisense strand located 5' of the projected Dicer cleavage site of a DsiRNA agent is not complementary to the target RNA to which the DsiRNA agent is directed. In certain embodiments, the deoxyribonucleotides of the antisense strand or the entire region of the antisense strand that is located 5' of the projected Dicer cleavage site of the DsiRNA agent is not sufficiently complementary to the target RNA to enhance annealing of the antisense strand of the DsiRNA to the target RNA when the antisense strand is annealed to the target RNA under conditions sufficient to allow for annealing between the antisense strand and the target RNA (e.g., a "core" antisense strand sequence lacking the DNA-extended region anneals equally well to the target RNA as the same "core" antisense strand sequence also extended with sequence of the DNA-extended region).

The DsiRNA agent may also have one or more of the following additional properties: (a) the antisense strand has a right or left shift from the typical 21mer, (b) the strands may not be completely complementary, i.e., the strands may contain simple mismatch pairings and (c) base modifications such as locked nucleic acid(s) may be included in the 5' end of the sense strand. A "typical" 21mer siRNA is designed using conventional techniques. In one technique, a variety of sites are commonly tested in parallel or pools containing several distinct siRNA duplexes specific to the same target with the hope that one of the reagents will be effective (Ji et al., 2003). Other techniques use design rules and algorithms to increase the likelihood of obtaining active RNAi effector molecules (Schwarz et al., 2003; Khvorova et al., 2003; Ui-Tei et al., 2004; Reynolds et al., 2004; Krol et al., 2004; Yuan et al., 2004; Boese et al., 2005). High throughput selection of siRNA has also been developed (U.S. published patent application No. 2005/0042641 A1). Potential target sites can also be analyzed by secondary structure predictions (Heale et al., 2005). This 21mer is then used to design a right shift to include 3-9 additional nucleotides on the 5' end of the 21mer. The sequence of these additional nucleotides may have any sequence. In one embodiment, the added ribonucleotides are based on the sequence of the target gene. Even in this embodiment, full complementarity between the target sequence and the antisense siRNA is not required.

The first and second oligonucleotides of a DsiRNA agent of the instant invention are not required to be completely complementary. They only need to be substantially complementary to anneal under biological conditions and to provide a substrate for Dicer that produces a siRNA sufficiently complementary to the target sequence. Locked nucleic acids, or LNA's, are well known to a skilled artisan (Elman et al., 2005; Kurreck et al., 2002; Crinelli et al., 2002; Braasch and Corey, 2001; Bondensgaard et al., 2000; Wahlestedt et al., 2000). In one embodiment, an LNA is incorporated at the 5' terminus of the sense strand. In another embodiment, an LNA is incorporated at the 5' terminus of the sense strand in duplexes designed to include a 3' overhang on the antisense strand.

In certain embodiments, the DsiRNA agent of the instant invention has an asymmetric structure, with the sense strand having a 27-base pair length, and the antisense strand having a 29-base pair length with a 2 base 3'-overhang. Such agents optionally may possess between one and four deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In other embodiments, the sense strand has a 28-base pair length, and the antisense strand has a 30-base pair length with a 2 base 3'-overhang. Such agents optionally may possess between one and five deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In additional embodiments, the sense strand has a 29-base pair length, and the antisense strand has a 31-base pair length with a 2 base 3'-overhang. Such agents optionally possess between one and six deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In further embodiments, the sense strand has a 30-base pair length, and the antisense strand has a 32-base pair length with a 2 base 3'-overhang. Such agents optionally possess between one and seven deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In other embodiments, the sense strand has a 31-base pair length, and the antisense strand has a 33-base pair length with a 2 base 3'-overhang. Such agents optionally possess between one and eight deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In additional embodiments, the sense strand has a 32-base pair length, and the antisense strand has a 34-base pair length with a 2 base 3'-overhang. Such agents optionally possess between one and nine deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In certain further embodiments, the sense strand has a 33-base pair length, and the antisense strand has a 35-base pair length with a 2 base 3'-overhang. Such agents optionally possess between one and ten deoxyribonucleotides of the 3' terminal region (specifically, the region 3' of the projected Dicer cleavage site) of the sense strand, at least one of which base pairs with a cognate deoxyribonucleotide of the 5' terminal region (specifically, the region 5' of the projected Dicer cleavage site) of the antisense strand. In still other embodiments, any of these DsiRNA agents have an asymmetric structure that further contains 2 deoxyribonucleotides at the 3' end of the sense strand in place of two of the ribonucleotides; optionally, these 2 deoxyribonucleotides base pair with cognate deoxyribonucleotides of the antisense strand.

Certain DsiRNA agent compositions containing two separate oligonucleotides can be linked by a third structure. The third structure will not block Dicer activity on the DsiRNA agent and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the DsiRNA agent in a manner such that a hairpin structure is produced upon annealing of the two oligonucleotides making up the dsNA composition. The hairpin structure will not block Dicer activity on the DsiRNA agent and will not interfere with the directed destruction of the target RNA.

In certain embodiments, the DsiRNA agent of the invention has several properties which enhance its processing by Dicer. According to such embodiments, the DsiRNA agent has a length sufficient such that it is processed by Dicer to produce an siRNA and at least one of the following properties: (i) the DsiRNA agent is asymmetric, e.g., has a 3' overhang on the sense strand and (ii) the DsiRNA agent has a modified 3' end on the antisense strand to direct orientation of Dicer binding and processing of the dsRNA region to an active siRNA. According to these embodiments, the longest strand in the DsiRNA agent comprises 25-43 nucleotides. In one embodiment, the sense strand comprises 25-39 nucleotides and the antisense strand comprises 26-43 nucleotides. The resulting dsNA can have an overhang on the 3' end of the sense strand. The overhang is 1-4 nucleotides, such as 2 nucleotides. The antisense or sense strand may also have a 5' phosphate.

In certain embodiments, the sense strand of a DsiRNA agent is modified for Dicer processing by suitable modifiers located at the 3' end of the sense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsNA to direct the orientation of Dicer processing. In a further embodiment, two terminal DNA bases are located on the 3' end of the sense strand in place of two ribonucleotides forming a blunt end of the duplex on the 5' end of the antisense strand and the 3' end of the sense strand, and a two-nucleotide RNA overhang is located on the 3'-end of the antisense strand. This is an asymmetric composition with DNA on the blunt end and RNA bases on the overhanging end.

In certain other embodiments, the antisense strand of a DsiRNA agent is modified for Dicer processing by suitable modifiers located at the 3' end of the antisense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxyribonucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is also an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsNA has a sequence length of at least 19 nucleotides, wherein these nucleotides are adjacent to the 3' end of antisense strand and are sufficiently complementary to a nucleotide sequence of the target RNA to direct RNA interference.

Additionally, the DsiRNA agent structure can be optimized to ensure that the oligonucleotide segment generated from Dicer's cleavage will be the portion of the oligonucleotide that is most effective in inhibiting gene expression. For example, in one embodiment of the invention, a 27-35-bp oligonucleotide of the DsiRNA agent structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand. As surprisingly identified in the instant invention, such extension can be performed with base paired DNA residues (double stranded DNA:DNA extensions), resulting in extended DsiRNA agents having improved efficacy or duration of effect than corresponding double stranded RNA:RNA-extended DsiRNA agents.

US 2007/0265220 discloses that 27mer DsiRNAs show improved stability in serum over comparable 21mer siRNA compositions, even absent chemical modification. Modifications of DsiRNA agents, such as inclusion of 2'-O-methyl RNA in the antisense strand, in patterns such as detailed in US 2007/0265220 and in the instant Examples, when coupled with addition of a 5' Phosphate, can improve stability of DsiRNA agents. Addition of 5'-phosphate to all strands in synthetic RNA duplexes may be an inexpensive and physiological method to confer some limited degree of nuclease stability.

The chemical modification patterns of the DsiRNA agents of the instant invention are designed to enhance the efficacy of such agents. Accordingly, such modifications are designed to avoid reducing potency of DsiRNA agents; to avoid interfering with Dicer processing of DsiRNA agents; to improve stability in biological fluids (reduce nuclease sensitivity) of DsiRNA agents; or to block or evade detection by the innate immune system. Such modifications are also designed to avoid being toxic and to avoid increasing the cost or impact the ease of manufacturing the instant DsiRNA agents of the invention.

RNA Processing
siRNA

The process of siRNA-mediated RNAi is triggered by the presence of long, dsRNA molecules in a cell. During the initiation step of RNAi, these dsRNA molecules are cleaved into 21-23 nucleotide (nt) small-interfering RNA duplexes (siRNAs) by Dicer, a conserved family of enzymes containing two RNase III-like domains (Bernstein et al. 2001; Elbashir et al. 2001). The siRNAs are characterized by a 19-21 base pair duplex region and 2 nucleotide 3' overhangs on each strand. During the effector step of RNAi, the siRNAs become incorporated into a multimeric protein complex called RNA-induced silencing complex (RISC), where they serve as guides to select fully complementary mRNA substrates for degradation. Degradation is initiated by endonucleolytic cleavage of the mRNA within the region complementary to the siRNA. More precisely, the mRNA is cleaved at a position 10 nucleotides from the 5' end of the guiding siRNA (Elbashir et al. 2001 *Genes & Dev.* 15: 188-200; Nykanen et al. 2001 *Cell* 107: 309-321; Martinez et al. 2002 *Cell* 110: 563-574). An endonuclease responsible for this cleavage was identified as Argonaute2 (Ago2; Liu et al. *Science*, 305: 1437-41).

miRNA

The majority of human miRNAs (70%)—and presumably the majority of miRNAs of other mammals—are transcribed from introns and/or exons, and approximately 30% are located in intergenic regions (Rodriguez et al., *Genome Res.* 2004, 14(10A), 1902-1910). In human and animal, miRNAs are usually transcribed by RNA polymerase II (Farh et al. *Science* 2005, 310(5755), 1817-1821), and in some cases by pol III (Borchert et al. *Nat. Struct. Mol. Biol.* 2006, 13(12), 1097-1101). Certain viral encoded miRNAs are transcribed by RNA polymerase III (Pfeffer et al. *Nat. Methods* 2005, 2(4), 269-276; Andersson et al. *J. Virol.* 2005, 79(15), 9556-9565), and some are located in the open reading frame of viral gene (Pfeffer et al. *Nat. Methods* 2005, 2(4), 269-276; Samols et al. *J. Virol.* 2005, 79(14), 9301-9305). miRNA transcription results in the production of large monocistronic, bicistronic or polycistronic primary transcripts (pri-miRNAs). A single pri-miRNA may range from approximately 200 nucleotides (nt) to several kilobases (kb) in length and have both a 5' 7-methylguanosine (m7) caps and a 3' poly (A) tail. Characteristically, the mature miRNA sequences are localized to regions of imperfect stem-loop sequences within the pri-miRNAs (Cullen, *Mol. Cell.* 2004, 16(6), 861-865).

The first step of miRNA maturation in the nucleus is the recognition and cleavage of the pri-miRNAs by the RNase III Drosha-DGCR8 nuclear microprocessor complex, which releases a ~70 nt hairpin-containing precursor molecule called pre-miRNAs, with a monophosphate at the 5' terminus and a 2-nt overhang with a hydroxyl group at the 3' terminus (Cai et al. *RNA* 2004, 10(12), 1957-1966; Lee et al. *Nature* 2003, 425(6956), 415-419; Kim *Nat. Rev. Mol. Cell. Biol.* 2005, 6(5), 376-385). The next step is the nuclear transport of the pre-miRNAs out of the nucleus into the cytoplasm by Exportin-5, a carrier protein (Yi et al. *Genes. Dev.* 2003, 17(24), 3011-3016, Bohnsack et al. *RNA* 2004, 10(2), 185-191). Exportin-5 and the GTP-bound form of its cofactor Ran together recognize and bind the 2 nucleotide 3' overhang and the adjacent stem that are characteristics of pre-miRNA (Basyuk et al. *Nucl. Acids Res.* 2003, 31(22), 6593-6597, Zamore *Mol. Cell.* 2001, 8(6), 1158-1160). In the cytoplasm, GTP hydrolysis results in release of the pre-miRNA, which is then processed by a cellular endonuclease III enzyme Dicer (Bohnsack et al.). Dicer was first recognized for its role in generating siRNAs that mediate RNA interference (RNAi). Dicer acts in concert with its cofactors TRBP (Transactivating region binding protein; Chendrimata et al. *Nature* 2005, 436(7051), 740-744) and PACT (interferon-inducible double strand-RNA-dependant protein kinase activator; Lee et al. *EMBO J.* 2006, 25(3), 522-532). These enzymes bind at the 3' 2 nucleotide overhang at the base of the pre-miRNA hairpin and remove the terminal loop, yielding an approximately 21-nt miRNA duplex intermediate with both termini having 5' monophosphates, 3' 2 nucleotide overhangs and 3' hydroxyl groups. The miRNA guide strand, the 5' terminus of which is energetically less stable, is then selected for incorporation into the RISC(RNA-induced silencing complex), while the 'passenger' strand is released and degraded (Maniataki et al. *Genes. Dev.* 2005, 19(24), 2979-2990; Hammond et al. *Nature* 2000, 404(6775), 293-296). The composition of RISC remains incompletely defined, but a key component is a member of the Argonaute (Ago) protein family (Maniataki et al.; Meister et al. *Mol. Cell.* 2004, 15(2), 185-197).

The mature miRNA then directs RISC to complementary mRNA species. If the target mRNA has perfect complementarity to the miRNA-armed RISC, the mRNA will be cleaved and degraded (Zeng et al. *Proc. Natl. Acad. Sci. USA* 2003, 100(17), 9779-9784; Hutvagner et al. *Science* 2002, 297(55 89), 2056-2060). But as the most common situation in mammalian cells, the miRNAs targets mRNAs with imperfect complementarity and suppress their translation, resulting in reduced expression of the corresponding proteins (Yekta et al. *Science* 2004, 304(5670), 594-596; Olsen et al. *Dev. Biol.* 1999, 216(2), 671-680). The 5' region of the miRNA, especially the match between miRNA and target sequence at nucleotides 2-7 or 8 of miRNA (starting from position 1 at the 5' terminus), which is called the seed region, is essentially important for miRNA targeting, and this seed match has also become a key principle widely used in computer prediction of the miRNA targeting (Lewis et al. *Cell* 2005, 120(1), 15-20; Brennecke et al. *PLoS Biol.* 2005, 3(3), e85). miRNA regulation of the miRNA-mRNA duplexes is mediated mainly through multiple complementary sites in the 3' UTRs, but there are many exceptions. miRNAs may also bind the 5' UTR and/or the coding region of mRNAs, resulting in a similar outcome (Lytle et al. *Proc. Natl. Acad. Sci. USA* 2007, 104 (23), 9667-9672).

RNase H

RNase H is a ribonuclease that cleaves the 3'-OP bond of RNA in a DNA/RNA duplex to produce 3'-hydroxyl and 5'-phosphate terminated products. RNase H is a non-specific endonuclease and catalyzes cleavage of RNA via a hydrolytic mechanism, aided by an enzyme-bound divalent metal ion. Members of the RNase H family are found in nearly all organisms, from archaea and prokaryotes to eukaryotes. During DNA replication, RNase H is believed to cut the RNA primers responsible for priming generation of Okazaki fragments; however, the RNase H enzyme may be more generally employed to cleave any DNA:RNA hybrid sequence of sufficient length (e.g., typically DNA:RNA hybrid sequences of 4 or more base pairs in length in mammals).

MicroRNA and MicroRNA-Like Therapeutics

MicroRNAs (miRNAs) have been described to act by binding to the 3' UTR of a template transcript, thereby inhibiting expression of a protein encoded by the template transcript by a mechanism related to but distinct from classic RNA interference. Specifically, miRNAs are believed to act by reducing translation of the target transcript, rather than by decreasing its stability. Naturally-occurring miRNAs are typically approximately 22 nt in length. It is believed that they are derived from larger precursors known as small temporal RNAs (stRNAs) approximately 70 nt long.

Interference agents such as siRNAs, and more specifically such as miRNAs, that bind within the 3' UTR (or elsewhere in a target transcript, e.g., in repeated elements of, e.g., Notch and/or transcripts of the Notch family) and inhibit translation may tolerate a larger number of mismatches in the siRNA/template (miRNA/template) duplex, and particularly may tolerate mismatches within the central region of the duplex. In fact, there is evidence that some mismatches may be desirable or required, as naturally occurring stRNAs frequently exhibit such mismatches, as do miRNAs that have been shown to inhibit translation in vitro (Zeng et al., *Molecular Cell,* 9: 1-20). For example, when hybridized with the target transcript, such miRNAs frequently include two stretches of perfect complementarity separated by a region of mismatch. Such a hybridized complex commonly includes two regions of perfect complementarily (duplex portions) comprising nucleotide pairs, and at least a single mismatched base pair, which may be, e.g., G:A, G:U, G:G, A:A, A:C, U:U, U:C, C:C, G:-, A:-, U:-, C:-, etc. Such mismatched nucleotides, especially if present in tandem (e.g., a two, three or four nucleotide area of mismatch) can form a bulge that separates duplex portions which are located on either flank of such a bulge. A variety of structures are possible. For example, the miRNA may include multiple areas of nonidentity (mismatch). The areas of nonidentity (mismatch) need not be symmetrical in the sense that both the target and the miRNA include nonpaired nucleotides. For example, structures have been described in which only one strand includes nonpaired nucleotides (Zeng et al.). Typically the stretches of perfect complementarily within a miRNA agent are at least 5 nucleotides in length, e.g., 6, 7, or more nucleotides in length, while the regions of mismatch may be, for example, 1, 2, 3, or 4 nucleotides in length.

In general, any particular siRNA could function to inhibit gene expression both via (i) the "classical" siRNA pathway, in which stability of a target transcript is reduced and in which perfect complementarily between the siRNA and the target is frequently preferred, and also by (ii) the "alternative" pathway (generally characterized as the miRNA pathway in animals), in which translation of a target transcript is inhibited. Generally, the transcripts targeted by a particular siRNA via mechanism (i) would be distinct from the transcript targeted via mechanism (ii), although it is possible that a single transcript could contain regions that could serve as targets for both the classical and alternative pathways. (Note that the terms "classical" and "alternative" are used merely for convenience and generally are believed to reflect historical timing of discovery of such mechanisms in animal cells, but do not reflect the importance, effectiveness, or other features of either mechanism.) One common goal of siRNA design has been to target a single transcript with great specificity, via mechanism (i), while minimizing off-target effects, including those effects potentially elicited via mechanism (ii). However, it is among the goals of the instant invention to provide RNA interference agents that possess mismatch residues by design, either for purpose of mimicking the activities of naturally-occurring miRNAs, or to create agents directed against target RNAs for which no corresponding miRNA is presently known, with the inhibitory and/or therapeutic efficacies/potencies of such mismatch-containing DsiRNA agents (e.g., DsiRNAmm agents) tolerant of, and indeed possibly enhanced by, such mismatches.

The tolerance of miRNA agents for mismatched nucleotides (and, indeed the existence and natural use of mechanism (ii) above in the cell) suggests the use of miRNAs in manners that are advantageous to and/or expand upon the "classical" use of perfectly complementary siRNAs that act via mechanism (i). Because miRNAs are naturally occurring molecules, there are likely to be distinct advantages in applying miRNAs as therapeutic agents. miRNAs benefit from hundreds of millions of years of evolutionary "fine tuning" of their function. Thus, sequence-specific "off target" effects should not be an issue with naturally occurring miRNAs, nor, by extension, with certain synthetic DsiRNAs of the invention (e.g., DsiRNAmm agents) designed to mimic naturally occurring miRNAs. In addition, miRNAs have evolved to modulate the expression of groups of genes, driving both up and down regulation (in certain instances, performing both functions concurrently within a cell with a single miRNA acting promiscuously upon multiple target RNAs), with the result that complex cell functions can be precisely modulated. Such replacement of naturally occurring miRNAs can involve introducing synthetic miRNAs or miRNA mimetics (e.g., certain DsiRNAmms) into diseased tissues in an effort to restore normal proliferation, apoptosis, cell cycle, and other cellular functions that have been affected by down-regulation of one or more miRNAs. In certain instances, reactivation of these miRNA-regulated pathways has produced a significant therapeutic response (e.g., In one study on cardiac hypertrophy, overexpression of miR-133 by adenovirus-mediated delivery of a miRNA expression cassette protected animals from agonist-induced cardiac hypertrophy, whereas reciprocally reduction of miR-133 in wild-type mice by antagomirs caused an increase in hypertrophic markers (Care et al. *Nat. Med.* 13: 613-618)).

To date, more than 600 miRNAs have been identified as encoded within the human genome, with such miRNAs expressed and processed by a combination of proteins in the nucleus and cytoplasm. miRNAs are highly conserved among vertebrates and comprise approximately 2% of all mammalian genes. Since each miRNA appears to regulate the expression of multiple, e.g., two, three, four, five, six, seven, eight, nine or even tens to hundreds of different genes, miRNAs can function as "master-switches", efficiently regulating and coordinating multiple cellular pathways and processes. By coordinating the expression of multiple genes, miRNAs play key roles in embryonic development, immunity, inflammation, as well as cellular growth and proliferation.

Expression and functional studies suggest that the altered expression of specific miRNAs is critical to a variety of human diseases. Mounting evidence indicates that the introduction of specific miRNAs into disease cells and tissues can induce favorable therapeutic responses (Pappas et al., *Expert Opin Ther Targets.* 12: 115-27). The promise of miRNA therapy is perhaps greatest in cancer due to the apparent role of certain miRNAs as tumor suppressors. The rationale for miRNA-based therapeutics for, e.g., cancer is supported, at least in part, by the following observations:

(1) miRNAs are frequently mis-regulated and expressed at altered levels in diseased tissues when compared to normal tissues. A number of studies have shown altered levels of miRNAs in cancerous tissues relative to their corresponding normal tissues. Often, altered expression is the consequence of genetic mutations that lead to increased or reduced expression of particular miRNAs. Diseases that possess unique miRNA expression signatures can be exploited as diagnostic and prognostic markers, and can be targeted with the DsiRNA (e.g., DsiRNAmm) agents of the invention.

(2) Mis-regulated miRNAs contribute to cancer development by functioning as oncogenes or tumor suppressors. Oncogenes are defined as genes whose over-expression or inappropriate activation leads to oncogenesis. Tumor suppressors are genes that are required to keep cells from being cancerous; the down-regulation or inactivation of tumor suppressors is a common inducer of cancer. Both types of genes represent preferred drug targets, as such targeting can specifically act upon the molecular basis for a particular cancer. Examples of oncogenic miRNAs are miR-155 and miR-17-92; let-7 is an example of a tumor suppressive miRNA.

(3) Administration of miRNA induces a therapeutic response by blocking or reducing tumor growth in pre-clinical animal studies. The scientific literature provides proof-of-concept studies demonstrating that restoring miRNA function can prevent or reduce the growth of cancer cells in vitro and also in animal models. A well-characterized example is the anti-tumor activity of let-7 in models for breast and lung cancer. DsiRNAs (e.g., DsiRNAmms) of the invention which are designed to mimic let-7 can be used to target such cancers, and it is also possible to use the DsiRNA design parameters described herein to generate new DsiRNA (e.g., DsiR-NAmm) agents directed against target RNAs for which no counterpart naturally occurring miRNA is known (e.g., repeats within Notch or other transcripts), to screen for therapeutic lead compounds, e.g., agents that are capable of reducing tumor burden in pre-clinical animal models.

(4) A given miRNA controls multiple cellular pathways and therefore may have superior therapeutic activity. Based on their biology, miRNAs can function as "master switches" of the genome, regulating multiple gene products and coordinating multiple pathways. Genes regulated by miRNAs include genes that encode conventional oncogenes and tumor suppressors, many of which are individually pursued as drug targets by the pharmaceutical industry. Thus, miRNA therapeutics could possess activity superior to siRNAs and other forms of lead compounds by targeting multiple disease and/or cancer-associated genes. Given the observation that mis-regulation of miRNAs is frequently an early event in the process of tumorigenesis, miRNA therapeutics, which replace missing miRNAs, may be the most appropriate therapy.

(5) miRNAs are natural molecules and are therefore less prone to induce non-specific side-effects. Millions of years of evolution helped to develop the regulatory network of miRNAs, fine-tuning the interaction of miRNA with target messenger RNAs. Therefore, miRNAs and miRNA derivatives (e.g., DsiRNAs designed to mimic naturally occurring miRNAs) will have few if any sequence-specific "off-target" effects when applied in the proper context.

The physical characteristics of siRNAs and miRNAs are similar. Accordingly, technologies that are effective in delivering siRNAs (e.g., DsiRNAs of the invention) are likewise effective in delivering synthetic miRNAs (e.g., certain DsiR-NAmms of the invention).

Conjugation and Delivery of DsiRNA Agents

In certain embodiments, the present invention relates to a method for treating a subject having or at risk of developing a disease or disorder. In such embodiments, the DsiRNA can act as a novel therapeutic agent for controlling the disease or disorder. The method comprises administering a pharmaceutical composition of the invention to the patient (e.g., human), such that the expression, level and/or activity a target RNA is reduced. The expression, level and/or activity of a polypeptide encoded by the target RNA might also be reduced by a DsiRNA of the instant invention.

In the treatment of a disease or disorder, the DsiRNA can be brought into contact with the cells or tissue exhibiting or associated with a disease or disorder. For example, DsiRNA substantially identical to all or part of a target RNA sequence, may be brought into contact with or introduced into a diseased, disease-associated or infected cell, either in vivo or in vitro. Similarly, DsiRNA substantially identical to all or part of a target RNA sequence may administered directly to a subject having or at risk of developing a disease or disorder.

Therapeutic use of the DsiRNA agents of the instant invention can involve use of formulations of DsiRNA agents comprising multiple different DsiRNA agent sequences. For example, two or more, three or more, four or more, five or more, etc. of the presently described agents can be combined to produce a formulation that, e.g., targets multiple different regions of one or more target RNA(s). A DsiRNA agent of the instant invention may also be constructed such that either strand of the DsiRNA agent independently targets two or more regions of a target RNA. Use of multifunctional DsiRNA molecules that target more then one region of a target nucleic acid molecule is expected to provide potent inhibition of RNA levels and expression. For example, a single multifunctional DsiRNA construct of the invention can target both conserved and variable regions of a target nucleic acid molecule, thereby allowing down regulation or inhibition of, e.g., different strain variants of a virus, or splice variants encoded by a single target gene.

A DsiRNA agent of the invention can be conjugated (e.g., at its 5' or 3' terminus of its sense or antisense strand) or unconjugated to another moiety (e.g. a non-nucleic acid moiety such as a peptide), an organic compound (e.g., a dye, cholesterol, or the like). Modifying DsiRNA agents in this way may improve cellular uptake or enhance cellular targeting activities of the resulting DsiRNA agent derivative as compared to the corresponding unconjugated DsiRNA agent, are useful for tracing the DsiRNA agent derivative in the cell, or improve the stability of the DsiRNA agent derivative compared to the corresponding unconjugated DsiRNA agent.

RNAi In Vitro Assay to Assess DsiRNA Activity

An in vitro assay that recapitulates RNAi in a cell-free system can optionally be used to evaluate DsiRNA constructs. For example, such an assay comprises a system described by Tuschl et al., 1999, *Genes and Development*, 13, 3191-3197 and Zamore et al., 2000, *Cell*, 101, 25-33, adapted for use with DsiRNA agents directed against target RNA, and commercially available kits, including Turbo Dicer (Genlantis). A *Drosophila* extract derived from syncytial blastoderm is used to reconstitute RNAi activity in vitro. Target RNA is generated via in vitro transcription from an appropriate plasmid using T7 RNA polymerase or via chemical synthesis. Sense and antisense DsiRNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing DsiRNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which DsiRNA is omitted from the reaction.

Alternately, internally-labeled target RNA for the assay is prepared by in vitro transcription in the presence of [alpha-32P] CTP, passed over a G50 Sephadex column by spin chromatography and used as target RNA without further purification. Optionally, target RNA is 5'-32P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without DsiRNA and the cleavage products generated by the assay.

Methods of Introducing Nucleic Acids, Vectors, and Host Cells

DsiRNA agents of the invention may be directly introduced into a cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The DsiRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or other-wise increase inhibition of the target RNA.

A cell having a target RNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target RNA sequence and the dose of DsiRNA agent material delivered, this process may provide partial or complete loss of function for the target RNA. A reduction or loss of RNA levels or expression (either RNA expression or encoded polypeptide expression) in at least 50%, 60%, 70%, 80%, 90%, 95% or 99% or more of targeted cells is exemplary Inhibition of target RNA levels or expression refers to the absence (or observable decrease) in the level of RNA or RNA-encoded protein. Specificity refers to the ability to inhibit the target RNA without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). Inhibition of target RNA sequence(s) by the DsiRNA agents of the invention also can be measured based upon the effect of administration of such DsiRNA agents upon measurable phenotypes such as tumor size for cancer treatment, viral load/titer for viral infectious diseases, etc. either in vivo or in vitro. For viral infectious diseases, reductions in viral load or titer can include reductions of, e.g., 50%, 60%, 70%, 80%, 90%, 95% or 99% or more, and are often measured in logarithmic terms, e.g., 10-fold, 100-fold, 1000-fold, $10^5$-fold, $10^6$-fold, $10^7$-fold reduction in viral load or titer can be achieved via administration of the DsiRNA agents of the invention to cells, a tissue, or a subject.

For RNA-mediated inhibition in a cell line or whole organism, expression a reporter or drug resistance gene whose protein product is easily assayed can be measured. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention.

Lower doses of injected material and longer times after administration of RNA silencing agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target RNA or translation of target protein. As an example, the efficiency of inhibition may be determined by assessing the amount of gene product in the cell; RNA may be detected with a hybridization probe having a nucleotide sequence outside the region used for the inhibitory DsiRNA, or translated polypeptide may be detected with an antibody raised against the polypeptide sequence of that region.

The DsiRNA agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

RNA Interference Based Therapy

As is known, RNAi methods are applicable to a wide variety of genes in a wide variety of organisms and the disclosed compositions and methods can be utilized in each of these contexts. Examples of genes which can be targeted by the disclosed compositions and methods include endogenous genes which are genes that are native to the cell or to genes that are not normally native to the cell. Without limitation, these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

More specifically, a target mRNA of the invention can specify the amino acid sequence of a cellular protein (e.g., a nuclear, cytoplasmic, transmembrane, or membrane-associated protein). In another embodiment, the target mRNA of the invention can specify the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In one aspect, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Pathogens include RNA viruses such as flaviviruses, picornaviruses, rhabdoviruses, filoviruses, retroviruses, including lentiviruses, or DNA viruses such as adenoviruses, poxviruses, herpes viruses, cytomegaloviruses, hepadnaviruses or others. Additional pathogens include bacteria, fungi, helminths, schistosomes and trypanosomes. Other kinds of pathogens can include mammalian transposable elements. Alternatively, the protein may be a tumor-associated protein or an autoimmune disease-associated protein.

The target gene may be derived from or contained in any organism. The organism may be a plant, animal, protozoa, bacterium, virus or fungus. See e.g., U.S. Pat. No. 6,506,559, incorporated herein by reference.

Pharmaceutical Compositions

In certain embodiments, the present invention provides for a pharmaceutical composition comprising the DsiRNA agent of the present invention. The DsiRNA agent sample can be suitably formulated and introduced into the environment of the cell by any means that allows for a sufficient portion of the sample to enter the cell to induce gene silencing, if it is to occur. Many formulations for dsNA are known in the art and can be used so long as the dsNA gains entry to the target cells so that it can act. See, e.g., U.S. published patent application Nos. 2004/0203145 A1 and 2005/0054598 A1. For example, the DsiRNA agent of the instant invention can be formulated in buffer solutions such as phosphate buffered saline solutions, liposomes, micellar structures, and capsids. Formulations of DsiRNA agent with cationic lipids can be used to facilitate transfection of the DsiRNA agent into cells. For example, cationic lipids, such as lipofectin (U.S. Pat. No. 5,705,188), cationic glycerol derivatives, and polycationic molecules, such as polylysine (published PCT International Application WO 97/30731), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, if a plasmid encoding a DsiRNA agent is selected, single dose amounts in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

It can be appreciated that the method of introducing DsiRNA agents into the environment of the cell will depend on the type of cell and the make up of its environment. For example, when the cells are found within a liquid, one preferable formulation is with a lipid formulation such as in lipofectamine and the DsiRNA agents can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate DsiRNA agents in a buffer or saline solution and directly inject the formulated DsiRNA agents into cells, as in studies with oocytes. The direct injection of DsiRNA agents duplexes may also be done. For suitable methods of introducing dsNA (e.g., DsiRNA agents), see U.S. published patent application No. 2004/0203145 A1.

Suitable amounts of a DsiRNA agent must be introduced and these amounts can be empirically determined using standard methods. Typically, effective concentrations of individual DsiRNA agent species in the environment of a cell will be about 50 nanomolar or less, 10 nanomolar or less, or compositions in which concentrations of about 1 nanomolar or less can be used. In another embodiment, methods utilizing a concentration of about 200 picomolar or less, and even a concentration of about 50 picomolar or less, about 20 picomolar or less, about 10 picomolar or less, or about 5 picomolar or less can be used in many circumstances.

The method can be carried out by addition of the DsiRNA agent compositions to any extracellular matrix in which cells can live provided that the DsiRNA agent composition is formulated so that a sufficient amount of the DsiRNA agent can enter the cell to exert its effect. For example, the method is amenable for use with cells present in a liquid such as a liquid culture or cell growth media, in tissue explants, or in whole organisms, including animals, such as mammals and especially humans.

The level or activity of a target RNA can be determined by any suitable method now known in the art or that is later developed. It can be appreciated that the method used to measure a target RNA and/or the expression of a target RNA can depend upon the nature of the target RNA. For example, if the target RNA encodes a protein, the term "expression" can refer to a protein or the RNA/transcript derived from the target RNA. In such instances, the expression of a target RNA can be determined by measuring the amount of RNA corresponding to the target RNA or by measuring the amount of that protein. Protein can be measured in protein assays such as by staining or immunoblotting or, if the protein catalyzes a reaction that can be measured, by measuring reaction rates. All such methods are known in the art and can be used. Where target RNA levels are to be measured, any art-recognized methods for detecting RNA levels can be used (e.g., RT-PCR, Northern Blotting, etc.). In targeting viral RNAs with the DsiRNA agents of the instant invention, it is also anticipated that measurement of the efficacy of a DsiRNA agent in reducing levels of a target virus in a subject, tissue, in cells, either in vitro or in vivo, or in cell extracts can also be used to determine the extent of reduction of target viral RNA level(s). Any of the above measurements can be made on cells, cell extracts, tissues, tissue extracts or any other suitable source material.

The determination of whether the expression of a target RNA has been reduced can be by any suitable method that can reliably detect changes in RNA levels. Typically, the determination is made by introducing into the environment of a cell undigested DsiRNA such that at least a portion of that DsiRNA agent enters the cytoplasm, and then measuring the level of the target RNA. The same measurement is made on identical untreated cells and the results obtained from each measurement are compared.

The DsiRNA agent can be formulated as a pharmaceutical composition which comprises a pharmacologically effective amount of a DsiRNA agent and pharmaceutically acceptable carrier. A pharmacologically or therapeutically effective amount refers to that amount of a DsiRNA agent effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of dsNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the dsNA can be administered once daily. However, the therapeutic agent may also be dosed in dosage units containing two, three, four, five, six or more sub-doses administered at appropriate intervals throughout the day. In that case, the dsNA contained in each sub-dose must be correspondingly smaller in order to achieve the total daily dosage unit. The dosage unit can also be compounded for a single dose over several days, e.g., using a conventional sustained release formulation which provides sustained and consistent release of the dsNA over a several day period. Sustained release formulations are well known in the art. In this embodiment, the dosage unit contains a corresponding multiple of the daily dose. Regardless of the formulation, the pharmaceutical composition must contain dsNA in a quantity sufficient to inhibit expression of the target gene in the animal or human being treated. The composition can be compounded in such a way that the sum of the multiple units of dsNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsNA in plasma may be measured by standard methods, for example, by high performance liquid chromatography.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a disease or disorder caused, in whole or in part, by the expression of a target RNA and/or the presence of such target RNA (e.g., in the context of a viral infection, the presence of a target RNA of the viral genome, capsid, host cell component, etc.).

"Treatment", or "treating" as used herein, is defined as the application or administration of a therapeutic agent (e.g., a DsiRNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., a DsiRNA agent or vector or transgene encoding same). Subjects at risk for the disease can be identified by, for example, any or a combination of diagnostic or prognostic assays as described herein. Administration of a prophylactic agent can occur prior to the detection of, e.g., viral particles in a subject, or the manifestation of symptoms characteristic of the disease or disorder, such that the disease or disorder is prevented or, alternatively, delayed in its progression.

Another aspect of the invention pertains to methods of treating subjects therapeutically, i.e., alter onset of symptoms of the disease or disorder. These methods can be performed in vitro (e.g., by culturing the cell with the DsiRNA agent) or, alternatively, in vivo (e.g., by administering the DsiRNA agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target RNA molecules of the present invention or target RNA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, a DsiRNA agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner Standard techniques well known in the art or the techniques specifically described below were utilized.

Example 1

Methods

Oligonucleotide Synthesis, In Vitro Use

Individual RNA strands were synthesized and HPLC purified according to standard methods (Integrated DNA Technologies, Coralville, Iowa). All oligonucleotides were quality control released on the basis of chemical purity by HPLC analysis and full length strand purity by mass spectrometry analysis. Duplex RNA DsiRNAs were prepared before use by mixing equal quantities of each strand, briefly heating to 100° C. in RNA buffer (IDT) and then allowing the mixtures to cool to room temperature.

Oligonucleotide Synthesis, In Vivo Use

Individual RNA strands were synthesized and HPLC purified according to standard methods (OligoFactory, Holliston, Mass.). All oligonucleotides were quality control released on the basis of chemical purity by HPLC analysis and full length strand purity by mass spectrometry analysis. Duplex RNA DsiRNAs were prepared before use by mixing equimolar quantities of each strand, briefly heating to 100° C. in RNA buffer (IDT) and then allowing the mixtures to cool to room temperature.

Cell Culture and RNA Transfection

HeLa cells were obtained from ATCC and maintained in Dulbecco's modified Eagle medium (HyClone) supplemented with 10% fetal bovine serum (HyClone) at 37° C. under 5% $CO_2$. For RNA transfections of FIGS. 7, 9, 12, and 13, HeLa cells were transfected with DsiRNAs as indicated at a final concentration of 0.1 nM using Lipofectamine™ RNAiMAX (Invitrogen) and following manufacturer's instructions. Briefly, 2.5 μL of a 0.02 μM stock solution of each DsiRNA were mix with 46.5 μL, of Opti-MEM I (Invitrogen) and 1 μL of Lipofectamine™ RNAiMAX. The resulting 50 μL mix was added into individual wells of 12 well plates and incubated for 20 min at RT to allow DsiRNA:Lipofectamine™ RNAiMAX complexes to form. Meanwhile, HeLa cells were trypsinized and resuspended in medium at a final concentration of 367 cells/μL. Finally, 450 μL of the cell suspension were added to each well (final volume 500 μL) and plates were placed into the incubator for 24 hours.

RNA Isolation and Analysis, In Vitro

Cells were washed once with 2 mL of PBS, and total RNA was extracted using RNeasy Mini Kit™ (Qiagen) and eluted in a final volume of 30 μL. 1 μg of total RNA was reverse-transcribed using Transcriptor $1^{st}$ Strand cDNA Kit™ (Roche) and random hexamers following manufacturer's instructions. One-thirtieth (0.66 μL) of the resulting cDNA was mixed with 5 μL of iQ™ Multiplex Powermix (Bio-Rad) together with 3.33 μL of $H_2O$ and 1 μL of a 3 μM mix containing 2 sets of primers and probes specific for human genes HPRT-1 (accession number NM_000194) and SFRS9 (accession number NM_003769) genes:

```
Hu HPRT forward primer
F517 GACTTTGCTTTCCTTGGTCAG (SEQ ID NO: 1)

Hu HPRT reverse primer
R591 GGCTTATATCCAACACTTCGTGGG (SEQ ID NO: 2)

Hu HPRT probe
P554 Cy5-ATGGTCAAGGTCGCAAGCTTGCTGGT-IBFQ (SEQ ID
NO: 3)

Hu SFRS9 forward primer
F569 TGTGCAGAAGGATGGAGT (SEQ ID NO: 4)

Hu SFRS9 reverse primer
R712 CTGGTGCTTCTCTCAGGATA (SEQ ID NO: 5)

Hu SFRS9 probe
P644 HEX-TGGAATATGCCCTGCGTAAACTGGA-IBFQ (SEQ ID
NO: 6)
```

In vivo Sample Preparation and Injection

DsiRNA was formulated in Invivofectamine™ according to manufacturer's protocol (Invitrogen, Carlsbad, Calif.). Briefly, the N/group of mice and body weight of the mice used were determined, then amount of DsiRNA needed for each group of mice treated was calculated. One ml IVF-oligo was enough for 4 mice of 25 g/mouse at 10 mg/kg dosage. One mg DsiRNA was added to one ml Invivofectamine™, and mixed at RT for 30 min on a rotator. 14 ml of 5% glucose was used to dilute formulated IVF-DsiRNA and was applied to 50 kDa molecular weight cutoff spin concentrators (Amicon). The spin concentrators were spun at 4000 rpm for ~2 hours at 4 C until the volume of IVF-DsiRNA was brought down to less than 1 ml. Recovered IVF-DsiRNA was diluted to one ml with 5% glucose and readied for animal injection.

Animal Injection and Tissue Harvesting

Animals were subjected to surgical anesthesia by i.p. injection with Ketamine/Xylazine. Each mouse was weighed before injection. Formulated IVF-DsiRNA was injected i.v. at 100 ul/10 g of body weight. After 24 hours, mice were sacrificed by $CO_2$ inhalation. Tissues for analysis were collected and placed in tubes containing 2 ml RNAlater™ (Qiagen) and rotated at RT for 30 min before incubation at 4° C. overnight. The tissues were stored subsequently at −80° C. until use.

Tissue RNA Preparation and Quantitation

About 50-100 mg of tissue pieces were homogenized in 1 ml QIAzol™ (Qiagen) on Tissue Lyser™ (Qiagen). Then total RNA were isolated according to the manufacturer's protocol. Briefly, 0.2 ml Chloroform (Sigma-Aldrich) was added to the QIAzol™ lysates and mixed vigorously by vortexing. After spinning at 14,000 rpm for 15 min at 4° C., aqueous phase was collected and mixed with 0.5 ml of isopropanol. After another centrifugation at 14,000 rpm for 10 min, the RNA pellet was washed once with 75% ethanol and briefly dried. The isolated RNA was resuspended in 100 µl RNase-Free water, and subjected to clean up with RNeasy™ total RNA preparation kit (Qiagen) or SV 96 total RNA Isolation System (Promega) according to manufacturer's protocol.

First Strand cDNA Synthesis, In Vivo

1 µg of total RNA was reverse-transcribed using Transcriptor 1$^{st}$ Strand cDNA Kit™ (Roche) and oligo-dT following manufacturer's instructions. One-fortieth (0.66 µL) of the resulting cDNA was mixed with 5 µL of IQ Multiplex Powermix (Bio-Rad) together with 3.33 µL of $H_2O$ and 1 µL of a 3 µM mix containing 2 sets of primers and probes specific for mouse genes HPRT-1 (accession number NM_013556) and KRAS (accession number NM_021284) genes:

```
Mm HPRT forward primer
F576 CAAACTTTGCTTTCCCTGGT (SEQ ID NO: 7)

Mm HPRT reverse primer
R664 CAACAAAGTCTGGCCTGTATC (SEQ ID NO: 8)

Mm HPRT probe
P616 Cy5- TGGTTAAGGTTGCAAGCTTGCTGGTG-IBFQ (SEQ ID
NO: 9)

Mm KRAS forward primer
F275 CTTTGTGGATGAGTACGACC (SEQ ID NO: 10)

Mm KRAS reverse primer
R390 CACTGTACTCCTCTTGACCT (SEQ ID NO: 11)

Mm KRAS probe
P297 FAM-ACGATAGAGGACTCCTACAGGAAACAAGT-IBFQ (SEQ
ID NO: 12)
```

Quantitative RT-PCR

A CFX96 Real-time System with a C1000 Thermal cycler (Bio-Rad) was used for the amplification reactions. PCR conditions were: 95° C. for 3 min; and then cycling at 95° C., 10 sec; 55° C., 1 min for 40 cycles. Each sample was tested in triplicate. For HPRT Examples, relative HPRT mRNA levels were normalized to SFRS9 mRNA levels and compared with mRNA levels obtained in control samples treated with the transfection reagent plus a control mismatch duplex, or untreated. For KRAS examples, relative KRAS mRNA levels were normalized to HPRT-1 mRNA levels and compared with mRNA levels obtained in control samples from mice treated with 5% glucose. Data were analyzed using Bio-Rad CFX Manager version 1.0 (in vitro Examples) or 1.5 (in vivo Example) software.

Example 2

Efficacy of DsiRNA Agents Possessing Single Stranded Extensions

DsiRNA agents possessing single stranded extensions were examined for efficacy of sequence-specific target mRNA inhibition. Specifically, KRAS-249M and HPRT-targeting DsiRNA duplexes possessing 5' single stranded guide extensions were transfected into HeLa cells at a fixed concentration of 20 nM and HPRT expression levels were measured 24 hours later (FIGS. 7 and 9). Transfections were performed in duplicate, and each duplicate was assayed in triplicate for KRAS-249M and HPRT expression, respectively, by qPCR.

Under these conditions (0.1 nM duplexes, Lipofectamine™ RNAiMAX transfection), KRAS-249 gene expression was reduced by about 60-85% by duplexes DNA10PS, RNA10PS, RNA10PS-2'-OME, DNA15PS, RNA15PS, and RNA15PS-2'OME (FIG. 7). By comparison, a duplex without the single stranded guide extensions reduced KRAS-249 gene expression by about 90%. Thus, the duplexes having single stranded guide extensions were as effective in silencing KRAS-249 as a duplex without the single stranded guide extensions. All single stranded extended duplexes contained phosphorothioate backbone modifications in the single stranded extension region. For duplexes DNA10PS, RNA10PS, RNA10PS-2'-OME, having 10 nucleotide single stranded guide extensions, KRAS-249 gene expression was reduced about 75-85%. For duplexes DNA10PS, RNA10PS, RNA10PS-2'-OME, having 15 nucleotide single stranded guide extensions, KRAS-249 gene expression was reduced 60-70%. Generally, the duplexes having the 10 nucleotide guide extensions reduced KRAS target gene expression more than the duplexes having the 15 nucleotide guide extensions, regardless of the nucleotides present in the 5' guide extensions. In particular, the silencing activity of duplexes having guide extensions containing deoxyribonucleotides, was more sensitive to the increased length of 15 nucleotides, compared to the duplexes containing ribonucleotides and 2'-O-methyl ribonucleotides. Processing of 5' guide strand extended duplexes by Dicer, which were used in the experiments targeting gene expression of KRAS-249, was also shown by in vitro assay (FIG. 10).

Similarly, under the same conditions (0.1 nM duplexes, Lipofectamine™ RNAiMAX transfection), HPRT1 gene expression was reduced by about 65-85% by duplexes DNA10PS, RNA10PS, RNA10PS-2'-OME, DNA15PS, RNA15PS, and RNA15PS-2'OME (FIG. 9). By comparison, a duplex without the single stranded guide extensions reduced HPRT1 gene expression by about 90%. Thus, the duplexes having single stranded guide extensions were as effective in silencing HPRT1 as a duplex without the single stranded guide extensions. All single stranded extended duplexes contained phosphorothioate backbone modifications in the single stranded extension region. For duplexes DNA10PS, RNA10PS, RNA10PS-2'-OME, having 10 nucleotide single stranded guide extensions, KRAS-249 gene expression was reduced about 80-85%. For duplexes DNA10PS, RNA10PS, RNA10PS-2'-OME, having 15 nucleotide single stranded guide extensions, KRAS-249 gene expression was reduced 60-80%. Generally, the duplexes having the 10 nucleotide guide extensions reduced KRAS target gene expression more than the duplexes having the 15 nucleotide guide extensions, regardless of the nucleotides present in the 5' guide extensions. In particular, the silencing activity of duplexes having guide extensions containing deoxyribonucleotides or 2'-O-methyl ribonucleotides, was more sensitive to the increased length of 15 nucleotides, compared to the duplexes containing ribonucleotides. Processing of 5' guide strand extended duplexes by Dicer, which were used in the experiments targeting gene expression of HPRT1, was also shown by in vitro assay (FIG. 10).

Because the duplex having the single stranded guide extensions were as effective in silencing KRAS-249 and HPRT1, respectively, as a duplex without the single stranded guide extensions, this discovery allows for the modification of DsiRNA agents with single stranded guide extensions without loss of efficacy.

Example 3

Efficacy of DsiRNA Agents Possessing Single Stranded Extensions in Combination with a Short Oligonucleotide Complementary to the Single Stranded Extension DsiRNA agents possessing single stranded extensions were examined for efficacy of sequence-specific target mRNA inhibition in combination with a short oligo complementary to the single stranded extension. Specifically, KRAS-249M and HPRT-targeting DsiRNA duplexes possessing 15 nucleotide long 5' single stranded guide extensions including a 15 nucleotide discontinuous complement were transfected into HeLa cells at a fixed concentration of 20 nM and HPRT expression levels were measured 24 hours later (FIGS. 12 and 13). Transfections were performed in duplicate, and each duplicate was assayed in triplicate for KRAS-249M and HPRT expression, respectively, by qPCR.

Under these conditions (0.1 nM duplexes, Lipofectamine™ RNAiMAX transfection), KRAS-249 gene expression was reduced by about 15-60% by duplexes DNA15PS (1301+1340), RNA15PS (1301+1341), RNA15PS-2'-OME (1301+1342) in the presence of discontinuous complements RNA15, PS-RNA15, PS-DNA15, PS-2'OMe-RNA15, and 2'OMe-RNA15 (FIG. 12). A duplex without the single stranded guide extensions reduced KRAS-249 gene expression by about 85%. All single stranded extended duplexes contained phosphorothioate backbone modifications in the single stranded extension region. Generally, the duplexes having ribonucleotide or 2'-O-methyl ribonucleotide guide extensions reduced KRAS target gene expression more than the duplexes having deoxyribonucleotide guide extensions, regardless of the discontinuous complement present. For duplexes DNA15PS (1301+1340), RNA15PS (1301+1341), RNA15PS-2'-OME (1301+1342), the reductions in gene expression were comparable with or without the 2'OMe-RNA15 discontinuous complement.

Similarly, under the same conditions (0.1 nM duplexes, Lipofectamine™ RNAiMAX transfection), HPRT1 gene expression was reduced by about 30-85% by duplexes DNA15PS (1001+1353), RNA15PS (1001+1354), and RNA15PS-2'OME (1001+1355) in the presence of discontinuous complements RNA15, PS-RNA15, PS-DNA15, PS-2'OMe-RNA15, and 2'OMe-RNA15 (FIG. 13). A duplex without the single stranded guide extensions reduced HPRT1 gene expression by about 90%. All single stranded extended duplexes contained phosphorothioate backbone modifications in the single stranded extension region. Generally, the duplexes having ribonucleotide or 2'-O-methyl ribonucleotide guide extensions reduced KRAS target gene expression more than the duplexes having deoxyribonucleotide guide extensions, regardless of the discontinuous complement present. Duplexes RNA15PS (1301+1341) and RNA15PS-2'-OME (1301+1342), showed enhanced reduction in gene expression in the presence of discontinuous complements RNA15, PS-RNA15, PS-2'OMe-RNA15, 2'OMe-RNA15, compared to the same duplexes RNA15PS (1301+1341) and RNA15PS-2'-OME (1301+1342) without any discontinuous complement.

Example 4

In Vivo Efficacy of DsiRNA Agents

DsiRNA agents possessing DNA duplex extensions were examined for in vivo efficacy of sequence-specific target mRNA inhibition either in a single dose protocol or in a repeated dose protocol (e.g., single 10 mg/kg injection in invivoFectamine). Expression of KRAS in liver, kidney, spleen and lymph node tissues was measured 24 hours post-injection, with real-time PCR (RT-PCR) performed in triplicate to assess KRAS expression. Under these conditions, single stranded guide extended DsiRNA agents exhibited statistically significant levels of KRAS target gene inhibition in all tissues examined. KRAS percent inhibition levels in such single stranded guide extension DsiRNA treated tissues were: liver (10%, 20%, 30%, 40%, 50%, 60%, 70%, 80%, 90%, 95%, 96%, 97%, 98%, 99%, or 100%), spleen (10%, 20%, 30%, 40%, 50%, 60%, 70%, 80%, 90%, 95%, 96%, 97%, 98%, 99%, or 100%),), kidney (1910%, 20%, 30%, 40%, 50%, 60%, 70%, 80%, 90%, 95%, 96%, 97%, 98%, 99%, or 100%),) and lymph nodes (10%, 20%, 30%, 40%, 50%, 60%, 70%, 80%, 90%, 95%, 96%, 97%, 98%, 99%, or 100%)). Thus, the in vivo efficacy of the extended DsiRNAs of the instant invention was demonstrated across many tissue types.

Further demonstration of the capability of the extended Dicer substrate agents of the invention to reduce gene expression of specific target genes in vivo was performed via administration of the DsiRNAs of the invention to mice or other mammalian subjects, either systemically (e.g., by i.v. or i.p. injection) or via direct injection of a tissue (e.g., injection of the eye, spinal cord/brain/CNS, etc.). Measurement of additional target RNA levels were performed upon target cells (e.g., RNA levels in liver and/or kidney cells were assayed following injection of mice; eye cells were assayed following ophthalmic injection of subjects; or spinal cord/brain/CNS cells were assayed following direct injection of same of subjects) by standard methods (e.g., Trizol® preparation (guanidinium thiocyanate-phenol-chloroform) followed by qRT-PCR).

In any such further in vivo experiments, an extended Dicer substrate agent of the invention (e.g., a guide 5' extended or passenger 3' extended DsiRNA) can be deemed to be an effective in vivo agent if a statistically significant reduction in RNA levels was observed when administering an extended Dicer substrate agent of the invention, as compared to an appropriate control (e.g., a vehicle alone control, a randomized duplex control, a duplex directed to a different target RNA control, etc.). Generally, if the p-value (e.g., generated via 1 tailed, unpaired T-test) assigned to such comparison was less than 0.05, an extended Dicer substrate agent (e.g., guide 5' extended or passenger 3' extended DsiRNA agent) of the invention was deemed to be an effective RNA interference agent. Alternatively, the p-value threshold below which to classify an extended Dicer substrate agent of the invention as an effective RNA interference agent can be set, e.g. at 0.01, 0.001, etc., in order to provide more stringent filtering, identify more robust differences, and/or adjust for multiple hypothesis testing, etc. Absolute activity level limits can also be set to distinguish between effective and non-effective extended Dicer substrate agents. For example, in certain embodiments, an effective extended Dicer substrate agent of the invention was one that not only shows a statistically significant reduction of target RNA levels in vivo but also exerts, e.g., at least an approximately 10% reduction, approximately 15% reduction, at least approximately 20% reduction, approximately 25% reduction, approximately 30% reduction, etc. in target RNA levels in the tissue or cell that was examined, as compared to an appropriate control. Further in vivo efficacy testing of the extended Dicer substrate agents (e.g., guide 5' extended and passenger 3' extended DsiRNA agents) of the invention was thereby performed.

Figure 15B:
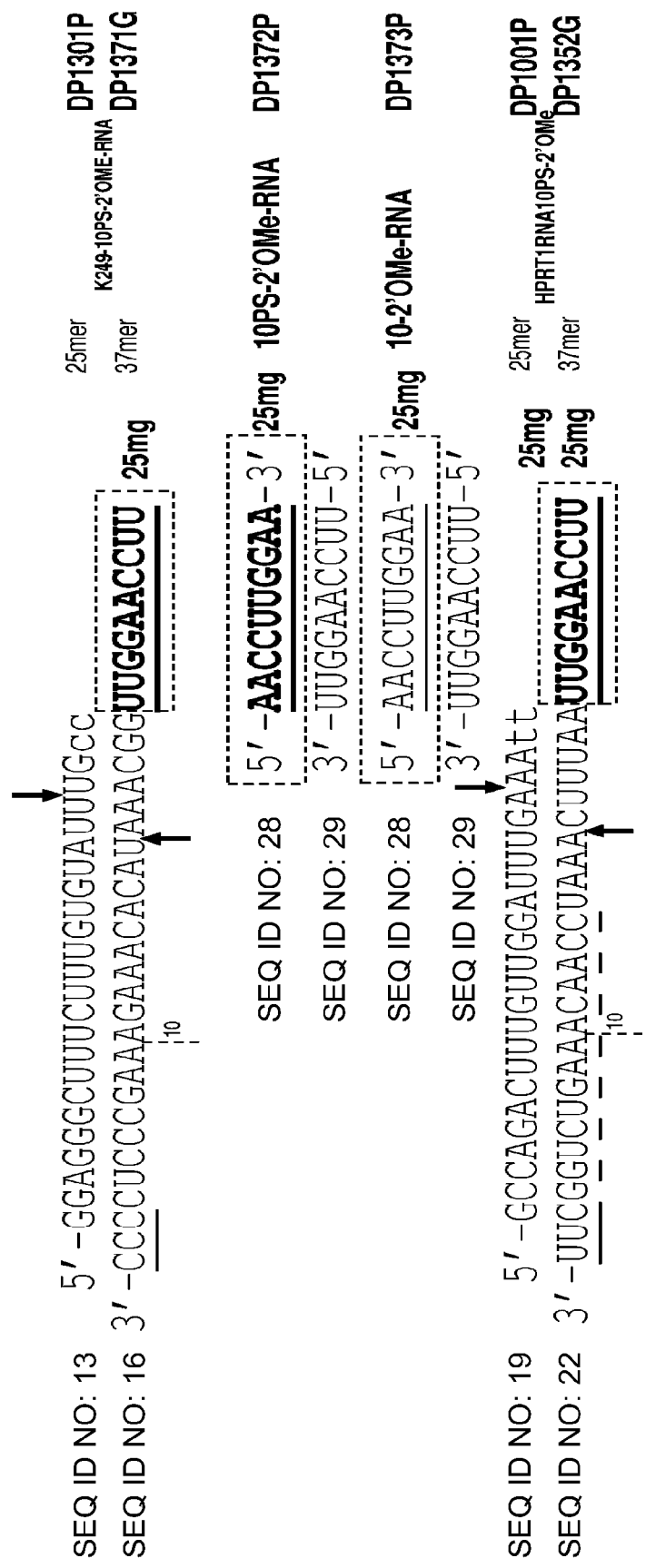
FIGS. 15A and B shows the sequence, structure, and predicted Dicer-mediated processing of exemplary "guide strand extended" DsiRNA agents targeting KRAS-249M and HPRT1, which have a guide strand 5' overhang 1-15 nucleotides in length. The sequence and structure of exemplary short oligos that complement guide strand extensions ("discontinuous complements") are shown base paired to 5' guide strand extension sequences. Single stranded guide extended DsiRNA agents having a passenger strand with the modification pattern depicted by DP1301P and a guide strand with a modification pattern depicted by DP1337G, DP1338G, DP1339G, DP1371G, and DP1352G were generated. Additionally, the single stranded extended DsiRNA agents having a passenger strand with the modification pattern depicted in DP1301P, a guide strand with a modification pattern depicted by DP1337G, DP1338G, DP1339G, DP1371G, and DP1352G; and an "discontinuous complement" strand with a modification pattern depicted by DP1372P and DP1373P were generated. DsiRNA agents having a passenger strand with the modification depicted by DP1301P were used as a reference and a guide strand with the modification depicted by DP1370G were used as a reference. Dosage of passenger strands, guide strands, and discontinuous complements are labeled to the right. Descriptions of the modification patterns of the discontinuous complements are also labeled on the right. RNA=ribonucleotide; PS=phosphorothioate; DNA=deoxyribonucleotide; 2'OMe=2'-O-methyl; Underline=2'-O-methyl ribonucleotide; Bold=guide strand 5' overhang; lower=deoxyribonucleotide; UPPER=ribonucleotide. Arrows indicate predicted Dicer cleavage sites.

DsiRNA agents possessing single stranded extensions (FIGS. 14 and 15) effectively inhibited the sequence-specific target KRAS mRNA expression in vivo in liver, spleen, and kidney. In liver, the 5' passenger extended DsiRNA agents 1371 (PS 3M) and 1339 (PS10M) showed inhibition of KRAS mRNA expression as compared to DsiRNA agents without the 5' passenger extensions K249M and 1370 (3M), when normalized to glucose only control (FIGS. 16-18). The inhibition of KRAS mRNA expression by the DsiRNA agents was at least 75-90% in liver of animals injected with the 5' passenger extended DsiRNA agents 1371 (PS 3M) and 1339 (PS10M). The amount of inhibition of the 5' passenger extended DsiRNA agents 1371 (PS 3M) and 1339 (PS10M) in liver was comparable to that of DsiRNA agents without the 5' passenger extensions K249M and 1370 (3M), which was significant compared to the negative glucose control.

In spleen, the 5' passenger extended DsiRNA agents 1371 (PS 3M) and 1339 (PS 10M) also showed inhibition of KRAS mRNA expression as compared to DsiRNA agents without the 5' passenger extensions K249M and 1370 (3M), when normalized to glucose only control (FIGS. 19-21). The inhibition of KRAS mRNA expression by the DsiRNA agents was at least 90-95% in spleen of animals injected with the 5' passenger extended DsiRNA agents 1371 (PS 3M) and 1339 (PS10M). The amount of inhibition of the 5' passenger extended DsiRNA agents 1371 (PS 3M) and 1339 (PS10M) in spleen was comparable to that of DsiRNA agents without the 5' passenger extensions K249M and 1370 (3M), which was significant compared to the negative glucose control.

In kidney, the 5' passenger extended DsiRNA agents 1371 (PS 3M) and 1339 (PS 10M) showed inhibition of KRAS mRNA expression as compared to DsiRNA agents without the 5' passenger extensions K249M and 1370 (3M), when normalized to glucose only control (FIGS. 22-24). The inhibition of KRAS mRNA expression by the DsiRNA agents was at least 20-40% in kidney of animals injected with the 5' passenger extended DsiRNA agents 1371 (PS 3M) and 1339 (PS10M). Nevertheless, the amount of inhibition of the 5' passenger extended DsiRNA agents 1371 (PS 3M) and 1339 (PS 10M) was comparable to that of DsiRNA agents without the 5' passenger extensions K249M and 1370 (3M). In these experiments, a DsiRNA agent without the 5' passenger extension M97M and not sequence specific to KRAS was used as a positive control.

Because the DsiRNA agents having a single stranded guide extension were as effective in silencing KRAS in vivo, as DsiRNA agents without the single stranded guide extension, this discovery allows for the modification of DsiRNA agents with single stranded guide extensions without loss of efficacy in vivo.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying DsiRNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated double stranded nucleic acid comprising a first oligonucleotide strand having a 5' terminus and a 3' terminus and a second oligonucleotide strand having a 5' terminus and a 3' terminus, wherein each said 5' terminus comprises a 5' terminal nucleotide and each said 3' terminus comprises a 3' terminal nucleotide, wherein:

said first strand is 25-30 nucleotide residues in length, wherein starting from the 5' terminal nucleotide (position 1) positions 1 to 23 of said first strand comprise at least 8 ribonucleotides;

said second strand is 36-66 nucleotide residues in length and, starting from the 3' terminal nucleotide, comprises at least 8 ribonucleotides in the positions paired with positions 1-23 of said first strand to form a duplex;

wherein at least the 3' terminal nucleotide of said second strand is unpaired with said first strand, and up to 6 consecutive 3' terminal nucleotides are unpaired with said first strand, thereby forming a 3' single stranded overhang of 1-6 nucleotides;

wherein the 5' terminus of said second strand comprises from 10-30 consecutive nucleotides which are unpaired with said first strand, thereby forming a 10-30 nucleotide single stranded 5' overhang;

wherein at least the first strand 5' terminal and 3' terminal nucleotides are base paired with nucleotides of said second strand when said first and second strands are aligned for maximum complementarity, thereby forming a substantially duplexed region between said first and second strands; and said second strand is sufficiently complementary to a target RNA along at least 19 ribonucleotides of said second strand length to reduce target gene expression when said double stranded nucleic acid is introduced into a mammalian cell.

2. The isolated double stranded nucleic acid of claim 1, wherein at least one nucleotide of said first strand between and including said first strand positions 24 to the 3' terminal nucleotide residue of said first strand is a deoxyribonucleotide.

3. The isolated double stranded nucleic acid of claim 1, wherein at least 10 consecutive nucleotides and at most 15 consecutive nucleotides of said second strand, not including the unpaired 3' terminal nucleotides of said second strand are unpaired with said first strand, thereby forming in said second strand a 10-15 nucleotide single stranded 5' overhang.

4. The isolated double stranded nucleic acid of claim 1, wherein at least one nucleotide of said second strand between and including second strand nucleotides corresponding to and thus base paired with first strand positions 24 to the 3' terminal nucleotide residue of said first strand is a ribonucleotide.

5. The isolated double stranded nucleic acid of claim 1, wherein said substantially duplexed region between said first and second strands comprises a fully duplexed region having no unpaired bases between the 5' terminal and 3' terminal nucleotides of said first strand that are paired with corresponding nucleotides of said second strand.

6. The isolated double stranded nucleic acid of claim 5, wherein said substantially duplexed region comprises, between the 5' terminal and 3' terminal nucleotides of said first strand that are paired with corresponding nucleotides of said second strand, from 1-5 unpaired base pairs.

7. The isolated double stranded nucleic acid of claim 6, wherein said unpaired base pairs are consecutive or non-consecutive.

8. The isolated double stranded nucleic acid of claim 1, wherein said first strand is up to 30 nucleotides in length, and the nucleotides of said first strand 3' to position 23 of said first strand comprise deoxynucleotides selected from the group consisting of two, three, four, five, and six deoxyribonucleotides that base pair with a nucleotide of said second strand.

9. The isolated double stranded nucleic acid of claim 8, wherein said deoxyribonucleotides of said first strand that base pair with a nucleotide of said second strand are consecutive deoxyribonucleotides.

10. The isolated double stranded nucleic acid of claim 1, wherein two or more consecutive nucleotide residues of positions 24 to 30 of said first strand are deoxyribonucleotides that base pair with nucleotides of said second strand.

11. The isolated double stranded nucleic acid of claim 10, wherein said first strand is up to 30 nucleotides in length and comprises a pair of deoxyribonucleotides selected from the group consisting of positions 24 and 25, positions 25 and 26, positions 26 and 27, positions 27 and 28, positions 28 and 29, and positions 29 and 30, wherein said first strand pair of deoxyribonucleotides is base paired with a corresponding pair of nucleotides of said second strand.

12. The isolated double stranded nucleic acid of claim 1, wherein said 8 or more ribonucleotides of positions 1 to 23 of said first strand are consecutive ribonucleotides.

13. The isolated double stranded nucleic acid of claim 12, wherein each nucleotide residue of positions 1 to 23 of said first oligonucleotide strand is a ribonucleotide that base pairs with a nucleotide of said second strand.

14. The isolated double stranded nucleic acid of claim 1, wherein said 3' single stranded overhang of said second strand is a length selected from the group consisting of 1 to 4 nucleotides, 1 to 3 nucleotides, 1 to 2 nucleotides, and 2 nucleotides in length.

15. The isolated double stranded nucleic acid of claim 1, wherein said nucleotides of said second strand 3' overhang comprise a modified nucleotide.

16. The isolated double stranded nucleic acid of claim 15, wherein said modified nucleotide is selected from the group consisting of 2'-O-methyl, 2'methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and 2'-O—N-methlycarbamate).

17. The isolated double stranded nucleic acid of claim 15, wherein said modified nucleotide of said second strand 3' overhang is a 2'-O-methyl ribonucleotide.

18. The isolated double stranded nucleic acid of claim 1, wherein said second strand 3' overhang is two nucleotides in length and possesses a 2'-O-methyl modified ribonucleotide in said 3' overhang.

19. The isolated double stranded nucleic acid of claim 1, wherein said second strand, starting from the nucleotide residue of said second strand that corresponds to the 5' terminal nucleotide residue of said first oligonucleotide strand (said corresponding nucleotide of said second strand being defined as position $1^A$ and the $16^{th}$ consecutive nucleotide of said second strand 5' distal to position $1^A$ in said second strand being defined as position $16^A$), comprises unmodified nucleotide residues at all positions inclusive of position $16^A$ to and including the 5' residue of said second strand that corresponds to the 3' terminal residue of said first strand.

20. The isolated double stranded nucleic acid of claim 1, wherein said 3' terminus of said second strand comprises three contiguous modified nucleotides (where the three 3' terminal nucleotides of said second strand are referred to as positions $1^D$, $2^D$, and $3^D$), such that each of said position $1^D$, $2^D$, and $3^D$ of said second strand comprises a modified nucleotide.

21. The isolated double stranded nucleic acid of claim 1, wherein said second oligonucleotide strand, starting from the nucleotide residue of said second strand that corresponds to the 5' terminal nucleotide residue of said first oligonucleotide strand (said corresponding nucleotide residue of said second strand being defined as position $1^A$ and wherein consecutive nucleotides in the 3' to 5' direction of said second strand are referred to as consecutively numbered positions), comprises alternating modified and unmodified nucleotide residues from second strand position $1^A$ to second strand position $15^B$.

22. The isolated double stranded nucleic acid of claim 1, wherein said second strand 5' overhang comprises a phosphate backbone modification between at least two contiguous nucleotides of said second strand 5' overhang.

23. The isolated double stranded nucleic acid of claim 22, wherein said phosphate backbone modification is selected from the group consisting of a phosphonate, a phosphorothioate, a phosphotriester, a methylphosphonate, a locked nucleic acid, a morpholino, and a bicyclic furanose analog.

24. The isolated double stranded nucleic acid of claim 23, wherein said second strand starting from the 5' terminal nucleotide residue of said second strand (said 5' terminal second strand residue being defined as position $1^B$ and the penultimate 5' terminal second strand residue being defined as position $2^B$), comprises a phosphorothioate backbone modification between the nucleotides from position $2^B$ to the 5' residue of said second strand that corresponds to the 3' terminal residue of said first strand.

25. The isolated double stranded nucleic acid of claim 1, wherein said nucleotides of said second strand 5' overhang comprise a modified nucleotide.

26. The isolated double stranded nucleic acid of claim 25, wherein said modified nucleotide is selected from the group consisting of 2'-O-methyl, 2'methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and 2'-O-(N-methlycarbamate).

27. The isolated double stranded nucleic acid of claim 25, wherein said modified nucleotide of said second strand 5' overhang is a 2'-O-methyl ribonucleotide.

28. The isolated double stranded nucleic acid of claim 25, wherein the 5' terminal nucleotide residue of the second strand is a 2'-O-methyl ribonucleotide.

29. The isolated double stranded nucleic acid of claim 1, wherein a nucleotide of said second or first oligonucleotide strand is substituted with a modified nucleotide that directs the orientation of Dicer cleavage.

30. The isolated double stranded nucleic acid of claim 1, wherein the first strand has a nucleotide sequence that is at least 80%, 90%, 95% or 100% complementary to the second strand nucleotide sequence between said first strand 5' terminal and 3' terminal nucleotides when said first and second strands are aligned for maximum complementarity, in said substantially duplexed region between said first and second strands.

31. The isolated double stranded nucleic acid of claim 1, wherein said target RNA is KRAS.

32. An isolated multi-stranded nucleic acid comprising a first oligonucleotide strand having a 5' terminus and a 3' terminus, a second oligonucleotide strand having a 5' terminus and a 3' terminus, and a third oligonucleotide strand having a 5' terminus and a 3' terminus, wherein each said 5' terminus comprises a 5' terminal nucleotide and each said 3' terminus comprises a 3' terminal nucleotide, wherein:

said first strand is 25-30 nucleotide residues in length, wherein starting from the 5' terminal nucleotide (position 1) positions 1 to 23 of said first strand comprise at least 8 ribonucleotides;

said second strand is 36-66 nucleotide residues in length and, starting from the 3' terminal nucleotide, comprises at least 8 ribonucleotides in the positions paired with positions 1-23 of said first strand to form a duplex;

said third strand is 10-30 nucleotide residues in length;

wherein at least the 3' terminal nucleotide of said second strand is unpaired with said first strand, and up to 6 consecutive 3' terminal nucleotides are unpaired with said first strand, thereby forming a 3' single stranded overhang of 1-6 nucleotides;

wherein the 5' terminus of said second strand comprises from 10-30 consecutive nucleotides which are unpaired with said first strand and wherein at least 10 consecutive nucleotides and at most 30 consecutive nucleotides of said third strand are sufficiently complementary to said second strand to hybridize with said second strand at said 10-30 consecutive nucleotides of said second strand which are unpaired with said first strand;

wherein at least the first strand 5' terminal and 3' terminal nucleotides are base paired with nucleotides of said second strand when said first and second strands are aligned for maximum complementarity, thereby forming a substantially duplexed region between said first and second strands; and said second strand is sufficiently complementary to a target RNA along at least 19 ribonucleotides of said second strand length to reduce target gene expression when said multi-stranded nucleic acid is introduced into a mammalian cell.

33. The isolated double stranded nucleic acid of claim 32, wherein said third strand comprises a ribonucleotide or deoxyribonucleotide.

34. The isolated double stranded nucleic acid of claim 32, wherein all nucleotides of said 10-30 consecutive nucleotides of said second strand which are unpaired with said first strand are ribonucleotides.

35. The isolated double stranded nucleic acid of claim 32, wherein said nucleotides of said third strand comprise a modified nucleotide.

36. The isolated double stranded nucleic acid of claim 35, wherein said modified nucleotide of said third strand is selected from the group consisting of 2'-O-methyl, 2'methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and 2'-O-(N-methlycarbamate).

37. The isolated double stranded nucleic acid of claim 35, wherein said modified nucleotide of said third strand is a 2'-O-methyl ribonucleotide.

38. The isolated double stranded nucleic acid of claim 32, wherein said third strand comprises a phosphate backbone modification.

39. The isolated double stranded nucleic acid of claim 38, wherein said phosphate backbone modification is selected from the group consisting of a phosphonate, a phosphorothioate, a phosphotriester, a methylphosphonate, a locked nucleic acid, a morpholino, and a bicyclic furanose analog.

40. The isolated double stranded nucleic acid of claim 39, wherein said third strand starting from the 5' terminal nucleotide residue of said third strand (position $1^C$), comprises a phosphorothioate backbone modification between the nucleotides at positions $1^C$ and $2^C$.

41. The isolated double stranded nucleic acid of claim 32, wherein at least one nucleotide of said first strand between and including said first strand positions 24 to the 3' terminal nucleotide residue of said first strand is a deoxyribonucleotide.

42. The isolated double stranded nucleic acid of claim 32, wherein at least one nucleotide of said second strand between and including second strand nucleotides corresponding to and thus base paired with first strand positions 24 to the 3' terminal nucleotide residue of said first strand is a ribonucleotide.

43. The isolated double stranded nucleic acid of claim 32, wherein said substantially duplexed region between said first and second strands comprises a fully duplexed region having no unpaired bases between the 5' terminal and 3' terminal nucleotides of said first strand that are paired with corresponding nucleotides of said second strand.

44. The isolated double stranded nucleic acid of claim 32, wherein said substantially duplexed region between said third and second strands comprises a fully duplexed region having no unpaired bases between the 5' terminal and 3' terminal nucleotides of said third strand that are paired with corresponding nucleotides of said second strand.

45. The isolated double stranded nucleic acid of claim 32, wherein said substantially duplexed region between said first and second strands, between the 5' terminal and 3' terminal nucleotides of said first strand that are paired with corresponding nucleotides of said second strand, comprises 1-5 unpaired base pairs.

46. The isolated double stranded nucleic acid of claim 32, wherein said 10-30 consecutive nucleotides of said 5' terminus of said second strand which are unpaired with said first strand comprise a phosphate backbone modification.

* * * * *